United States Patent [19]
Ogura et al.

[11] Patent Number: 5,649,536
[45] Date of Patent: Jul. 22, 1997

[54] BLOOD PRESSURE MEASURING APPARATUS

[75] Inventors: Toshihiko Ogura, Inuyama; Toru Oka, Ichinomiya, both of Japan

[73] Assignee: Colin Corporation, Komaki, Japan

[21] Appl. No.: 391,701

[22] Filed: Feb. 21, 1995

[30] Foreign Application Priority Data

| | | | |
|---|---|---|---|
| Feb. 25, 1994 | [JP] | Japan | 6-028164 |
| Mar. 1, 1994 | [JP] | Japan | 6-031064 |
| Mar. 1, 1994 | [JP] | Japan | 6-031567 |
| Apr. 5, 1994 | [JP] | Japan | 6-067112 |
| May 17, 1994 | [JP] | Japan | 6-005342 U |
| Sep. 8, 1994 | [JP] | Japan | 6-214425 |

[51] Int. Cl.⁶ ............................................. A61B 5/00
[52] U.S. Cl. ........................... 128/680; 128/681; 128/682
[58] Field of Search .......................... 128/672, 670, 128/680–683, 687

[56] References Cited

U.S. PATENT DOCUMENTS

| | | | |
|---|---|---|---|
| 4,889,133 | 12/1989 | Nelson et al. | 128/681 |
| 4,949,710 | 8/1990 | Dorsett et al. | 128/680 |
| 4,984,577 | 1/1991 | Frankenreiter | 128/681 |
| 5,406,954 | 4/1995 | Tomita | 128/680 |
| 5,505,206 | 4/1996 | Walloch | 128/681 |

FOREIGN PATENT DOCUMENTS

| | | |
|---|---|---|
| 60-241422 | 11/1985 | Japan . |
| 61-103432 | 5/1986 | Japan . |
| 63-51837 | 3/1988 | Japan . |
| 2-25610 | 6/1990 | Japan . |
| 5-137698 | 6/1993 | Japan . |

*Primary Examiner*—Robert L. Nasser
*Attorney, Agent, or Firm*—Oliff & Berridge

[57] ABSTRACT

A apparatus for measuring blood pressure of a living subject, including a blood pressure measuring device which receives a heartbeat synchronous-signal wave generated by arteries of the patient, determines respective amplitudes of successive pulses of said heartbeat-synchronous signal wave, each of which corresponds to one heartbeat of the subject, and provides as a first series of pulse amplitudes, the pulse amplitudes arranged in order of generation. The device further smoothens the first series of pulses and provides a second series of smoothened pulse amplitudes, and determines a blood pressure value based on a change in the second series. The device further provides a two-dimensional output of the first and second series, where one of the two series is superimposed on the other, and/or a representation of the degree of propriety of the measurement condition during which the measurement was performed.

12 Claims, 51 Drawing Sheets

BLOOD PRESSURE MEASURING APPARATUS

BACKGROUND OF THE INVENTION

1. Field of the Invention

The present invention relates to the improvements of a blood pressure measuring apparatus which measures a blood pressure value of a living subject such as a patient.

2. Related Art Statement

There is known an automatic blood pressure (BP) measuring apparatus which carries out BP measurements on a patient, accumulatively stores a measured BP value or values obtained in each BP measurement, and provides a graphic representation of the stored BP values arranged in the order of measurement. An example of the BP measuring apparatus is disclosed in Non-Examined Japanese Patent Application laid open under Publication No. 5(1993)-137698. The BP apparatus enables the patient to easily recognize the time change of the measured BP values and correctly judge whether he or she is in a healthy condition. When the patient feels tight in the chest, such a light attack may, however, be transient, so that the patient may fail to recognize that he or she possibly has a serious heart disease. Even if the patient may reach the recognition and consult a doctor, then the patient may no longer have any subjective symptom and may appear to the doctor to have no medical problem. In this case, the doctor may make a diagnosis based on insufficient examination data, e.g., BP values only. If the prior BP apparatus is used to obtain the BP values of the patient, however, the BP apparatus provides only the measured BP values of the patient, or only the time change of the measured BP values. With those data, the patient may suspect that he or she may have hypertension, but the patient cannot make a self-diagnosis, or the doctor cannot make a medical diagnosis, that he or she may have a heart disease. If the patient continues his or her life without receiving any medical treatments, he or she might be brought into a serious condition.

There is also known an automatic BP measuring apparatus which has a BP measuring device for automatically measuring a BP value or values of a living body, and a BP-value storing device for accumulatively storing the BP values measured by the BP measuring device from the living body. The BP measuring apparatus outputs the BP values accumulatively stored in the BP-value storing device, each time a new BP value or values of the subject is/are measured by the BP measuring device. Thus, the living body can easily recognize the time change of his or her BP values and effectively utilize the BP values for his or her health control. However, in the case where the BP values output from the BP apparatus do not fall within a normal BP range and care should be taken of the Living body, just the marshalling of figures would give only a weak visual impression to the living body. Even if the living body may recognize his or her blood pressure abnormality, he or she is likely to forget it. While it is possible to output a pictorial image together with the BP values to give a stronger visual impression to the living body, it needs much time and effort to prepare the pictorial image or images. Moreover, in the case where a doctor gives a blood pressure-treating medicine to a patient after having made a diagnosis based on measured BP values, it may be somewhat cumbersome for the doctor to explain the directions for use of the medicine, the objects of administration of the same, and other necessary items.

Next, there is known an arm belt which is, either manually or using a winding device, wound around an upper arm of a living body or subject and which has an inflatable bag to which a pressurized air is supplied to press the arteries of the arm and measure a BP value or values of the subject. The supplying of the air to the bag is effected after the belt is wound around subject's arm, and the measurement of BP values is carried out while the air pressure of the bag is changed. It is preferred that the belt be wound around the arm such that three fingers can be inserted between the skin of the arm and the inside surface of the belt. However, since the upper arm of the subject around which the arm belt is wound is easily deformable, a certain level of skill is needed for winding the belt wound the arm with a preferable pressing force and measuring a BP value or values of the subject with accuracy. Hence, there has been used a winding device which automatically winds an arm belt around an upper arm of a living subject. The automatic winding device has a cylindrical arm receiver in which the belt taking a cylindrical shape is provided, and has a drive device such as a motor for tightening the belt. After the subject inserts his or her arm into the belt inside the receiver through one end of the receiver, the drive device is operated to tighten the belt and thereby reduce the inside diameter of the cylindrical belt. Thus, the arm belt is automatically wound around the subject's upper arm. When a BP measurement is carried out using the automatic winding device, it is required that the arteries of the upper arm of the subject be uniformly pressed by the arm belt. To this end, generally, an elbow rest is provided outside the other end of the arm receiver, and the subject inserts his or her arm such that the elbow of the arm rests on the rest. The diameter of the belt is reduced when the subject is taking such a posture that the upper arm is not in contact with the inner wall of the above-mentioned one end of the receiver. That is, it is preferred that the longitudinal axis line of the upper arm of the subject be kept substantially parallel to the central axis line of the cylindrical arm receiver. However, ordering the subject to change his or her natural posture to the above-mentioned posture may result in forcing the subject to take an unnatural posture, depending upon the conformation of his or her body. This problem is exaggerated in particular for patients or aged persons who are not so free to change their postures. In the latter cases, the accuracy of BP measurements may be lowered.

There is known a BP monitor apparatus which monitors the blood pressure of a living subject. The BP monitor apparatus includes an automatic BP measuring device including an inflatable cuff adapted to be wound around a body portion of the subject. The automatic BP measuring device is iteratively started to measure a BP value or values of the subject. Thus, the BP monitor apparatus carries out BP measurements periodically, i.e., at a prescribed measurement period. However, if the measurement period is prescribed at so short a period to improve the reliability of the BP monitoring, the frequency of pressing of the subject's body portion with the cuff is increased so that the subject feels a heavy burden. In this situation, there has been proposed a BP monitor apparatus which increases the pressure of an inflatable cuff wound around a body portion of a living subject, up to a prescribed target pressure value, detects a pulse wave as a pressure oscillation produced in the cuff, and continuously estimates a BP value or values based on a magnitude or magnitudes of each of successive heartbeat-synchronous pulses of the pulse wave. Examples of this BP monitor apparatus are disclosed in Non-Examined Japanese Patent Applications No. 61(1986)-103432 and No. 60(1985)-241422. In the latter case, however, if the target pressure is prescribed at as low as possible a value to reduce the burden to the subject, it might be difficult to detect the change of respective amplitudes of successive pulses of the pulse wave corresponding to the change of BP values of the subject. That is, the reliability of the BP monitoring is lowered. The pulse amplitudes detected from the cuff set on people having normal blood pressure change with the cuff pressure so as to have an envelope indicated at solid line in FIG. 29, whereas the pulse amplitudes obtained from people having low blood pressure change with the cuff pressure so as to have an envelope indicated at broken line. Since the amount of change of the pulse amplitudes with respect to the amount of change of the BP values of a subject is more or less small where the pulse amplitudes are obtained at a relatively low cuff pressure such as a value, $P_K$, shown in FIG. 29, the reliability of the BP monitoring at the low cuff pressure $P_K$ is insufficiently low.

Furthermore, there is known an automatic BP measuring apparatus which quickly increases the pressure of an inflatable cuff wound around a body portion of a living subject, up to a target pressure value at which the inflated cuff stops the blood flow through the arteries of the body portion, subsequently slowly decreases the cuff pressure at a rate of 2 to 3 mmHg/sec, and measures a BP value or values of the subject during the slow decreasing of the cuff pressure. There are known two BP measuring techniques, i.e., oscillometric method and Korotkoff-sound method. In the oscillometric method, the pressure oscillation produced in the cuff during the slow decreasing of the cuff pressure is detected as a pulse wave, and the systolic and diastolic BP values of the subject are determined based on the change of respective amplitudes of successive heartbeat-synchronous pulses of the pulse wave. In the Korotkoff-sound method, the Korotkoff sounds, i.e., blood-flow sounds produced from the arteries of the body portion during the slow decreasing of the cuff pressure are detected using a microphone, and the systolic and diastolic BP values of the subject are determined based on the two cuff-pressure values at which the first and last Korotkoff sounds are detected, respectively. In these BP measuring methods, the accuracy of measurement of BP values depends on the amount of change of the cuff pressure corresponding to the interval of occurrence of the successive pulses of the pulse wave or the successive Korotkoff sounds. Therefore, for measuring the BP value or values of the subject with accuracy, the automatic BP measuring apparatus carries out the BP measurement while the cuff pressure is slowly decreased. However, since in the prior BP measuring apparatus the cuff pressure is slowly decreased in carrying out the BP measurement, it takes about twenty seconds to obtain the measured BP value or values of the subject. Before this slow cuff-pressure decreasing, no BP value is available to a medical worker such as a doctor. In the case where a doctor should make a quick decision on an emergency patient, or in the case where a target value higher by a prescribed value than the systolic BP value of a subject should be determined while the cuff pressure is quickly increased, so that the cuff pressure is stopped at the thus determined target value, it is required that a BP value of the subject be known, even though it is rough, before a BP measurement is carried out during the slow decreasing of the cuff pressure.

Moreover, there is known the oscillometric BP measuring method in which heartbeat-synchronous signal waves generated from arteries of a living subject are collected while the pressure of an inflatable cuff applied to the arteries is changed, the respective amplitudes of the signal waves are determined to provide a series of wave amplitudes arranged in the order of generation of the signal waves, and a BP value of the subject is determined based on a change of the series of wave amplitudes according to a prescribed software algorithm. An example of the BP measuring method is disclosed in Examined Japanese Patent Application laid open for opposition under Publication No. 2(1990)-25610 assigned to the Assignee of the present U.S. application. The Japanese document discloses a BP measuring apparatus which measures a BP value of a living subject according to the oscillometric BP measuring method, i.e., prescribed software algorithm. The BP measuring apparatus has a display device which displays a series of wave amplitudes in a two-dimensional graph having a first axis indicative of the cuff pressure and a second axis indicative of the wave amplitude. A medical worker such as a doctor can easily recognize, from the distribution of the wave amplitudes with respect to the cuff pressure, the amounts of error of the BP measurement due to external causes such as the physical motion of the subject and the noise produced from peripheral devices. Thus, the doctor can judge whether the conditions of the BP measurement are proper or appropriate. A series of wave amplitudes displayed in the two-dimensional area provided on the display device may define a complex envelope changeable depending upon external factors. There have been employed various smoothening techniques each of which is used to smoothen the envelope of the wave amplitudes obtained in carrying out a BP measurement. The BP measuring method disclosed in Non-Examined Japanese Patent Application laid open for inspection under Publication No. 63(1988)-51837 is one of the smoothening techniques. In this method, an odd number of successive amplitudes are selected from the series of amplitudes, and the amplitude positioned at the center of the selected amplitudes is replaced with the amplitude having the median magnitude. This is the so-called medical filter. By sequentially repeating this median-filter treatment with all the amplitudes by removing the oldest one of the odd number of amplitudes and adding the following amplitude, the envelope of the amplitudes is smoothened. Since a BP measurement is carried out based on the thus smoothened envelope of the amplitudes, the accuracy of measurement of BP values is increased. Although a series of amplitudes are displayed as a two-dimensional graph on the display device, the amplitudes defines only a smoothened envelope wherein the errors of amplitudes due to external factors have been corrected. From a smoothened envelope, a doctor cannot judge whether the conditions of measurement of BP values are proper, unlike a non-smoothened envelope showing the distribution of non-treated "raw" amplitudes from which the doctor can judge.

SUMMARY OF THE INVENTION

It is a first object of the present invention to provide a blood pressure measuring apparatus which enables a patient or a doctor to recognize the time change of the waveforms of pulse waves of the patient and judge whether the patient has a heart disease, when a BP value or values is/are measured on the patient.

The first object has been achieved by the present invention. According to a first aspect of the present invention, there is provided an apparatus for measuring a blood pressure of a living subject, comprising: a blood pressure measuring device which measures a blood pressure value of the subject; a first memory which stores a plurality of blood pressure values measured by the blood pressure measuring device, in an order of measurement of the blood pressure values; a pulse wave detecting device which detects a pulse wave produced from an arterial vessel of the subject in synchronism with heartbeat of the subject while each of the blood pressure values is measured by the blood pressure measuring device; a second memory which stores a waveform of the pulse wave detected by the pulse wave detecting device, in the order, the second memory storing the respective waveforms of the pulse waves each of which is detected by the pulse wave detecting device while a corresponding one of the blood pressure values is measured by the blood pressure measuring device; and an output device which outputs the blood pressure values stored in the first memory, in the order, and a plurality of curves respectively representing the waveforms stored in the second memory, in the order, in a side-by-side relation with each other.

In the BP measuring apparatus in accordance with the first aspect of the invention, the output device outputs the BP values stored in the first memory, in the order of measurement of those BP values, and a plurality of curves representing the waveforms stored in the second memory, in the same order, in a side-by-side relation with each other. The output device may operate in this manner, when the BP apparatus operates for measuring a BP value or values of a living subject such as a patient. Since the BP apparatus is easily used, the patient or a medical worker can easily recognize the time change of the waveforms of the pulse waves of the patient together with the time change of the BP values of the patient. Therefore, the patient or the medical worker can make a diagnosis that the patient may have a heart disease.

In a preferred embodiment in accordance with the first aspect of the invention, the blood pressure measuring device comprises an inflatable cuff adapted to be wound around a body portion of the subject, and the pulse wave detecting device comprises a sensor which detects, as the pulse wave, a pressure oscillation produced in the cuff in synchronism with heartbeat of the subject. In this embodiment, the sensor used as part of the blood pressure measuring device is also used to detect the pulse wave of the patient. Since an exclusive pulse-wave sensor is not needed, the BP apparatus enjoys a simple construction and a low manufacturing cost.

In another embodiment in accordance with the first aspect of the invention, the BP measuring apparatus further comprises amplitude modifying means for modifying an amplitude of each of the waveforms detected by the pulse wave detecting device, so that the waveforms output by the output device have a prescribed amplitude. In this embodiment, the patient or the doctor can easily compare the waveforms of the pulse waves with each other, so that the patient or the doctor can correctly recognize the time change of the waveforms. In this case, the BP measuring apparatus may further comprise wavelength modifying means for modifying a wavelength of the each of the waveforms detected by the pulse wave detecting device, so that the waveforms output by the output device have a prescribed wavelength.

In yet another embodiment in accordance with the first aspect of the invention, the BP measuring apparatus further comprises: evaluating means for evaluating a characteristic of each of the waveforms detected by the pulse wave detecting device, and providing an evaluated value of the each waveform; and a third memory which stores the evaluated value of the each waveform, in the order, wherein the output device outputs the evaluated values stored in the third memory, in the order. In this embodiment, the patient or the doctor can quantitatively figure out the change of the pulse waves, so that the patient or the doctor can more easily recognize the time change of the waveforms of the pulse waves.

In another embodiment in accordance with the first aspect of the invention, the output device comprises means for outputting a first graphical representation indicating the blood pressure values stored in the first memory, and a second graphical representation indicating the evaluated values stored in the third memory, along a common axis indicative of time, and outputting the curves representing the waveforms stored in the second memory, along the common axis. In this embodiment, the BP values, and the evaluated values of the waveforms of the pulse waves are output together with the curves of waveforms along a common "time" axis. The patient or the doctor can more easily recognize the time change of the waveforms.

It is a second object of the present invention to provide an automatic blood pressure measuring apparatus which enables a living body or subject to have a strong visual impression that he or she has a blood pressure abnormality.

The second object has been achieved according to a second aspect of the present invention, which provides an apparatus for measuring a blood pressure of a living subject, comprising: a blood pressure measuring device which measures a blood pressure value of the subject; a first memory which accumulatively stores a plurality of blood pressure values measured by the blood pressure measuring device; a second memory which stores a plurality of pictorial images each of which indicates a corresponding one of a plurality of different evaluations of the blood pressure of the subject; image selecting means for selecting one of the pictorial images which corresponds to a current blood pressure value of the subject measured by the blood pressure measuring device; and an output device which outputs the one pictorial image selected by the image selecting means, together with the blood pressure values stored in the first memory.

In the BP measuring apparatus in accordance with the second aspect of the invention, the output device outputs a pictorial image selected by the image selecting means, together with the BP values stored in the first memory. The pictorial image selected by the image selecting means corresponds to a current BP value of the subject measured by the blood pressure measuring device. Thus, the subject can have a strong visual impression that his or her blood pressure is abnormal, and can keep it in mind for a long time.

In a preferred embodiment in accordance with the second aspect of the invention, the second memory stores a plurality of groups of pictorial images each image of which indicates a corresponding one of a plurality of different evaluations of the blood pressure of the subject, and wherein the apparatus further comprises: a data obtaining device which obtains identification data identifying the subject; and group selecting means for selecting one of the groups of pictorial images which corresponds to the identification data obtained by the data obtaining device, so that the image selecting means selects the one pictorial image from the selected group of pictorial images. In this embodiment, the group selecting means may be adapted to select a group of pictorial images based on the identification data including the personal information of the subject, such as sex, age, and clinical history. Thus, the image selecting means selects a pictorial image which accurately corresponds to a current BP value of the subject measured by the blood pressure measuring device.

In another embodiment in accordance with the second aspect of the invention, the output device comprises a printer which outputs, on a recording sheet, the one pictorial image selected by the image selecting means, together with the blood pressure values stored in the first memory. In this embodiment, the subject can bring the recording sheet on which the selected pictorial image is recorded. Thus, the subject is not required to write down the measured BP values or keep them in mind.

In yet another embodiment in accordance with the second aspect of the invention, the output device comprises means for outputting a graphic representation indicating a time change of the blood pressure values stored in the first memory. In this embodiment, the subject can easily recognize the time change of the BP values.

It is a third object of the present invention to provide an automatic blood pressure measuring apparatus which is easily operable for producing a pictorial image.

The third object has been achieved according to a third aspect of the present invention, which provides an apparatus for measuring a blood pressure of a living subject, comprising: a blood pressure measuring device which measures a blood pressure value of the subject; a first memory which accumulatively stores a plurality of blood pressure values measured by the blood pressure measuring device; a second memory which stores at least one pictorial image; an output device which outputs the pictorial image stored in the second memory, together with the blood pressure values stored in the first memory; an image reading device which reads an original image from an original; an editing device which is operable for editing the original image read by the image reading device; and a registering device which registers the image edited by the editing device, by storing the edited image as the pictorial image in the second memory.

In the BP measuring apparatus in accordance with the third aspect of the invention, the image reading device reads an original image from an original, the editing device is operable for editing the original image, and the registering device registers the edited image, by storing it in the second memory. The output device outputs the edited image, i.e., pictorial image together with the BP values stored in the first memory. The pictorial image accompanying the BP values enable the subject to keep the BP values in mind. In addition, the pictorial image is easily prepared and registered in the present BP measuring apparatus.

In a preferred embodiment in accordance with the third aspect of the invention, the second memory stores a plurality of pictorial images each of which is related to a time of measurement of the blood pressure of the subject, and wherein the apparatus further comprises: a clock device which produces a signal indicative of a time when the blood pressure measuring device measures a blood pressure value of the subject; and image selecting means for selecting one of the pictorial images which corresponds to a time of measurement of a current blood pressure value of the subject measured by the blood pressure measuring device, so that the output device outputs the selected one pictorial image together with the blood pressure values stored in the first memory. In this embodiment, the second memory may be adapted to store pictorial images each related to the date and time of measurement of a BP value of the subject, for example, pictorial images representing flowers at four seasons, landscapes at four seasons, etc. The pictorial image accompanying the measured BP values gives a strong visual impression to the subject, so that the subject can keep the BP values in mind.

In another embodiment in accordance with the third aspect of the invention, the second memory stores a plurality of random selectable pictorial images, and wherein the apparatus further comprises: a random value generator which provides, according to a random function, a random value in response to an operation of the blood pressure measuring device; and image selecting means for selecting one of the pictorial images which corresponds to a random value produced by the random value generator, so that the output device outputs the selected one pictorial image together with the blood pressure values stored in the first memory. In this embodiment, in different BP measurements, different pictorial images may be output together with the BP values of the subject. The different pictorial images help the subject to keep the BP values in mind.

It is a fourth object of the present invention to provide an automatic blood pressure measuring apparatus which provides information related to a medicine to be given to a patient, thereby enabling a medical worker to omit the directions for use of the medicine.

The fourth object has been achieved according to a fourth aspect of the present invention, which provides an apparatus for measuring a blood pressure of a living subject, comprising: a blood pressure measuring device which measures a blood pressure value of the subject; a first memory which accumulatively stores a plurality of blood pressure values measured by the blood pressure measuring device; a second memory which stores a plurality of batches of medicine-related information each of which is related to a corresponding one of a plurality of medicines administrable in treating the blood pressure of the subject; an input device which is operable for specifying one of the medicines; and an output device which selects, from the second memory, one of the batches of medicine-related information which corresponds to the one medicine specified by the input device, and outputs the selected batch of medicine-related information, together with the blood pressure values stored in the first memory.

In the BP measuring apparatus in accordance with the fourth aspect of the invention, the output device selects, from the second memory, one of the batches of medicine-related information which corresponds to the one medicine specified by the input device, and outputs the selected batch of medicine-related information, together with the blood pressure values stored in the first memory. In the case where a doctor gives a BP-treating medicine to a patient after having made a diagnosis based on the measured BP values of the patient, the doctor is just required to specify the medicine through the input device, so that the output device outputs, together with the BP values of the patient, the batch of information related to the medicine, the information including the directions for use of the medicine, the objects of administration of the same, and other necessary items. Thus, the doctor is not required to provide any explanation to the patient.

It is a fifth object of the present invention to provide an apparatus for automatically winding an arm belt around an upper arm of a living subject, in measuring a blood pressure of the subject, wherein the apparatus permits the subject to keep his or her natural posture and ensures that the measurement of BP values is carried out with accuracy.

The fifth object has been achieved according to a fifth aspect of the present invention, which provides an apparatus for winding an arm belt including an inflatable bag, around an upper arm of a living subject, in measuring a blood pressure of the subject, a pressurized air being supplied to the bag to inflate the bag and thereby press the upper arm, the apparatus comprising: an arm receiver inside which the arm belt is provided so as to define a substantially cylindrical space into which the upper arm of the subject is inserted from one of opposite ends of the cylindrical space; a positioning device which changes a position of the arm receiver relative to the upper arm of the subject; a detector which detects a misalignment of a central axis line of the cylindrical space of the arm receiver from a longitudinal axis line of the upper arm of the subject; and a control device which controls, based on the misalignment detected by the detector, the positioning device to change the position of the arm receiver relative to the upper arm so that the central axis line of the cylindrical space of the arm receiver is substantially aligned with the longitudinal axis line of the upper arm.

In the arm-belt winding apparatus in accordance with the fifth aspect of the invention, when the subject inserts his or her upper arm into the arm receiver, the detector detects the misalignment of the central axis line of the arm receiver from the longitudinal axis line of the upper arm of the subject, and the control device controls, based on the misalignment detected by the detector, the positioning device to change the position of the arm receiver relative to the upper arm so that the central axis line of the arm receiver is substantially aligned with the longitudinal axis line of the upper arm. Thus, the present apparatus ensures that the upper arm is suitably inserted such that the arteries of the upper arm are not locally or partially pressed by the belt, without requiring the subject to change his or her posture. That is, the present apparatus ensures that the measurement of BP values is effected with accuracy, permitting the subject to keep his or her natural posture.

It is a sixth object of the present invention to provide a BP monitoring apparatus which monitor the blood pressure of a living subject with high reliability and without giving any burden on the subject.

The sixth object has been achieved according to a sixth aspect of the present invention, which provides an apparatus for monitoring a blood pressure of a living subject, comprising: an inflatable cuff adapted to be wound around a body portion of the subject, the cuff being inflated to provide a pressure to press the body portion; a detector which detects a plurality of pulse amplitudes produced in the cuff being inflated to press the body portion; a pressure changing device which increases the pressure of the cuff to a prescribed value lower than a mean blood pressure of the subject, and subsequently decreases the cuff pressure from the prescribed value, in each of a plurality of periodic cycles; rate-of-change determining means for determining, with respect to the cuff pressure, a rate of change of the pulse amplitudes detected by the detector while the cuff pressure is changed by the pressure changing device; and first abnormality judging means for judging, based on the determined rate of change, whether the blood pressure of the subject is abnormal.

In the blood pressure monitoring apparatus in accordance with the sixth aspect of the invention, the rate-of-change determining means determines, with respect to the cuff pressure, a rate of change of the pulse amplitudes detected by the detector while the cuff pressure is changed by the pressure changing device, and the first abnormality judging means judges, based on the determined rate of change, whether the blood pressure of the subject is abnormal. The BP monitoring of the present apparatus is carried out on the discovery that the rate of change of a low-pressure-side portion of the envelope of the pulse amplitudes with respect to the cuff pressure changes as the blood pressure of the subject changes. Therefore, the reliability of the BP monitoring is improved so much. In addition, since the rate of change of the pulse amplitudes is obtained while the cuff pressure is changed in a low-pressure range between atmospheric pressure and the prescribed low pressure, the subject is free of the burden.

In a preferred embodiment in accordance with the sixth aspect of the invention, the monitoring apparatus further comprises a blood pressure measuring device which automatically measures a blood pressure value of the subject in a series of prescribed steps when the first abnormality judging means judges that the blood pressure of the subject is abnormal. In this embodiment, the BP value of the subject just at the time of finding of the blood pressure abnormality is obtained by the blood pressure measuring device. The thus obtained BP value is clinically important, so that a medical worker such as a doctor can make an appropriate treatment on the subject such as a patient.

In another embodiment in accordance with the sixth aspect of the invention, the first abnormality judging means comprises means for judging whether a pulse amplitude detected by the detector while the cuff pressure is changed by the pressure changing device, is smaller than a reference value, the first abnormality judging means judging that the blood pressure of the subject is abnormal, when the pulse amplitude is smaller than the reference value. Since the envelope of pulse amplitudes obtained from people suffering from low blood pressure because of being in a shock state, is more or less flat with respect to the cuff pressure, it is considerably difficult to identify an abnormally low blood pressure based on the rate of change of the pulse amplitudes with respect to the cuff pressure. In this embodiment, however, since a pulse amplitude is compared with a reference value to identify the blood pressure abnormality, the reliability of identification of the subject's shock state is improved.

In yet another embodiment in accordance with the sixth aspect of the invention, the pressure changing device comprises means for holding the cuff pressure at the prescribed value for a prescribed period of time, and the apparatus further comprises second abnormality judging means for judging, based on a pulse amplitude detected by the detector during the prescribed period, whether the blood pressure of the subject is abnormal. Since the two sorts of abnormality judging means are employed in the present BP monitoring apparatus, the reliability of the BP monitoring is much more improved.

In another embodiment in accordance with the sixth aspect of the invention, the pressure changing device comprises means for increasing and holding the cuff pressure to and at a first prescribed value, and subsequently increasing and holding the cuff pressure to and at a second prescribed value higher than the first prescribed value, and the rate-of-change determining means comprises means for determining, with respect to the cuff pressure, a rate of change of a pulse amplitude detected by the detector when the cuff pressure is held at the second prescribed value from a pulse amplitude detected by the detector when the cuff pressure is held at the first prescribed value. In this embodiment, the rate-of-change determining means determines, with accuracy, the rate of change of a low-pressure-side increasing portion of the envelope of the pulse amplitudes, based on the respective pulse amplitudes detected at the first and second cuff-pressure values. Thus, the reliability of the BP monitoring of the present apparatus is improved. In this case, the rate-of-change determining means may be adapted such that, if at least two successive pulses having substantially the same pulse amplitude are detected while the cuff pressure is held at each of the first and second values, the determining means employs that pulse amplitude in determining the rate of change of the pulse amplitudes. Since in this modified manner "noise" pulses are removed from true pulses, the reliability of the BP monitoring is still more improved.

In another embodiment in accordance with the sixth aspect of the invention, the monitoring apparatus further comprises second abnormality judging means for judging whether the blood pressure of the subject is abnormal, based on a pulse amplitude detected by the detector when the cuff pressure is held at the second prescribed value. In this embodiment, it is not necessary to provide an exclusive cuff-pressure holding period during which to detect a pulse amplitude to be used by the second abnormality judging means for judging whether the subject has blood pressure abnormality.

In another embodiment in accordance with the sixth aspect of the invention, the monitoring apparatus further comprises a blood pressure measuring device which automatically measures a blood pressure value of the subject in a series of prescribed steps when at least one of the first and second abnormality judging means judges that the blood pressure of the subject is abnormal. In this embodiment, when at least one of the first and second abnormality judging means judges that the blood pressure of the subject is abnormal, the blood pressure measuring device automatically measures a blood pressure value of the subject. Thus, the reliability of the BP monitoring is improved so much.

In another embodiment in accordance with the sixth aspect of the invention, the first abnormality judging means comprises means for judging whether the determined rate of change is greater than a reference value, the first abnormality judging means judging that the blood pressure of the subject is abnormal when the determined rate of change is greater than the reference value, and the apparatus further comprises: an input device which is operable for inputting a desired value as the reference value; and changing means for changing, based on the input value as the reference value, the prescribed value to a new value to which the cuff pressure is increased by the pressure changing device. In this embodiment, the cuff pressure applied to the living subject such as a patient is reduced to as low as possible a value.

It is a seventh object of the present invention to provide an automatic blood pressure measuring apparatus which has the function of estimating a BP value of a living subject before an actual BP value of the subject is measured during the decreasing of the cuff pressure.

The seventh object has been achieved by the present invention. According to a seventh aspect of the invention, there is provided an apparatus for automatically measuring a blood pressure of a living subject, comprising: an inflatable cuff adapted to be wound around a body portion of the subject, the cuff being inflated to provide a cuff pressure to press the body portion; a pressure sensor which detects the cuff pressure; a pressure changing device which changes the cuff pressure; a blood pressure measuring device which measures a blood pressure value of the subject by reading the cuff pressure detected by the pressure sensor while the cuff pressure is decreased at a prescribed rate by the pressure changing device; a waveform detector which detects a waveform of a pulse wave produced in the cuff during the decreasing of the cuff pressure, the waveform of the pulse wave being changeable with the cuff pressure; determining means for determining a relationship between (A) evaluated values of a waveform of a pulse wave, (B) pressure values of the cuff, and (C) blood pressure values of the subject, based on (a) an evaluated value of the waveform of the pulse wave detected by the waveform detector, (b) a pressure value of the cuff at a time of detection of the waveform by the waveform detector, and (c) the blood pressure value of the subject measured by the blood pressure measuring device, the relationship being proper to the subject; and estimating means for estimating, according to the determined relationship, a blood pressure value of the subject based on (a') an evaluated value of a waveform of a pulse wave detected by the waveform detector while the cuff pressure is increased before the cuff pressure is decreased at the prescribed rate in measuring an actual blood pressure of the subject and (b') a pressure value of the cuff at a time of detection of the waveform during the increasing of the cuff pressure.

In the automatic BP measuring apparatus in accordance with the seventh aspect of the invention, the estimating means estimates, according to the determined relationship, a BP value of the subject based on (a') an evaluated value of the waveform of at least one pulse of a pulse wave detected by the waveform detector while the cuff pressure is increased before the cuff pressure is decreased and (b') a pressure value of the cuff at the time of detection of the waveform during the increasing of the cuff pressure. Thus, the present apparatus quickly gives a doctor an estimated BP value of the subject, even though the estimated value may be some or less rough.

In a preferred embodiment in accordance with the seventh aspect of the present invention, the BP measuring apparatus further comprises evaluating means for evaluating a plurality of characteristics of the waveform of the pulse wave detected by the waveform detector during the decreasing of the cuff pressure, and providing an evaluated value of each of the waveform characteristics, and the determining means determines a plurality of relationships each based on the evaluated value of a corresponding one of the waveform characteristics and the estimating means calculates a plurality of blood pressure values of the subject according to the determined relationships, respectively, and estimates the blood pressure value of the subject based on the calculated blood pressure values. In this embodiment, since the estimated BP value of the subject is provided based on a variety of BP values determined according to a plurality of sorts of relationships, the reliability of the estimated BP value is increased. The waveform characteristics may comprise at least two selected from the pulse amplitude, Amp-b; the maximum slope of the increasing portion of the waveform, SLOPE; the degree of sharpness of the waveform, %MAP; the percentage of the increasing portion of the waveform to the cyclic period thereof, %IPP; and the percentage of the time difference between the primary and secondary peaks of the waveform to the cyclic period thereof, PI (peak index).

In another embodiment in accordance with the seventh aspect of the present invention, the BP measuring apparatus further comprises target pressure determining means for determining, based on the estimated blood pressure value of the subject, a target pressure value to which the cuff pressure is increased, and the pressure changing device starts decreasing the cuff pressure after the cuff pressure is increased to the target pressure. In this embodiment, the cuff pressure is increased up to the target pressure that may be higher by a prescribed value than an estimated systolic BP value of the subject. Therefore, the cuff pressure is by no means increased up to an unnecessarily high pressure relative to the systolic BP value of the subject, or is by no means re-increased to another target pressure higher than the first or initial target pressure when the first target pressure is not sufficiently high. Thus, the burden to the subject is reduced as such.

In another embodiment in accordance with the seventh aspect of the present invention, the BP measuring apparatus further comprises: abnormality identifying means for identifying a blood pressure abnormality of the subject by comparing the estimated blood pressure value of the subject with a reference value; and an output device which outputs, when the blood pressure abnormality of the subject is identified, information indicative of the identification of the blood pressure abnormality of the subject. In this embodiment, the output device informs a doctor of whether the blood pressure the subject is abnormal, at an early stage when the cuff pressure is increased before being decreased. Thus, the doctor can make a quick decision on whether to give a medical treatment to the subject.

According to an eighth aspect of the present invention, there is provided an apparatus for automatically measuring a blood pressure of a living subject, comprising: an inflatable cuff adapted to be wound around a body portion of the subject, the cuff being inflated to provide a cuff pressure to press the body portion; a pressure sensor which detects the cuff pressure; a pressure changing device which changes the cuff pressure; a blood pressure measuring device which measures a blood pressure value of the subject by reading the cuff pressure detected by the pressure sensor while the cuff pressure is decreased at a prescribed rate by the pressure changing device; a waveform detector which detects a waveform of a pulse wave produced in the cuff during the decreasing of the cuff pressure, the waveform of the pulse wave being changeable with the cuff pressure; a memory which stores a pulse amplitude of the pulse wave detected by the waveform detector, and a pressure value of the cuff at a time of detection of the pulse amplitude; determining means for determining an envelope representing a relationship between (a) a plurality of pulse amplitudes detected by the waveform detector while the cuff pressure is increased before the cuff pressure is decreased at the prescribed rate and (b) a plurality of pressure values of the cuff at respective times of detection of the pulse amplitudes; and estimating means for estimating a blood pressure value of the subject, based on the determined envelope, according to a prescribed relationship.

In the automatic BP measuring apparatus in accordance with the eighth aspect of the invention, the estimating means estimates a BP value of the subject, based on the determined envelope, according to a prescribed relationship between blood pressure and a shape-related characteristic of an envelope. The prescribed relationship is, e.g., such that two cuff-pressure values respectively corresponding to two points on the envelope at which the amplitudes of the envelope significantly largely change, are estimated as the systolic and diastolic BP values of the subject, like the relationship employed in the oscillometric BP determining method. The present apparatus provides a doctor with the estimated BP value of the subject, based on the envelope obtained during the increasing of the cuff pressure before the decreasing of the same. Thus, the doctor quickly obtains an estimated BP value of a patient, even if the estimated value may be some or less rough.

It is an eighth object of the present invention to provide a blood pressure measuring apparatus which determines a blood pressure value of a living subject based on a series of smoothened wave amplitudes and which enables a medical worker to easily judge whether the condition of measurement of BP values is proper or not.

The eight object has been achieved by the present invention. According to a ninth aspect of the invention, there is provided an apparatus for measuring a blood pressure of a living subject, comprising: an inflatable cuff adapted to be wound around a body portion of the subject, the cuff being inflated to provide a cuff pressure to press the body portion; a pressure changing device which changes the cuff pressure; a blood pressure measuring device which (a) obtains a heartbeat-synchronous signal wave generated from arteries of the body portion in synchronism with heartbeat of the subject while the cuff pressure is changed by the pressure changing device, (b) determines respective amplitudes of a plurality of successive pulses of the heartbeat-synchronous signal wave each of which corresponds to one cycle of heartbeat of the subject, and provides, as a first series of determined pulse amplitudes, the determined pulse amplitudes arranged in an order of generation of the corresponding pulses, (c) smoothens the first series of determined pulse amplitudes and thereby provides a second series of smoothened pulse amplitudes, and (d) determines a blood pressure value of the subject based on a change in the second series of smoothened pulse amplitudes; an output device which outputs a two-dimensional representation comprising a number of picture elements; and a control device which controls the output device to output the two-dimensional representation containing the first series of determined pulse amplitudes and the second series of smoothened pulse amplitudes such that one of the first and second series of pulse amplitudes are superimposed on the other series of pulse amplitudes.

In the BP measuring apparatus in accordance with the ninth aspect of the invention, the output device outputs the two-dimensional representation containing the first series of determined pulse amplitudes and the second series of smoothened pulse amplitudes such that one of the first and second series of pulse amplitudes are superimposed on the other series of pulse amplitudes. Therefore, a medical worker such a doctor can visually recognize the differences between the first and second series of pulse amplitudes in the two-dimensional representation. Those differences result from external factors such as the physical motion of the subject or the noise generated from peripheral devices. Based on the total amount of the differences and the respective positions of the differences with respect to the cuff pressure, the doctor can easily judge whether the measured BP value contains a great error due to the external factors, i.e., whether the condition of measurement of the BP value is proper.

According to a tenth aspect of the present invention, there is provided an apparatus for measuring a blood pressure of a living subject, comprising: an inflatable cuff adapted to be wound around a body portion of the subject, the cuff being inflated to provide a cuff pressure to press the body portion; a pressure changing device which changes the cuff pressure; a blood pressure measuring device which (a) obtains a heartbeat-synchronous signal wave generated from arteries of the body portion in synchronism with heartbeat of the subject while the cuff pressure is changed by the pressure changing device, (b) determines respective amplitudes of a plurality of successive pulses of the heartbeat-synchronous signal wave each of which corresponds to one cycle of heartbeat of the subject, and provides, as a first series of determined pulse amplitudes, the determined pulse amplitudes arranged in an order of generation of the corresponding pulses, (c) smoothens the first series of determined pulse amplitudes and thereby provides a second series of smoothened pulse amplitudes, and (d) determines a blood pressure value of the subject based on a change in the second series of smoothened pulse amplitudes; an output device which outputs a degree of propriety of a measurement condition under which the blood pressure value of the subject is determined by the blood pressure measuring device; calculating means for calculating a degree of correction of the second series of smoothened pulse amplitudes from the first series of determined pulse amplitudes, by calculating a ratio of (a) respective differences between (a1) the determined pulse amplitudes corresponding to respective pressure values of the cuff within a prescribed pressure range and (a2) the corresponding smoothened pulse amplitudes, to (b) at least one of the determined pulse amplitudes and the corresponding smoothened pulse amplitudes; and a control device which controls the output device to output the degree of propriety of the measurement condition which corresponds to the degree of correction of the second series of pulse amplitudes calculated by the calculating means.

In the BP measuring apparatus in accordance with the tenth aspect of the invention, the output device outputs the degree of propriety of the measurement condition which corresponds to the degree of correction of the second series of pulse amplitudes calculated by the calculating means. Thus, a medical worker can visually recognize the degree of propriety of the condition of BP measurement. By comparing the degree of correction reflecting the amount of external factors, with a prescribed reference value, the present apparatus may automatically judge whether the measured BP value contains a great error due to the external factors, i.e., whether the condition of measurement of the BP value is proper.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 49(C) is a view explaining a fourth example of the second envelope $H_2$;

DETAILED DESCRIPTION OF THE PREFERRED EMBODIMENTS

Figure 1:
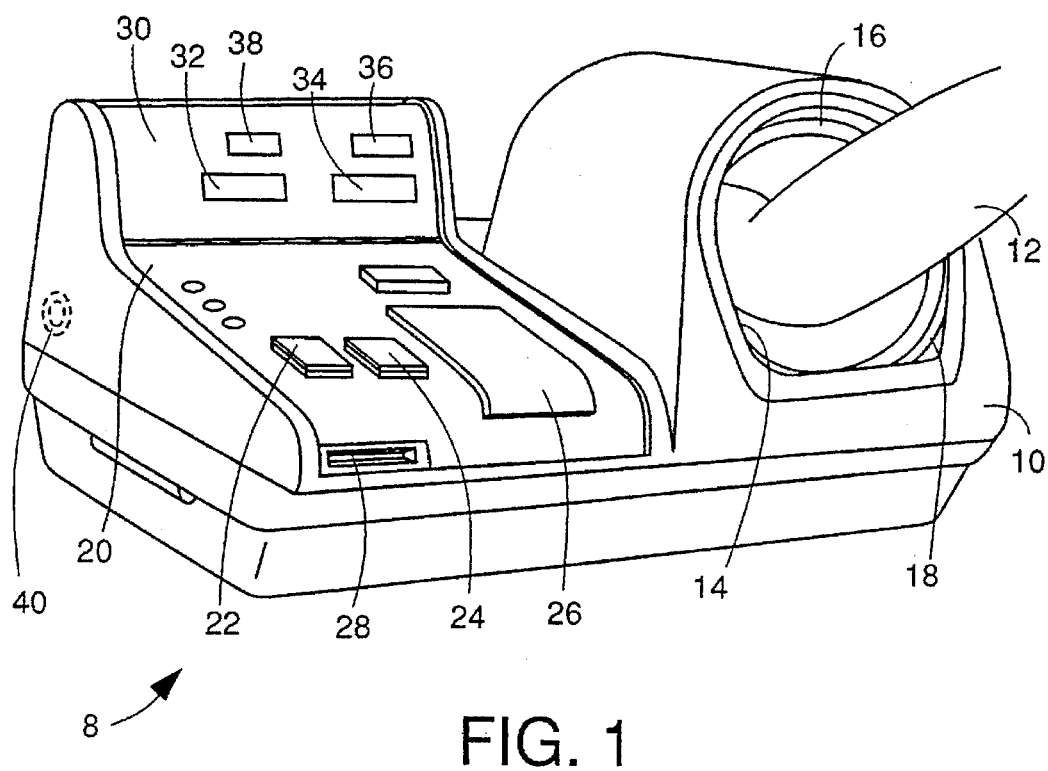
FIG. 1 is a perspective view of a blood pressure (BP) measuring apparatus embodying the present invention.

Referring first to FIG. 1, there is shown an automatic blood pressure (BP) measuring apparatus 8 embodying the present invention. In the figure, reference numeral 10 designates a housing of the BP apparatus 8. The BP apparatus 8 includes a tunnel-like, cylindrical hollow section which serves as an arm receiver 14 into which a living subject such as a patient inserts his or her arm 12 for measurement of his or her blood pressure value. Inside the arm receiver 14, an elongate belt 18 is supported such that the belt 18 takes a generally cylindrical shape. An inflatable cuff 16 constituted by a bag-like flexible cloth and a rubber bag enveloped in the flexible cloth, is secured to the inner surface of the elongate belt 18. The BP apparatus 8 has an operation panel 20 including a START switch 22, a STOP switch 24, a printer 26, and a card insertion slot 28. The BP apparatus 8 also has a display panel 30 including a SAP display 32, a DAP display 34, a PR display 36, and a date and time display 38. The abbreviations 'SAP', 'DAP', and 'PR' represent a systolic and a diastolic blood pressure and a pulse rate, respectively. The BP apparatus 8 has a speaker 40 provided in the side wall thereof. The speaker 40 issues various sound messages.

Figure 2:
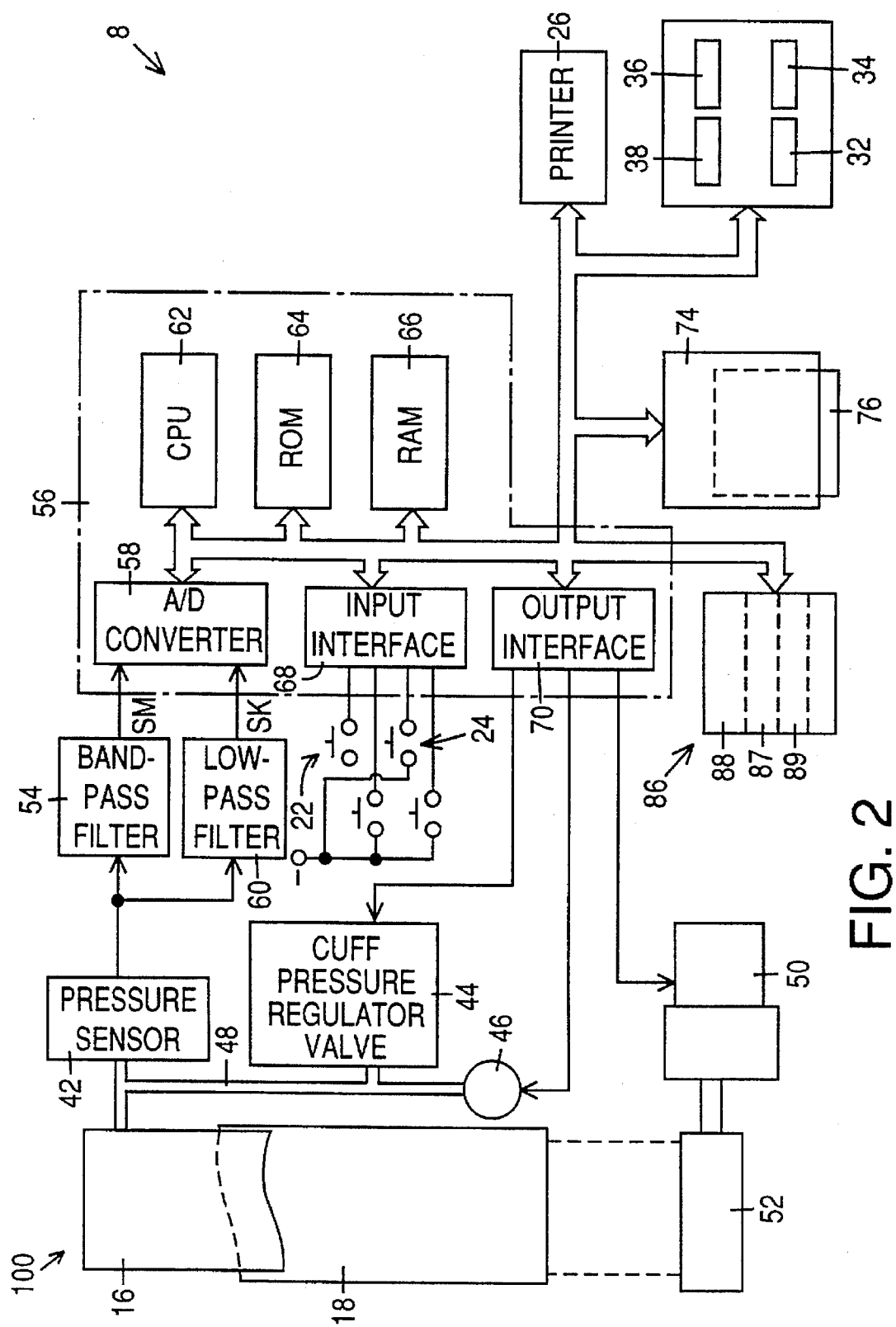
FIG. 2 is a diagrammatic view of the electric arrangement of the apparatus of FIG. 1.

FIG. 2 shows the electric arrangement of the BP apparatus 8. As shown in the figure, the inflatable cuff 16 is connected via piping 48 to a pressure sensor 42, a cuff-pressure regulator valve 44, and an air pump 46. The elongate belt 18, which takes a cylindrical shape in the arm receiver 14 and to which the inflatable cuff 16 is secured, is fixed at one of the longitudinal ends thereof to the housing 10 and is connected at the other longitudinal end to a rotatable drum 52 which is driven or rotated by a direct-current (DC) motor 50 via reduction gears. The elongate belt 18 or inflatable cuff 16 is tightened, and loosened, by the DC motor 50.

The output signal of the pressure sensor 42 is fed to a band-pass filter 54 which selectively transmits a heartbeat-synchronous oscillatory component of the received pressure signal, as a pulse wave signal, SM, to an analog to digital (A/D) converter 58 of an arithmetic and control circuit 56. The pulse wave signal SM represents the pulse wave produced from the pressed arteries of the subject's arm 12 and propagated to the inflatable cuff 16 currently pressing the arm 12. The pressure signal of the pressure sensor 42 is also fed to a low-pass filter 60 which selectively transmits a static component of the received signal, as a cuff pressure signal, SK, to the A/D converter 58 of the control circuit 56. The cuff pressure signal SK represents the change of static pressure of the inflatable cuff 16.

The arithmetic and control circuit 56 is essentially constituted by a microcomputer including a central processing unit (CPU) 62, a read only memory (ROM) 64, a random access memory (RAM) 66, an input interface circuit 68, an output interface circuit 70, and data bus 61. The CPU 62 processes input signals according to the control programs pre-stored in the ROM 64 by utilizing the temporary-storage function of the RAM 66, and produces drive signals and display signals. For blood pressure measurement, the CPU 62 feeds drive signals to the DC motor 50 to tightly wind the inflatable cuff 16 around the upper arm 12 of the living subject being currently inserted in the arm receiver 14, subsequently to the air pump 46 to inflate the cuff 16 and thereby press the upper arm 12, and then to the cuff-pressure regulator valve 44 to gradually reduce the cuff pressure of the cuff 16, so that the CPU 62 receives during reduction of the cuff pressure the pulse wave signal SM and the cuff pressure signal SK from the pressure sensor 42 via the respective filters 54, 60, determines based on the received signals SM, SK the SAP and DAP blood pressure values of the subject in the known oscillometric BP measuring process, feeds display signals to the SAP and DAP displays 32, 34 to indicate the determined SAP and DAP values, respectively, and stores the SAP and DAP values in a blood-pressure (BP) memory area 87 of a memory device 86. The cuff 16, air pump 46, pressure sensor 42, filters 54, 60, and control device 56 cooperate with each other to provide a BP measuring device 100.

The BP memory area 87 of the memory device 86 is capable of storing a number of sets of blood pressure data each of which represents a pair of SAP and DAP values obtained in a corresponding one of a number of blood pressure measurements of the living subject. The memory device 86 also includes a waveform memory area 88. The CPU 62 stores, in the waveform memory area 88, a waveform of the pulse wave signal SM obtained at a prescribed pressure, for example, a mean blood pressure (MAP) value of the subject or a certain pressure lower than the MAP value, in each of the blood pressure measurements of the subject. Furthermore, the memory device 86 includes an evaluated-value (EV) memory area 89. The CPU 62 evaluates a characteristic of each of the waveforms of the pulse wave signal SM stored in the waveform memory area 88, provides an evaluated value of each waveform, and stores in the EV memory area 89 the evaluated value of the waveform in each of the blood pressure measurements of the subject. The memory device 86 may be a well known memory device such as a magnetic disk, magnetic tape, volatile semiconductor memory, or non-volatile semiconductor memory.

In each of blood pressure measurements, the CPU 62 operates the printer 26 to record, on a recording sheet 110 (FIG. 5), graphical representations 116 representing the BP values accumulatively stored in the BP memory area 87 and the waveform evaluated values accumulatively stored in the EV memory area 89. In each blood pressure measurement, the CPU 62 controls the printer 26 to additionally print, on the recording sheet 110, waveform representations 118 including curves 122 representing the waveforms accumulatively stored in the waveform memory area 88, along a time axis 124 identical with a common time axis 120 of the graphs 116.

The BP memory area 87 of the memory device 86 stores a number of pairs of SAP and DAP values of the living subject that are measured using the inflatable cuff 16, air pump 46, pressure sensor 42, etc. The band-pass filter 54 provides the pulse wave signal SM representing the pulse wave produced from the arteries of the arm 12 of the subject in synchronism with the heartbeats of the subject while the cuff pressure of the cuff 16 is gradually decreased in each blood pressure measurement. The waveform memory area 88 stores the waveform of the pulse wave signal SM provided by the band-pass filter 54, in each blood pressure measurement. The printer 26 outputs the BP values accumulatively stored in the BP memory area 87, in the order of measurement of those BP values, and outputs the curves 122 representing the waveforms accumulatively stored in the waveform memory area 88, in the order of storage of those waveforms and in parallel to the BP values. Thus, the present BP apparatus 8 is very easy to use, and outputs the BP values and waveforms of the living subject in a side-by-side relation with each other. Medical workers can read the change of the waveforms in relation with the change of the BP values, and can make a diagnosis on whether the subject has a heart disease.

Figure 3:
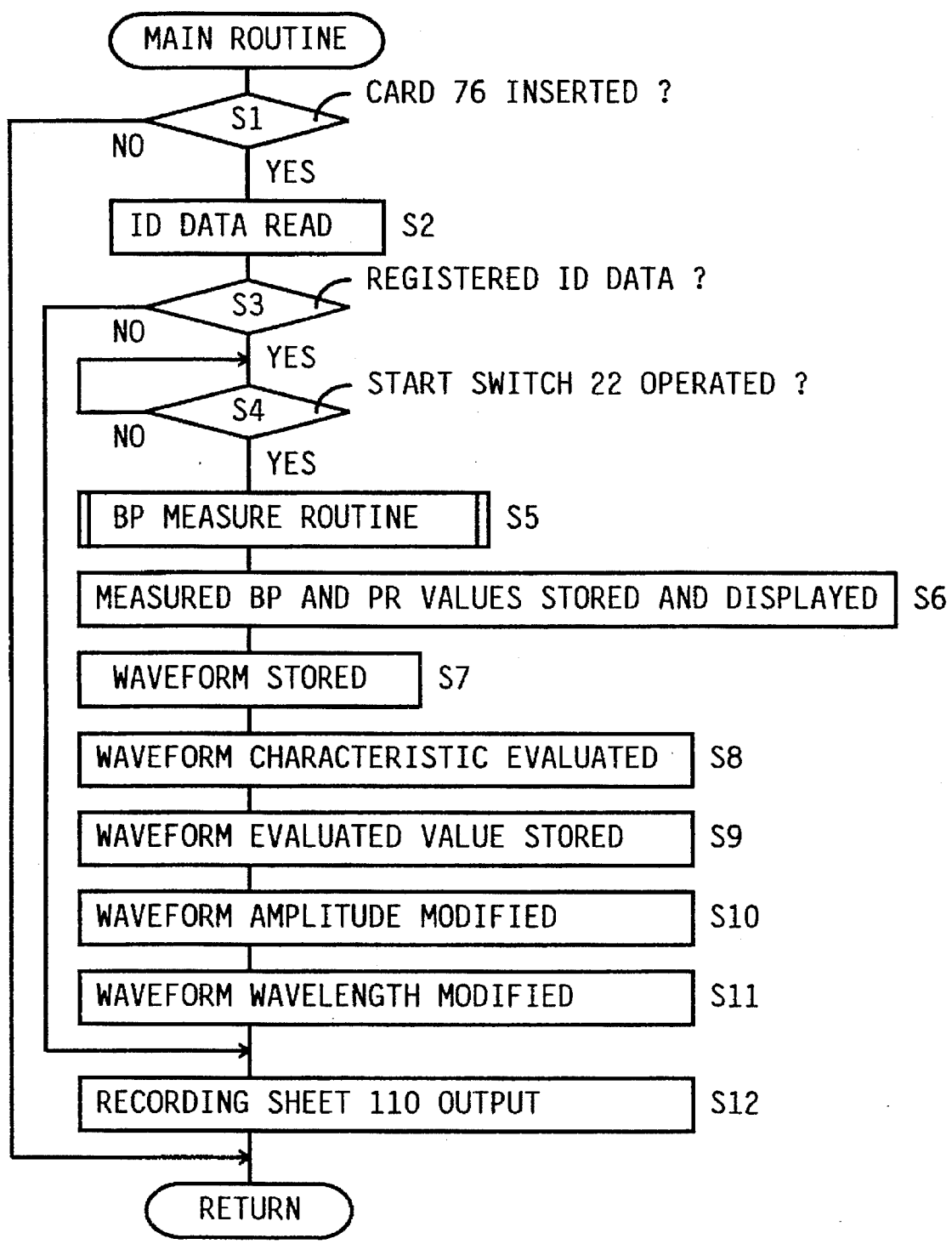
FIG. 3 is a flow chart representing a control program according to which the apparatus of FIG. 1 operates.

The ROM 64 stores a control program represented by a flow chart shown in FIG. 3. The flow chart includes Step S10 at which the CPU 62 processes or modifies the waveforms of the pulse wave signals SM stored in the waveform memory area 88 of the memory device 86, so that the respective amplitudes of the modified waveforms are equal to one another and the thus modified waveforms are output on the recording sheet 110 by the printer 26. Thus, medical workers can compare the waveforms with one another and recognize the time change of the waveforms.

The flow chart of FIG. 3 also includes Step S11 at which the CPU 62 processes or modifies the waveforms of the pulse wave signals SM stored in the waveform memory area 88, so that the respective wavelengths of the modified waveforms are equal to one another and the thus modified waveforms are output on the recording sheet 110 by the printer 26. Thus, medical workers can compare the waveforms with one another and recognize the time change of the waveforms.

The flow chart of FIG. 3 further includes Step S8 at which the CPU 62 evaluates a characteristic of each of the waveforms accumulatively stored in the waveform memory area 88, provides an evaluated value of the characteristic of each waveform and stores, in the EV memory area 89, the evaluated value of each waveform. The printer 26 outputs the respective evaluated values of the waveforms that have accumulatively been stored in the EV memory area 89, in the order of storage of the waveforms in the waveform memory area 88. Thus, medical workers can quantitatively understand the time change of the pulse wave signals SM and can easily recognize the time change of the respective waveforms of the pulse wave signals SM.

The printer 26 outputs the respective graphs 116 of (a) the BP values accumulatively stored in the BP memory area 87 and (b) the waveform evaluated values accumulatively stored in the EV memory area 89, each along the common time axis 120. In addition, the printer 26 outputs the curves 122 representing the waveforms accumulatively stored in the waveform memory area 88, in parallel with the above two graphs, along the identical time axis 124. That is, the printer 26 outputs the BP values and the waveform evaluated values, together with the corresponding waveform curves, along the common time axis. Thus, medical workers can easily recognize the time change of the waveforms of the pulse waves of the living subject.

The CPU 62 is connected to a card reader 74 which receives a magnetic card 76 being inserted in the card slot 28 by the living subject and read identification (ID) data recorded on the magnetic card 76. The ID data recorded on the magnetic card 76 identifies the living subject carrying the magnetic card 76.

Hereinafter, there will be described the operation of the present automatic BP measuring apparatus 8 constructed as described above, by reference to the flow chart of FIG. 3.

First, at Step S1, the CPU 62 judges whether a magnetic card 76 has been inserted in the card reader 74 through the card slot 28. If a negative judgment is made at Step S1, the current control cycle of this routine is ended. On the other hand, if a positive judgment is made, i.e., if a magnetic card 76 has been inserted, the control of the CPU 62 proceeds with Step S2 to read the ID data magnetically recorded on the magnetic card 76. The magnetic card 76 may be a product according to Japanese Industrial Standard, X6301 or X6302.

Step S2 is followed by Step S3 to judge whether the ID data read from the magnetic card 76 has been registered in the BP apparatus 8, i.e., is identical with any of the sets of ID data stored in an ID data memory area (not shown) of the memory device 86. If a negative judgment is made at Step S3, the control goes to Step S12 at which the CPU 62 controls the printer 26 to output, on a recording sheet 110, a message indicating that the ID data recorded on the magnetic card 76 has not been registered on the BP apparatus 8 and that you are requested to register your magnetic card 76 on the BP apparatus 8. In addition, the CPU 62 controls the card reader 74 to eject the non-registered card 76.

On the other hand, if a positive judgment is made at Step S3, the control of the CPU 62 goes to Step S4 to judge whether the START switch 22 has been operated to start a blood pressure (BP) measurement. The CPU 62 repeats Step S4 until a positive judgment is made. If a positive judgment is made at Step S4, the control goes to Step S5, i.e., BP measure subroutine in which a systolic (SAP), a diastolic (DAP), and a mean blood pressure (MAP), and a pulse rate (PR) value, of the living subject are measured or determined. In the BP measure subroutine, the CPU 62 operates, according to a pre-stored algorithm, for automatically increasing the cuff pressure of the inflatable cuff 16 and determining during the reduction of the cuff pressure the SAP, DAP, and MAP values of the living subject in the known oscillometric BP measuring method. Specifically, the SAP and DAP values are determined based on the change of respective amplitudes of pulses of the pulse wave signal SM obtained during the reduction of the cuff pressure. The MAP value is determined as being equal to a cuff pressure at the time of occurrence of a pulse having a maximum amplitude. The PR value is determined based on a time difference between two successive pulses of the pulse wave signal SM, i.e., pulse wave represented by the signal SM.

Step S5 is followed by Step S6 to store, in the BP memory area 87 of the memory device 86, data indicative of the SAP, DAP, MAP and PR values determined at Step S5, together with data indicative of the date and time of measurement of those values, in relation with the ID data identifying the magnetic card 76 being currently inserted in the card reader 74 and thereby identifying the living subject carrying the card 76. Additionally, the CPU 62 commands the SAP, DAP, and PR displays 32, 34, 36 to display the determined SAP, DAP, and PR values, respectively.

At the following Step S7, the CPU 62 stores, in the waveform memory area 88, the waveform of one of the pulses of the pulse wave signal SM which one pulse has been detected at a prescribed cuff pressure, or in a prescribed range of the cuff pressure, during the reduction of the cuff pressure. The waveform of one pulse is stored together with data indicative of the date of detection of the pulse wave signal SM, both in relation with the ID data identifying the living subject carrying the ID card 76. The prescribed cuff pressure at which the waveform is detected or obtained may be selected at around the MAP value of the subject, or at a pressure lower than the MAP value, or at the lowest possible pressure in a pressure range between the MAP and DAP values of the subject. For example, the CPU 62 selects, from all the pulses obtained between the MAP and DIA values, one pulse obtained at the lowest pressure of all the pressures at which the respective pulses are obtained. The CPU 62 stores the waveform of the thus selected one pulse in the waveform memory 86. To this end, the CPU 62 utilizes the pulse wave signal SM supplied from the band-pass filter 54.

Figure 4:
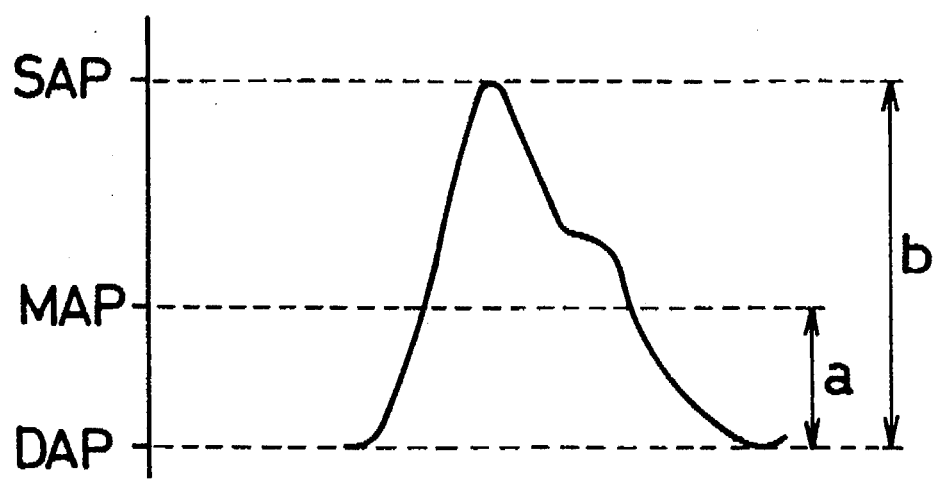
FIG. 4 is a view illustrating an evaluated value, %MAP, representing a characteristic of the waveform of pulse wave, the value %MAP being determined at Step S8 of FIG. 3.

Step S7 is followed by Step S8 to evaluate a characteristic of the waveform of one pulse SM stored in the waveform memory area 88, and provide an evaluated value of the waveform characteristic of one pulse SM. The evaluate value may be one or both of (a) a slope value, SLOPE, related to an increasing portion of one pulse starting from a lower peak to a following upper peak of the signal SM, and (b) an MAP percentage value, %MAP, related to a decreasing portion of one pulse starting from an upper peak to a following lower peak of the signal SM. The value SLOPE is defined as the greatest slope, $(dP/dt)_{max}$, of the increasing portion of one pulse SM. The value %MAP is defined as the percentage (=100×a/b) of the MAP value (i.e., height, a, of the MAP value shown in FIG. 4) with respect to the amplitude, b, of one pulse SM (b is the pressure difference between the SAP and DAP values). The value SLOPE reflects the strength of the heart muscle of the living subject, and relates to the amount of output of the heart of the subject. The value %MAP relates to the diastolic period of the heart of the subject, i.e., resistance of the peripheral arterial vessels of the subject.

At the following Step S9, the CPU 62 stores, in the EV memory area 89, the waveform characteristic evaluated values determined at Step S8, i.e., the two values SLOPE, %MAP, with the date of detection of the pulse wave signal SM, in relation with the ID data identifying the living subject. Step S9 is followed by Step S10 to modify the one-pulse waveform stored in the waveform memory area 88 so that the modified waveform takes a prescribed amplitude, i.e., prescribed difference between the upper and lower peaks of the waveform. Since amplitudes of waveforms easily change depending upon the cuff pressures at which the waveforms are obtained through the cuff 16, the amplitude modification of the waveforms at Step S10 ensures that the waveforms are clearly output in parallel with one another on the recording sheet 110 and that medical workers easily compare those waveforms with one another.

At the following Step S11, the CPU 62 modifies the one-pulse waveform whose amplitude has been modified at Step S10, so that the modified waveform takes a prescribed wavelength, i.e., prescribed time length between the two successive lower peaks of the waveform. Since wavelengths of waveforms easily change depending upon the pulse rates at which the waveforms are obtained through the cuff 16, the wavelength modification of the waveforms at Step S11 ensures that the waveforms are clearly output in parallel with one another on the recording sheet 110 and that medical workers easily compare those waveforms with one another.

Figure 5:
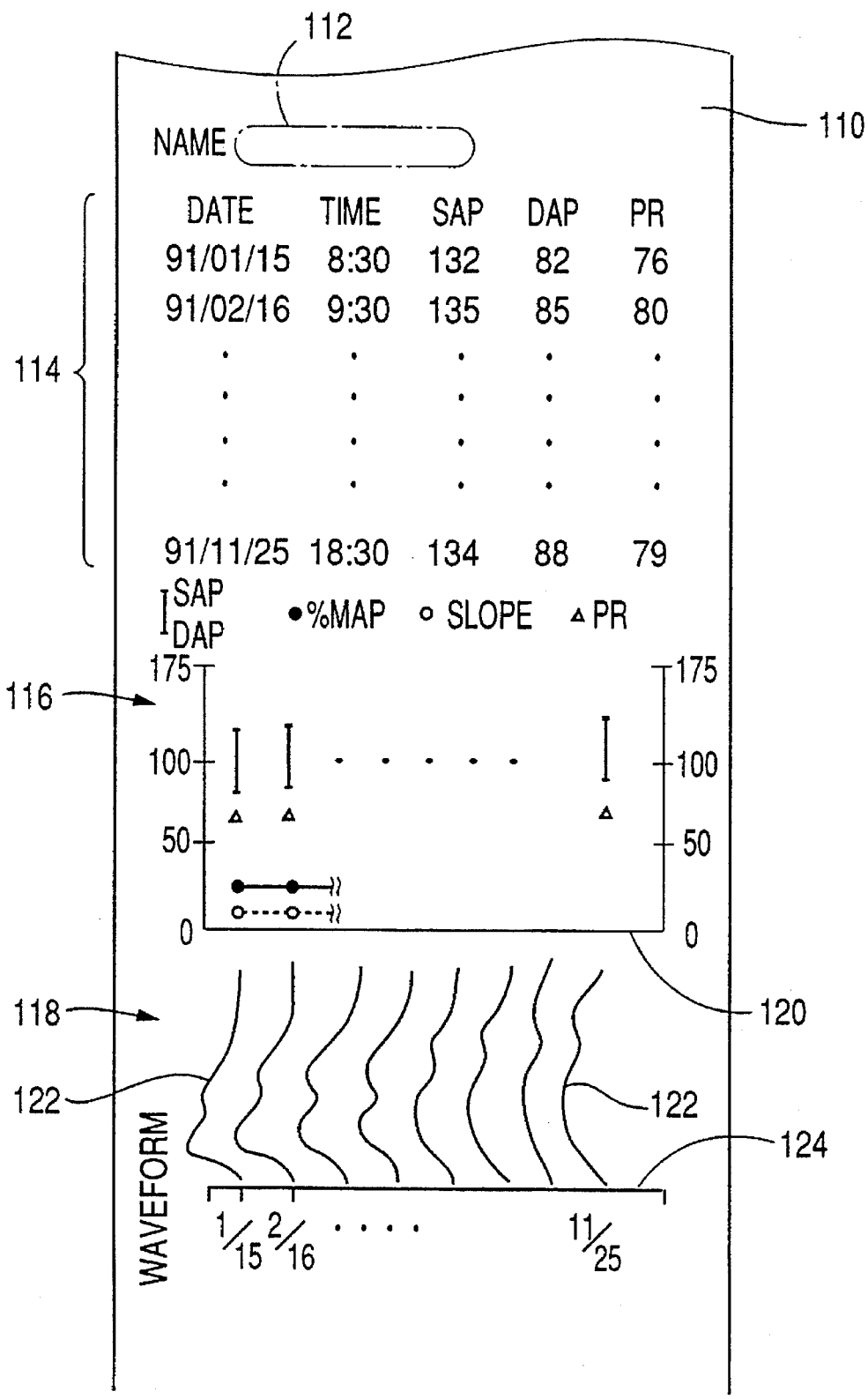
FIG. 5 is a view of a printed output of the apparatus of FIG. 1 as a result of an operation of the same according to the flow chart of FIG. 3.

Step S11 is followed by Step S12 to control the printer 26 to output or record, on the recording sheet 110 shown in FIG. 5, the BP and PR data which have accumulatively been stored in the memory device 86 in relation with the ID data read from the magnetic card 76. Specifically, in a left-hand and upper portion of the sheet 110, the printer 26 records a name 112 of the living subject identified by the ID data. Beneath the name 112, the printer 26 records (a) a data list 114 including the dates and times of measurement and the measured SAP, DAP, and RP values; (b) graphic representations 116 of various parameters; and (c) waveform representations 118. The graphic representations 116 include (b1) a series of bars the upper and lower ends of each of which represent an SAP and a DAP blood pressure value, (b2) a series of symbols, △, each of which represents a PR value, (b3) a series of symbols, ○, each of which represents a value SLOPE, and (b4) a series of symbols, •, each of which represents a value %MAP, all in relation with corresponding times of measurement, along the common axis of abscissae, i.e., first time axis 120. The waveform representations 118 include a series of curves 122 representing the waveforms accumulatively stored in the waveform memory area 88, each in relation with the time of measurement of corresponding BP values, along the first time axis 120 and the second time axis 124 identical with the first time axis 120.

As is apparent from the foregoing description of the first embodiment, the band-pass filter 54 of the BP apparatus 8 provides a pulse wave signal SM representing a pulse wave produced from arteries of a living subject in synchronism with the heartbeats of the subject while each blood pressure measurement is carried out on the subject at Step S5 of FIG. 3. The waveform of one pulse of the pulse wave signal SM provided by the band-pass filter 54 is accumulatively stored in the waveform memory area 88 at Step S7. At Step S12, the printer 26 outputs (a) the BP values accumulatively stored in the BP memory area 87, in the order of measurement, on the recording sheet 110, and (b) the curves 122 representing the waveforms accumulatively stored in the waveform memory area 88, in the order of storage, in parallel with the BP values, both along the common time axis 120. The BP measuring apparatus 8 is very easy to operate and simultaneously outputs the BP values and waveforms of a living subject in parallel with each other. Medical workers can easily recognize a time change of the waveforms in relation with a time change of the BP values, and can make a diagnosis on whether the subject has a heart disease or not.

In the first embodiment, the band-pass filter 54 is primarily employed for extracting, as a pulse wave signal SM, a pressure oscillation produced in the cuff 16 in synchronism with the heartbeats of a living subject in a blood pressure measurement, and the CPU 62 is programmed to utilize the waveform of the pulse wave signal SM provided by the band-pass filter 54. Thus, the BP apparatus 8 does not require an exclusive sensor for detecting a pulse wave from the subject, and enjoys a simpler construction and a lower manufacturing cost.

In the first embodiment, the CPU 62 modifies, at Step S10 of FIG. 3, each waveform stored in the waveform memory area 88, in such a way that each modified waveform has a prescribed amplitude, and the printer 26 outputs at Step S12 the modified waveforms each having the prescribed amplitude. Thus, medical workers can easily compare the output waveforms with one another and recognize a time change of the waveforms.

Also, in the first embodiment, the CPU 62 modifies, at Step S11, each waveform stored in the waveform memory area 88, in such a way that each modified waveform has a prescribed wavelength, and the printer 26 outputs at Step S12 the thus modified waveforms each having the prescribed wavelength. Thus, medical workers can easily compare the output waveforms with one another and recognize a time change of the waveforms.

Moreover, in the first embodiment, the CPU 62 evaluates, at Step S8, a characteristic of each waveform stored in the waveform memory area 88, provides an evaluated value of each waveform, and stores the waveform evaluated value in the EV memory area 89. At Step S12, the printer 26 outputs the waveform evaluated values accumulatively stored in the EV memory area 89, in the order of evaluation, i.e., in the order of detection of waveform. Thus, medical workers can recognize a quantitative change of the waveforms and more easily recognize a time change of the waveforms.

Furthermore, in the first embodiment, the printer 26 outputs, in the graphs 116, the BP values accumulatively stored in the BP memory area 87, and the waveform evaluated values accumulatively stored in the EV memory area 89, along the common first time axis 120. Simultaneously, the printer 26 outputs the curves 122 corresponding to the waveforms accumulatively stored in the waveform memory area 88, in parallel with the graphs 116, along the first or second time axis 120, 124. Thus, medical workers can still more easily recognize a time change of the waveforms.

Figure 6:
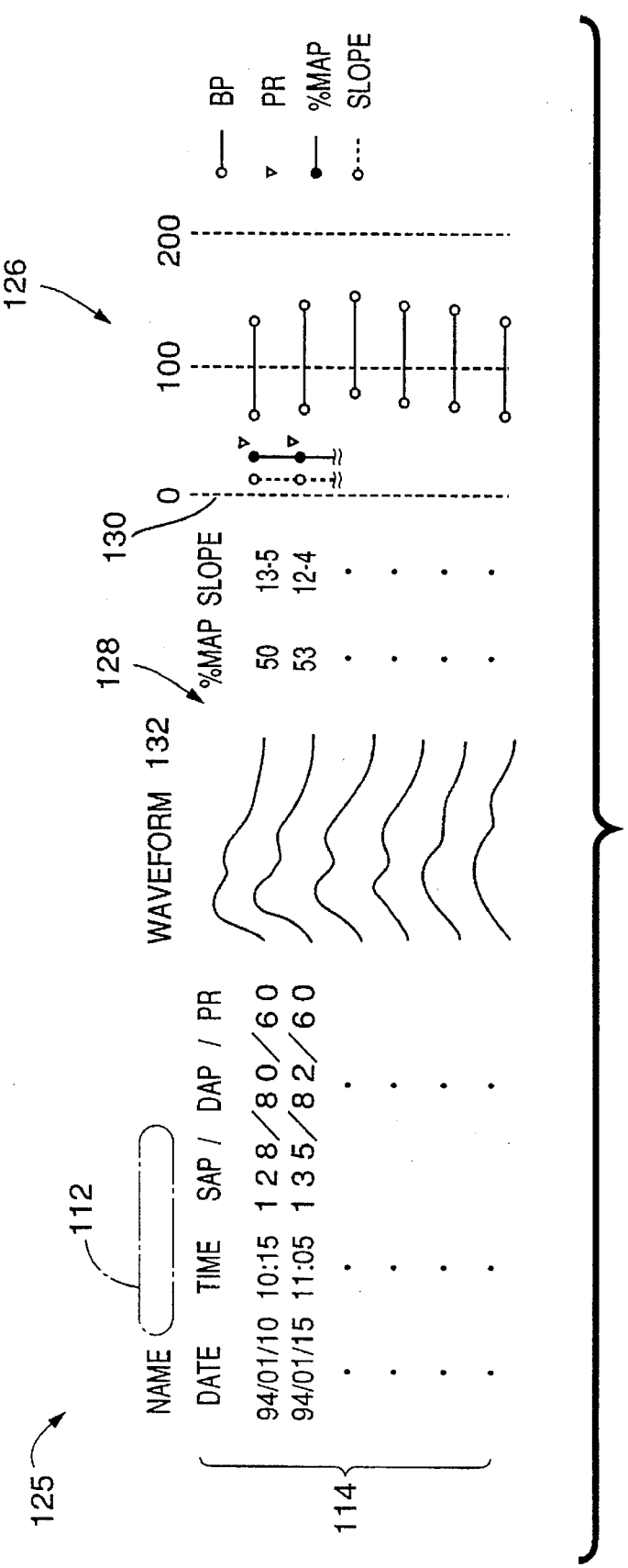
FIG. 6 is a view of a printed output of another BP measuring apparatus obtained by modifying the apparatus of FIG. 1.

The BP apparatus 8 or the printer 26 may be modified to record, at Step S12, measurement data 112, 114, 126, 128 on a recording sheet 125 as shown in FIG. 6. The recording sheet 125 has a width greater than that of the recording sheet 110 shown in FIG. 5. Alternatively, the BP apparatus 8 may further include a display device, such as a cathode ray tube (CRT), for displaying the same visual representation as that recorded on the recording sheet 125 of FIG. 6. In a left-hand and upper portion of the recording sheet 125, the printer 26 records a name 112 of a living subject identified by the ID data read from a magnetic card 76. The printer 26 records, beneath the name 112, a data list 114 including dates and times of measurement and measured SAP, DAP, and RP values; and, on the right-hand side of the data list 114, graphic representations 126 of various parameters, and waveform representations 128. The graphic representations 126 show a series of bars the right and left ends of each of which represent an SAP and a DAP value (mmHg), a series of symbols, ▽, each of which represents a PR value, a series of symbols, ○, each of which represents a value SLOPE, and a series of symbols, ●, each of which represents a value %MAP, all in relation with corresponding times of measurement, along a common axis of ordinates, i.e., time axis 130. The waveform representations 128 include a series of curves 132 representing the waveforms accumulatively stored in the waveform memory area 88, each in relation with the time of measurement of corresponding BP values, along the time axis 130. The time axis 130 need not be explicitly indicated on the recording sheet 125, but may be provided implicitly, without any indication thereof, on the sheet 125. Between the waveforms 128 and the graphs 126, the recording sheet 125 shows a series of values %MAP and a series of values SLOPE. The left-hand value "13" of, e.g., a measurement result "13-5" of the SLOPEs represents a maximum slope of the increasing portion of one pulse, whereas the right-hand value "5" represents a maximum slope of the decreasing portion of the same pulse.

Figure 7:
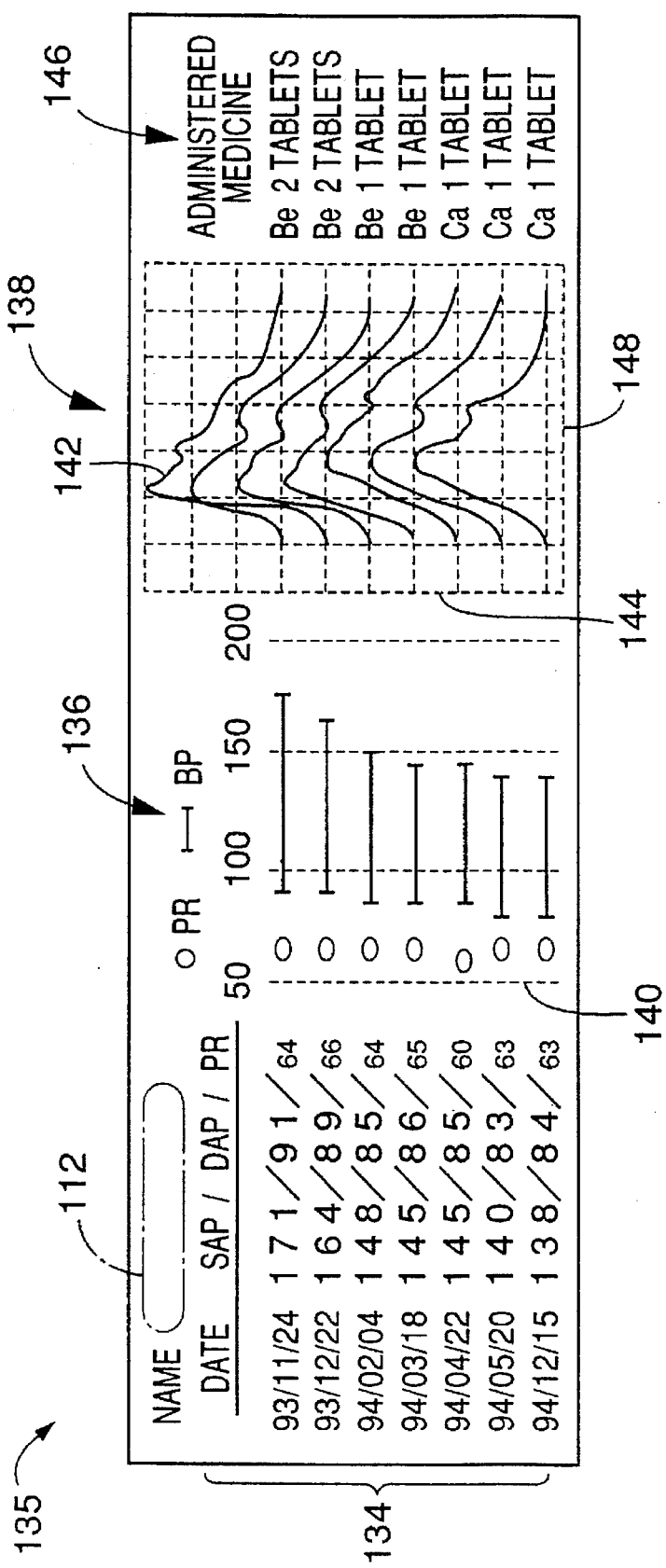
FIG. 7 is a view of a printed output of yet another BP measuring apparatus obtained by modifying the apparatus of FIG. 1.

Otherwise, the BP apparatus 8 or the printer 26 may be modified to record, at Step S12, measurement data 112, 134, 136, 138 on a recording sheet 135 as shown in FIG. 7. In a left-hand and upper portion of the recording sheet 135, the printer 26 records a name 112 of a living subject identified by the ID data read from a magnetic card 76. The printer 26 records, beneath the name 112, a data list 134 including dates and times of measurements and measured SAP, DAP, and RP values; and, on the right-hand side of the data list 134, graphic representations 136 of various parameters, waveform representations 138, and names 146 of administered medicines. The graphic representations 136 show a series of bars the right and left ends of each of which represent a SAP and a DAP blood pressure value (mmHg), and a series of symbols, o, each of which represents a PR value, all in relation with corresponding times of measurements, along a common axis of ordinates, i.e., time axis 140. The waveform representations 138 include, in a ruled area 148, a series of curves 142 representing the waveforms accumulatively stored in the waveform memory area 88, each in relation with the time of measurement of corresponding SAP and DAP values, along a time axis 144 as one side of the ruled area 148 and additionally along the time axis 140. The names of administered medicines 146 indicate the medicines administered to the living subject when blood pressure measurements are carried out on the subject. Data representing the medicine names 146 may be input to the BP apparatus 8 through operation of a keyboard (not shown) connected to the apparatus 8, or may be transmitted from a host computer (not shown) which processes medical information on the living subject. The medicine data may be input or transmitted to the control circuit 56 of the BP apparatus 8 before Step S4 of FIG. 3.

Since the medicine names 146 are indicated together with the graphs 136 and waveforms 138, medical workers can recognize the time changes of medical effects of the medicines administered to the subject to treat the subject's heart disease. The rules 148 are provided for enabling the medical workers to more easily read the time change of the waveforms 142. However, the rules 148 may be omitted. In the data list 134, the size of the figures representing the PR values are smaller than that of the figures representing the BP values, for preventing any confusion of the BP and PR values. However, the BP and RP values may be recorded in the same size.

It is to be understood that in the first embodiment the BP apparatus 8 may be modified in various manners.

In the first embodiment relating to the BP apparatus 8, it is possible to omit all steps, or one or more specific steps, out of Steps S8 through S11 of the flow chart of FIG. 3.

In the flow chart of FIG. 3, it is possible to carry out Steps S10 and S11 before Step S7. In this case, at Step S7, the CPU 62 stores, in the waveform memory area 88, the waveforms which had been modified with respect to the amplitudes and wavelengths thereof at Steps S10 and S11.

At Step S5 of FIG. 3, the CPU 62 determines BP values according to the known oscillometric method. However, the BP apparatus 8 may be modified to measure BP values of a living subject according to the known Korotkoff-sound method where one or more BP values are determined based on detected Korotkoff sounds. In this case, the BP apparatus 8 is provided with a microphone which detects Korotkoff sounds produced from arteries of a body portion (e.g., upper arm) of a living subject while the cuff pressure pressing the upper arm is changed, i.e., gradually decreased or increased.

The automatic BP measuring apparatus 8 starts measuring BP values of a living subject if ID data recorded on a magnetic card 76 being inserted therein by the subject is found to be identical with ID data already registered in the apparatus 8. However, the principle of the present invention is applicable to other types of BP measuring apparatus, for example, apparatus which continuously repeats BP measurements of a living subject at regular intervals of time (e.g., at a prescribed interval of 5 to 30 minutes) by using an inflatable cuff being wound around a body portion of the subject. In this case, the apparatus may have a display device (e.g., CRT) which displays the repetitively measured BP values, and the waveforms obtained therewith, along a common time axis.

Figure 8:
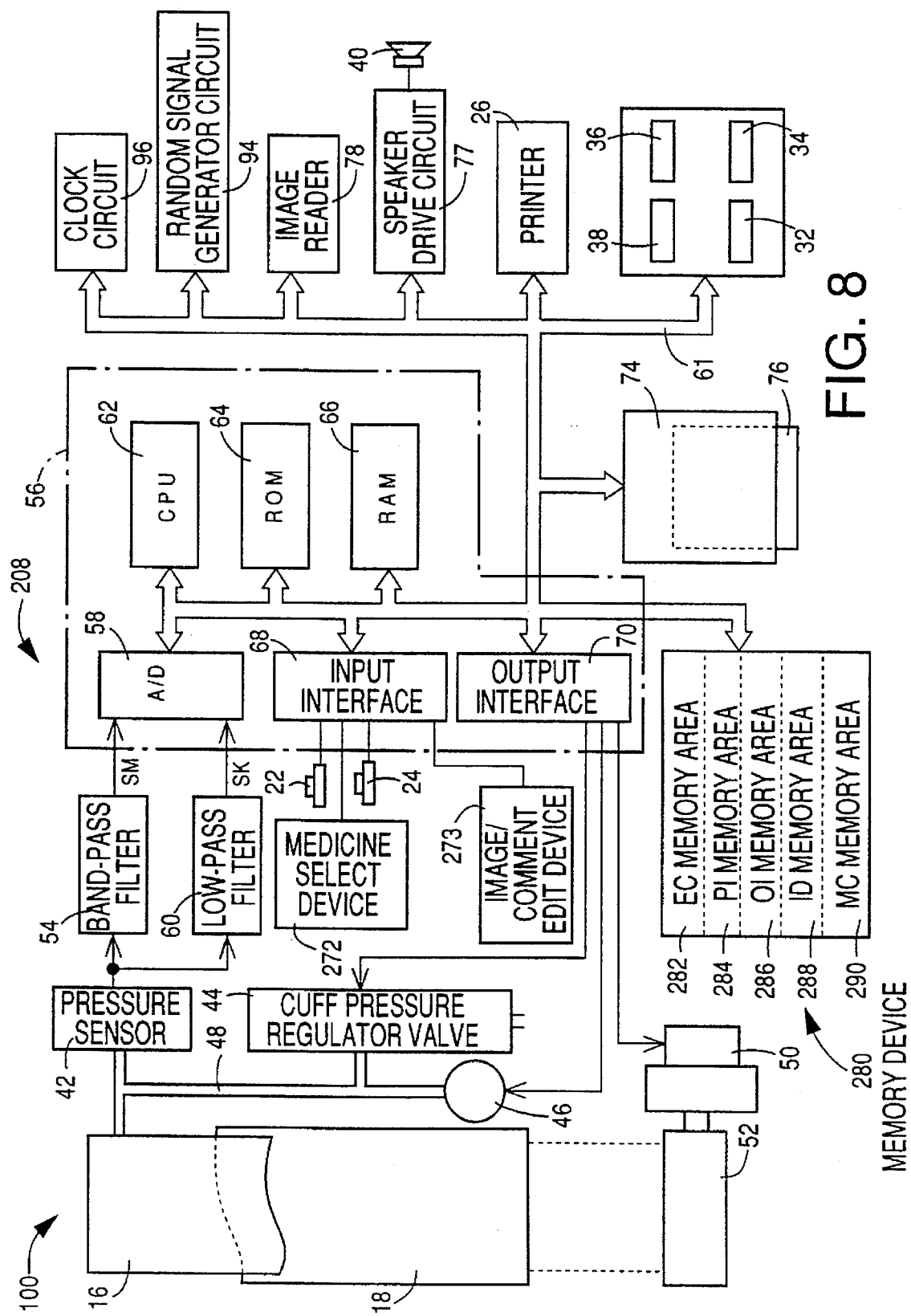
FIG. 8 is a diagrammatic view corresponding to FIG. 2, showing the electric arrangement of a BP measuring apparatus as a second embodiment of the present invention.

Next, there will be described a second embodiment of the present invention. The second embodiment relates a blood pressure (BP) measuring apparatus 208 having an electric arrangement shown in FIG. 8. The BP measuring apparatus 208 is similar to the BP measuring apparatus 8 shown in FIGS. 1 and 2. Therefore, the same reference numerals as used in FIGS. 1 and 2 are used to designate corresponding elements or parts of the BP apparatus 208, and the description of those elements or parts is omitted. The following description will be focused on the differences of the BP apparatus 208 from the BP apparatus 8.

In the blood pressure and pulse rate (PR) measuring process, the BP apparatus 208 operates similar to the BP apparatus 8. Specifically, a CPU 62 of an arithmetic and control device 56 feeds drive signals to a DC motor 50, subsequently to an air pump 46, and then to a cuff-pressure regulator valve 44, so that the CPU 62 receives a pulse wave signal SM and a cuff pressure signal SK from a pressure sensor 42 via respective filters 54, 60, determines based on the received signals SM, SK the BP and PR values of a living subject 12 such as a patient according to known algorithms pre-stored in the ROM 64, feeds display signals to an SAP, a DAP, and a PR display 32, 34, 36 to display the measured BP and PR values, and generates print signals to a printer 26 to record the measured values on recording sheets 292a, 292b, and 292c respectively shown in FIGS. 10, 11, and 12.

In the present embodiment, the CPU 62 accumulatively stores the measured BP and PR values of the subject 12, in a physical-information (PI) memory area 284 of a memory device 280 connected to the control device 56. The memory device 280 may be constituted by a magnetic disk, a magnetic tape, or a semiconductor memory.

The control device 56 or CPU 62 is connected to a speaker drive circuit 277 which supplies drive signals to a speaker 40 to generate sounds or voices such as messages to the subject 12 or medical workers. The CPU 62 is also connected to a known image reader 278 which reads images from an original bearing an original image.

The memory device 280 includes an evaluation-comment (EC) memory area 282 in which are pre-stored a plurality of sets of evaluation-comment data each of which is indicative of a corresponding one of a plurality of predetermined BP evaluation comments relating to the blood pressure of the subject 12, or the time change of the BP values accumulatively stored in the PI memory area 284. The CPU 62 selects, according to the control programs pre-stored in the ROM 64, one of the stored evaluation comments which corresponds to the BP values of the subject 12 measured by a BP measuring device 100 in a current operation cycle, and/or the collected BP values of the subject 12 measured by the BP device 100 and accumulatively stored in the PI memory area 284. The collected BP values of the subject 12 contain the BP values obtained by the BP device 100 in the current operation cycle and the BP values obtained by the BP device 100 in the prior operation cycles. The CPU 62 supplies sound signals to the speaker drive circuit 278 to drive the speaker 40 and thereby issue the selected one evaluation comment.

The memory device 280 further includes an output-image (OI) memory area 286 in which are pre-stored a plurality of sets of evaluation-image data each of which is representative of a corresponding one of a plurality of predetermined BP evaluation pictorial images relating to the blood pressure of the subject 12, or the time change of the BP values accumulatively stored in the PI memory area 284. The CPU 62 selects, according to the control programs pre-stored in the ROM 64, one of the stored evaluation images which corresponds to the BP values of the subject 12 measured by a BP measuring device 100 in a current operation cycle, and/or the collected BP values of the subject 12 measured by the BP device 100 and accumulatively stored in the PI memory area 284. The CPU 62 supplies print signals to the printer 26 to record the selected one evaluation image on the recording sheet 292a, 292b, 292c.

The memory device 280 additionally includes an identification (ID) data memory area 288 which stores one or more sets of ID data each of which identifies a corresponding one of a plurality of living subjects such as patients. The living subjects are registered in the BP apparatus 208 by storing their ID data in the ID memory area 288. The memory device 280 has a subject-name (SN) memory area (not shown) which stores a plurality of sets of subject-name data each of which is representative of the name of a corresponding one of the subjects. When a set of ID data is stored in the ID memory area 288, a set of subject-name data is stored in the SN memory area. If the ID data read from a magnetic card 76 being inserted in a card reader 74 are found to be identical with one of the sets of ID data stored or registered in the ID memory area 288, the CPU 62 controls the printer 26 to record, on the recording sheet 292a, 292b, 292c, the name of a living subject corresponding to the read ID data, together with the measured BP values obtained in the current operation cycle and a graphic representation showing the time change of the BP values accumulatively stored in the PI memory area 284.

The memory device 280 includes a medicine-related comment (MC) memory area 290 in which are pre-stored a plurality of sets of medicine-related comment data each of which is indicative of a corresponding one of a plurality of predetermined medicine-related comments relating to a plurality of medicines which may be administered by doctors to the living subject 12. The BP apparatus 208 has a plurality of operable keys 272 respectively corresponding to the plurality of medicines. When one of the operable keys 272 is pushed by a doctor, the CPU 62 selects one of the medicine-related comments stored in the MC memory area 290 and controls the printer 26 to record the selected one medicine-related comment, together with the BP values and BP graph, on the recording sheet 292a, 292b, 292c.

The BP apparatus 208 has an image/comment edit device 273 which is operable for inputting a command to the CPU 62 so that the CPU 62 controls the image reader 278 to read an original image and/or an original comment recorded on an original sheet. The image reader 278 includes a display (not shown) for displaying the read original image and/or comment. The edit device 273 is operable for editing the original image and/or comment being displayed on the display. The edit device 273 may include a cursor movable on the display, and a mouse or keyboard operable for moving the cursor on the display. The edit device 273 is capable of enlarging, reducing, moving, and partly cutting out the original image and/or comment on the display. The CPU 62 stores the image and/or comment edited by the edit device 273, in the OI memory area 286 and/or the MC memory area 290, respectively.

The BP apparatus 208 includes a random signal generator circuit 294 which generates a plurality of different random signals. The OI memory area 286 is also capable of storing a plurality of random selectable images which do not relate to the blood pressure of the subject 12 and which correspond to the random signals produced by the generator circuit 294. If a blood pressure measurement of the subject 12 is carried out with the BP apparatus 208 being placed in a random image select mode as one of selectable operation modes, as a result of operation of a mode select dial (not shown) provided on an operator panel 20, the CPU 62 selects one of the random selectable images which corresponds to a random signal being currently produced by the circuit 294, and records the thus random selected one image together with the BP values and BP graph, on the recording sheet 292a, 292b, 292c.

The BP apparatus 208 further includes a clock circuit 296 which provides a time signal indicative of a current date and time. The OI memory area 286 is also capable of storing a plurality of time-related selectable images which do not relate to the blood pressure of the subject and which are related to the time signals produced from the clock circuit 296. If a blood pressure measurement of the subject 12 is effected with the BP apparatus 208 being placed in a time-related image select mode established by operating the mode select dial, the CPU 62 selects one of the time-related selectable images which corresponds to a current date and time provided by the clock circuit 296, and records the thus selected one time-related image together with the BP values and BP graph, on the recording sheet 292a, 292b, 292c.

In the second embodiment, the BP values measured by the BP measuring device 100 are stored in the PI memory area 284 of the memory device 280 each time a blood pressure measurement is carried out on the subject 12. The OI memory area 286 stores different evaluation images relating to the blood pressure of the subject 12; a plurality of different groups of evaluation images (described later); different images relating to the dates and times of measurements provided by the clock circuit 296; and different images corresponding to random signals or values provided by the random signal generator circuit 294. The CPU 62 selects, from the OI memory area 286, one of the evaluation images which corresponds to the current BP values of the subject 12 measured by the BP measuring device 100. The EC memory area 282 stores different evaluation messages used for evaluating the BP values measured by the device 100. The CPU 62 selects, from the EC memory area 282, one of the evaluation comments which corresponds to the current BP values measured by the device 100. The printer 26 records, on the recording sheet 292a, 292b, 292c, the selected evaluation image and the selected evaluation comment together with a list of the BP values obtained by the device 100 in several BP measuring operations and with a BP graph representing the time change of those BP values.

The CPU 62 can select, from the OI memory area 286, one of the different groups of evaluation images which is specified by the ID data read from the magnetic card 76 being inserted in the card reader 74. The CPU 62 can further select one of the selected group of evaluation images which corresponds to the current BP values of the subject 12, and control the printer 26 to record the thus selected evaluation image together with the list of BP values and the BP graph on the recording sheet 292a, 292b, 292c.

The medicine select keys 272 are selectively operable by doctors for specifying and inputting one of different blood-pressure control medicines which may be administered to patients. The MC memory area 290 stores different comments related to the different blood-pressure control medicines. While a medicine-related comment output mode is selected on the BP apparatus 208, the CPU 62 selects, from the MC memory area 290, one of the medicine-related comments which corresponds to the medicine input by a doctor through operation of one of the select keys 272, and controls the printer 26 to record the selected medicine-related comment together with the BP values measured by the BP measuring device 100 on the recording sheet 292a, 292b, 292c.

With a random image output mode being selected on the BP apparatus 208, the CPU 62 selects, from the OI memory area 286, one of the random selectable images which corresponds to the random signal or value provided by the random signal generator circuit 294, and controls the printer 26 to record the thus random selected image together with the BP values and the BP graph on the recording sheet 292a, 292b, 292c.

Similarly, with a time-related image output mode being selected on the BP apparatus 208, the CPU 62 selects, from the OI memory area 286, one of the time-related selectable images which corresponds to the time signal, i.e., current date and time, provided by the clock circuit 296, and operates the printer 26 to record the selected one time-related image together with the BP values and the BP graph on the recording sheet 292a, 292b, 292c.

Furthermore, with an image edit mode being selected, the CPU 62 controls, in response to operation of the image edit device 273, the image reader 278 to read in an original image from an original and display the read-in original image on the display of the reader 278. Medical workers can edit the original image on the image reader 278, by enlarging, reducing, and moving the image and cutting out a part or parts of the image. Similarly, the medical workers can edit an original comment that may be input to the image reader 278 independently of an original image. The CPU 62 stores the thus edited image and/or comment in the OI memory area 286 and/or the MC memory area 290, respectively.

There will be described the operation of the BP measuring apparatus 208.

Figure 9:
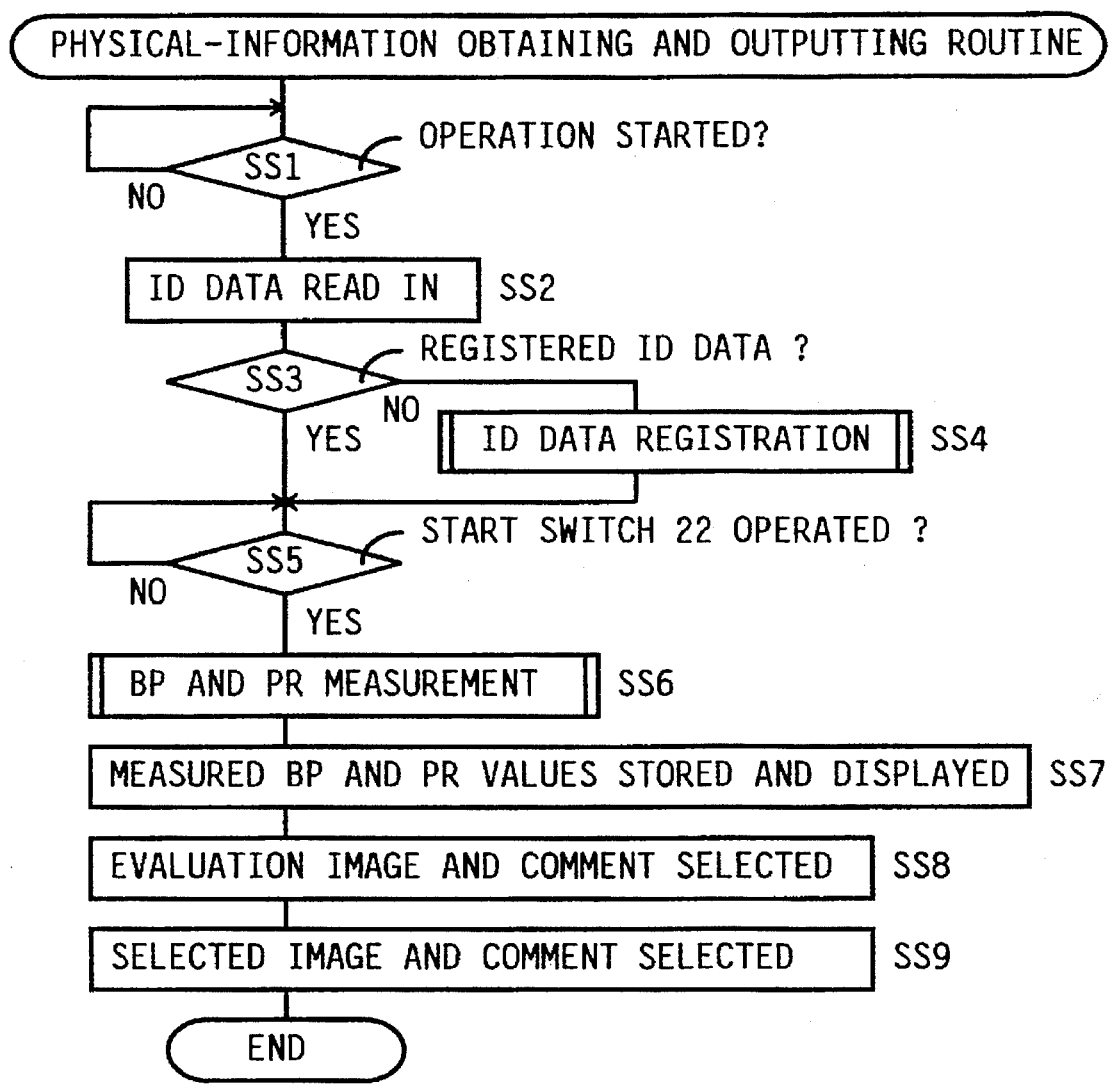
FIG. 9 is a flow chart representing a control program according to which the apparatus of FIG. 8 operates in a BP evaluation mode.

FIG. 9 shows a flow chart representing a control program according to which the BP apparatus 208 carries out a BP evaluation mode in which the apparatus 208 outputs the measured, current BP values of a living subject and an evaluation image and an evaluation comment which evaluate the current BP values of the subject 12.

First, at Step SS1, the CPU 62 judges whether the operation of the BP apparatus 208 has been started, by identifying whether a magnetic card 76 has been inserted in a card insertion slot 28 of the card reader 74, or a main switch (not shown) has been operated. If a negative judgment is made at Step SS1, Step SS1 is repeated. On the other hand, if a positive judgment is made, the control of the CPU 62 proceeds with Step SS2 to control the card reader 74 to read the ID data recorded on the ID card 76 being inserted in the card slot 28. The CPU 62 temporarily stores, in the RAM 66, the ID data read by the card reader 74.

Step SS2 is followed by Step SS3 to judge whether the set of ID data read from the card 76 is identical with one of the sets ID data stored or registered in the ID memory area 288. If a negative judgment is made at Step SS3, the control of the CPU 62 goes to Step SS4 where the set of ID data is stored or registered in the ID memory area 288 according to an ID data register routine. Step SS4 is followed by Step SS5. On the other hand, if a positive judgment is made, the control of the CPU 62 directly proceeds with Step SS5 to judge whether a START switch 22 has been operated to start a BP measurement.

The CPU 62 repeats Step SS5 until a positive judgment is made at this step. If a positive judgment is made at Step SS5, the control goes to Step SS6, i.e., BP measure subroutine in which a systolic (SAP), a diastolic (DAP), a mean blood pressure (MAP) value, and a pulse rate (PR) value, of the living subject 12 are measured or determined. In the BP measure subroutine, the CPU 62 operates, according to a pre-stored algorithm, for automatically raising the cuff pressure of an inflatable cuff 16 and determining during the reduction of the cuff pressure the SAP, DAP, and MAP values of the living subject 12 in to the known oscillometric BP measuring method. For example, the SAP value may be determined as being equal to a cuff pressure at the time of occurrence of a first maximum difference out of the differences obtained by successively calculating the difference of respective amplitudes of each pair of successive pulses of the pulse wave signal SM supplied during the reduction of the cuff pressure. Similarly, the DAP value may be determined as being equal to a cuff pressure at the time of occurrence of a second maximum difference out of those differences. The MAP value is determined as being equal to a cuff pressure at the time of occurrence of a pulse having a maximum amplitude out of the pulses. The PR value is determined based on a time difference between two successive pulses of the pulse wave signal SM.

Step SS6 is followed by Step SS7 to store, in the PI memory area 284, data indicative of the BP and PR values determined at Step SS6, together with data indicative of the date and time provided by the clock circuit 296, in relation with the ID data obtained at Step SS2. Additionally, the CPU 62 commands the SAP, DAP, and PR displays 32, 34, 36 to display the measured SAP, DAP, and PR values, respectively.

At the following Step SS8, the CPU 62 selects, from the OI memory area 286, one of the evaluation images which corresponds to the current BP values measured at Step SS6 and selects, from the EC memory area 282, one of the evaluation comments which corresponds to the current BP values measured at Step SS6.

Figure 10:
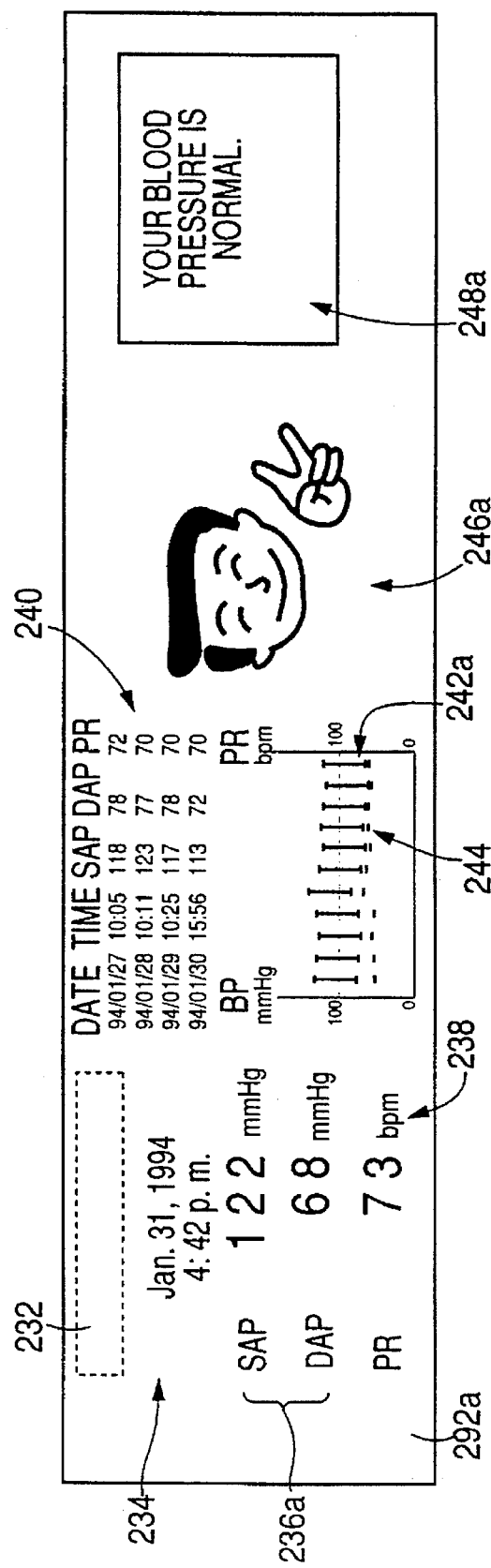
FIG. 10 is a view corresponding to FIG. 5, showing a printed output of the apparatus of FIG. 8 as a result of an operation of the same according to the flow chart of FIG. 9, in the case where measured BP values are normal.
Figure 11:
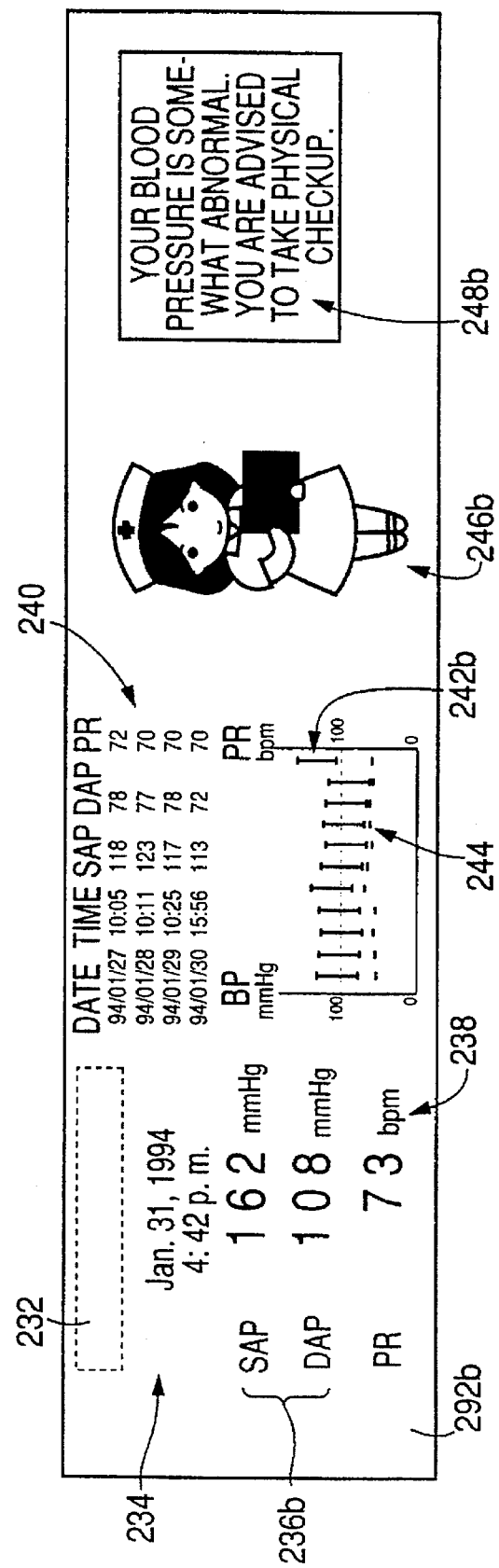
FIG. 11 is a view corresponding to FIG. 10, showing another printed output of the apparatus of FIG. 8, in the case where measured BP values are somewhat abnormal.
Figure 12:
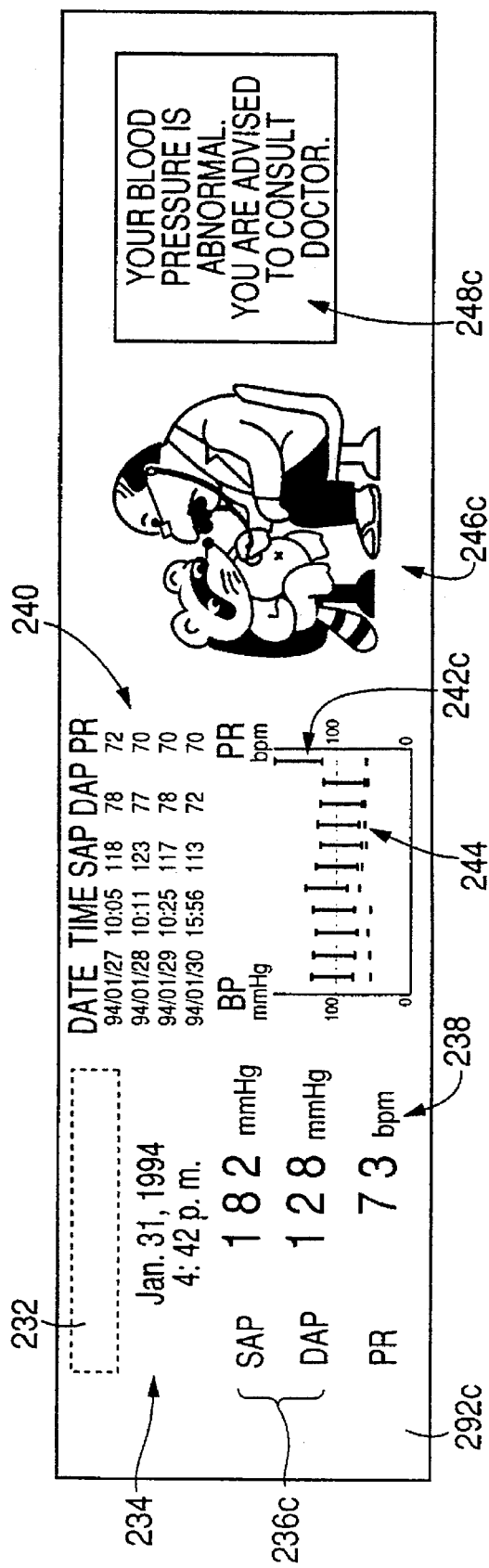
FIG. 12 is a view corresponding to FIG. 10, showing yet another printed output of the apparatus of FIG. 8, in the case where measured BP values are abnormal.

Step SS8 is followed by Step SS9 where the CPU 62 controls the printer 26 to record or print, on the recording sheet 292 (292a, 292b, 292c) shown in FIG. 10, 11, or 12, (a) a name 232 of the subject 12 corresponding to the ID data read from the card 76; (b) a date and time when the current BP measurement is carried out; (c) current BP values 236 (236a, 236b, 236c) measured at Step SS6; (d) a current PR value 238 measured at Step SS6; (e) a list 240 of the BP values and PR values accumulatively stored in the PI memory area 284; (f) a graphic representation 242 (242a, 242b, 242c) of the BP values accumulatively stored in the PI memory area 284; (g) a graphic representation 244 of the PR values accumulatively stored in the PI memory area 284; (h) a pictorial evaluation image 246 (246a, 246b, 246c) corresponding to the current BP values; and (i) an evaluation comment 248 (248a, 248b, 248c) corresponding to the current BP values. FIG. 10 shows an example of an output by the BP apparatus 208 for normal BP values; FIG. 11 shows an example of an output for somewhat abnormal BP values; and FIG. 12 shows an example of an output for abnormal BP values. The evaluation image and comment 146a, 148a indicate that the current BP values are normal; the image and comment 246b, 248b indicate that the current BP values are somewhat abnormal; and the image and comment 246c, 248c indicate that the current BP values are abnormal.

It emerges from the foregoing description that in the second embodiment the CPU 62 selects, from the output image (OI) memory area 286, one of the different evaluation images 246a, 246b, 246c which corresponds to the current BP values of the living subject 12 measured by the BP measuring device 100 and controls the printer 26 to record, on the recording sheet 292a, 292b, 292c the selected evaluation image 246a, 246b, 246c together with the list 240 of the BP values measured in the prior measuring operations and the BP graph 242 indicating the time change of the prior and current BP values. Since the evaluation image 246a, 246b, 246c corresponding to the current BP values is output together with the BP values obtained in the past measuring operations, the living subject 12 or medical workers can visually identify an abnormality of the current BP values, and the subject 12 can remember the abnormal measurement result for a long time.

In addition, in the second embodiment, the printer 26 records, on the recording sheet 292a, 292b, or 292c shown in FIG. 10, 11, or 12, (a) the name 232 of the living subject 12; (b) the date and time of the current measurement; (c) the current BP values 236a, 236b, 236c; (d) the current PR value 238; (e) the list 240 of the prior BP and PR values; (f) the graphic representation 242a, 242b, 242c of the prior and current BP values; (g) the graphic representation 244 of the prior and current PR values; (h) the evaluation image 246a, 246b, 246c corresponding to the current BP values; and (i) the evaluation comment 248a, 248b, 248c corresponding to the current BP values. Since medical workers or the living subject 12 can carry the recording sheet 292a, 292b, 292c, the BP apparatus 208 eliminates the burden of writing down the BP and PR values displayed on the display panel 30 or keeping those values in mind.

Furthermore, in the second embodiment, since the BP graph 242a, 242b, 242c representing the time change of the prior and current BP values obtained in the several BP measurements is output on the recording sheet 292a, 292b, 292c, medical workers or the living subject 12 can easily recognize the history of the BP values of the subject 12.

Figure 13:
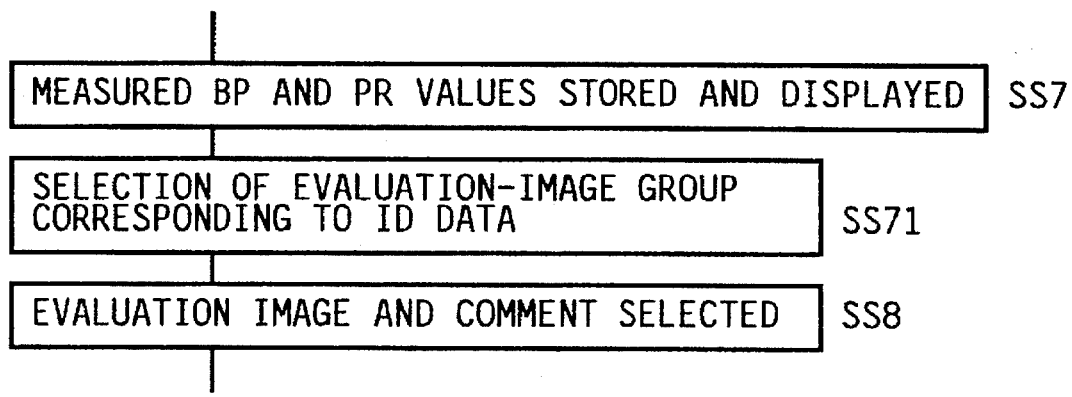
FIG. 13 is a flow chart corresponding to FIG. 9, representing another control program according to which the apparatus of FIG. 8 operates.

While the BP apparatus 208 is placed in an evaluation-image change mode as a result of operation of the mode select dial (not shown), the apparatus 208 or CPU 62 operates according to a control program represented by the flow chart of FIG. 13 and obtained by adding Step SS71 between Steps SS7 and SS8 of the flow chart of FIG. 9. As described previously, the output image (OI) memory area 286 stores a plurality of groups of evaluation images. Since a normal (or abnormal) BP range changes depending upon sex, age, patient's medical history, etc., it is not appropriate to use a single group of evaluation images to all the human beings including male and female, young and old, health and sick, etc. Therefore, a plurality of different groups of evaluation images are employed for male, female, and old, respectively. The ID data recorded on the magnetic card 72 include the data indicative of the sex, age, medical history, etc. of the living subject 12 carrying the card 72, and the CPU 62 selects, at Step SS71, one of the different groups of evaluation images which one group corresponds the ID data read from the card 72 at Step SS2. At Step SS8, the CPU 62 selects one of the selected group of evaluation images which one image corresponds to the current BP values of the subject 12 measured by the measuring device 100. In this mode, the BP apparatus 208 outputs an evaluation image more accurately evaluating the current BP values of the male or female, young or old subject 12. Each image belonging to the group of evaluation images for, e.g., the male may contain the figure of a male person only. It may be the case with the group of images for the female or the old. In those cases, if an evaluation image indicating an abnormal blood pressure is output on a recording sheet, the output image will give a clearer visual impression to the subject 12.

Figure 14:
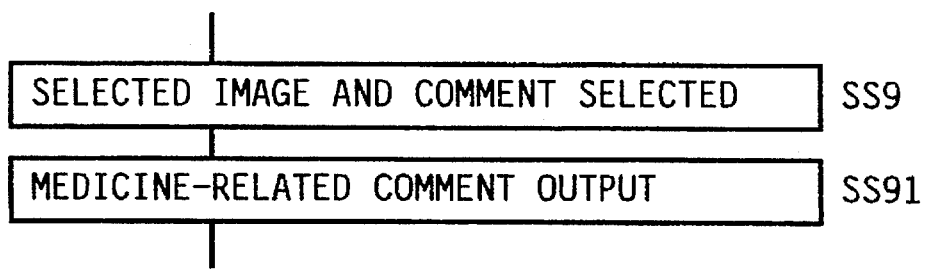
FIG. 14 is a flow chart corresponding to FIG. 9, representing yet another control program according to which the apparatus of FIG. 8 operates.

While the BP apparatus 208 is placed in a medicine-related comment output node in response to operation of the mode select dial, the apparatus 208 or CPU 62 operates according to a control program represented by the flow chart of FIG. 14 and obtained by adding Step SS91 after Step SS9 of the flow chart of FIG. 9. As described previously, the medicine-related comment (MC) memory area 290 stores a plurality of medicine-related comments relating to the medicines which may be administered by doctors to patients. At Step SS91, the CPU 62 selects, from the MC memory area 290, one of the medicine-related comments which corresponds to the medicine selected by a medical worker by pushing a corresponding one of the medicine select keys 272, and controls the printer 26 to record, e.g., on the recording sheet 292c shown in FIG. 12, the selected medicine-related comment in addition to the other items 232–248. For example, a medicine-related comment may read as follows: THIS MEDICINE, NAMED "XXXX", IS FOR IMPROVING YOUR BLOOD PRESSURE. TAKE "Y" TABLETS AFTER EVERY MEAL FOR "Z" DAYS. In the case where a doctor makes a diagnosis based on the measured BP values of the living subject 12 and hands out a selected blood pressure treating medicine to the subject 12, the BP apparatus 208 outputs, in response to doctor's input of data indicating the selected medicine through operation of a corresponding key 272, a comment related to the selected medicine together with the BP values on the recording sheet 92. The medicine-related comment may describe the manner of use of the medicine, the virtue of the medicine, directions for use of the medicine, etc. Since the medicine-related comment is recorded on the sheet 92, the doctor need not write down the comment on a sheet of paper or the subject 12 need not keep it in mind.

Figure 15:
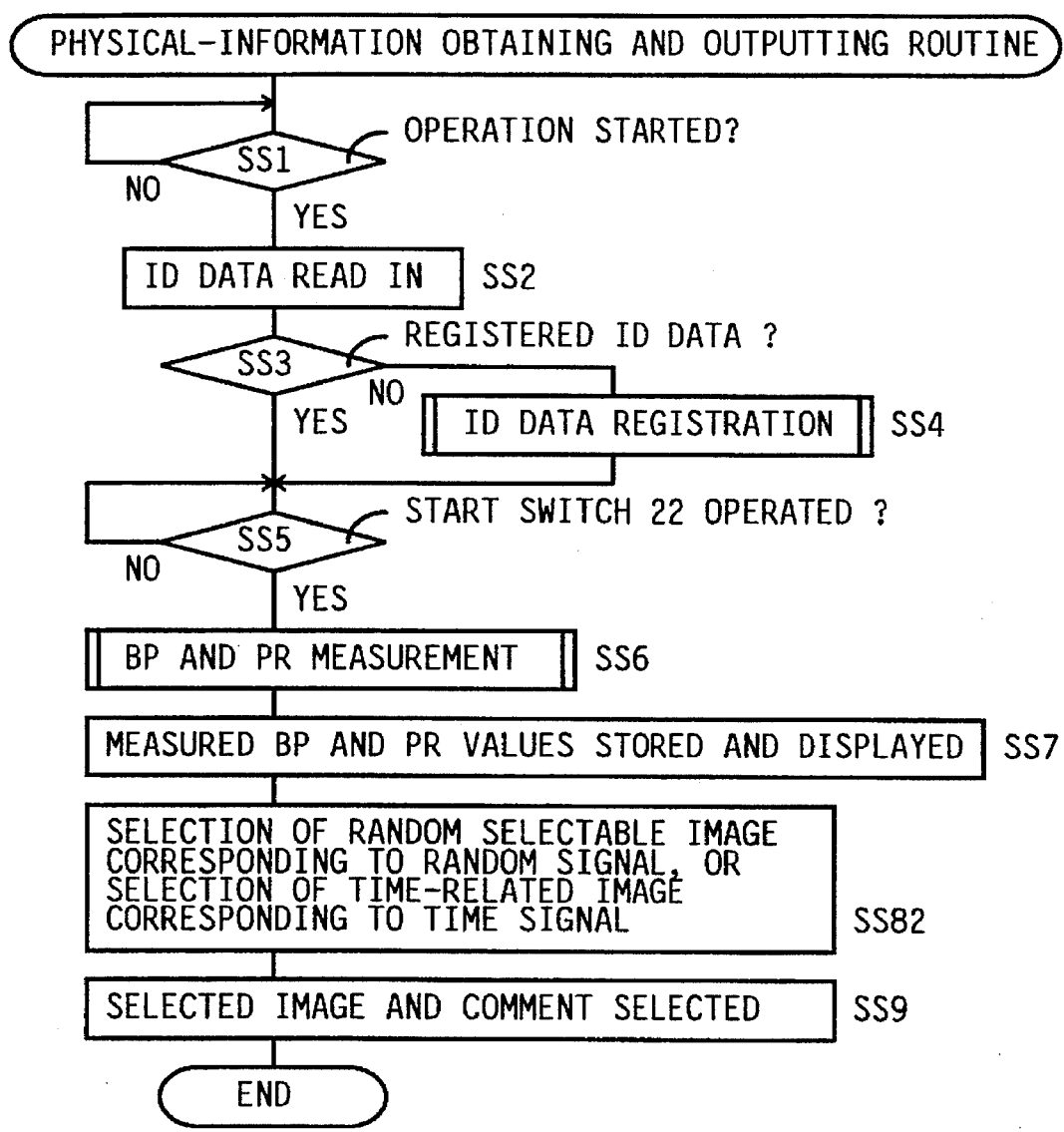
FIG. 15 is a flow chart corresponding to FIG. 9, representing another control program according to which the apparatus of FIG. 8 operates either in a random image output mode or in a time-related image output mode.

While the BP apparatus 208 is placed in the random image output mode, or the time-related image output mode, in response to operation of the mode select dial, the apparatus 208 or CPU 62 operates according to a control program represented by the flow chart of FIG. 15 and obtained by adding Step SS82 in place of Step SS8 of the flow chart of FIG. 9. As described previously, the OI memory area 286 stores a plurality of random selectable images that are not be related to blood pressure, and a plurality of time-related selectable images that are not be related to blood pressure. In the random image output mode, at Step SS82, the CPU 62 selects, from the OI memory area 286, one of the random selectable images which corresponds to the random signal or value provided by the random signal generator circuit 294 and controls, at Step SS9, the printer 26 to record, on the recording sheet 292, the random selected image in place of the evaluation image and message 246, 248 and in addition to the other items 232–244. In the time-related image output mode, at Step SS82, the CPU 62 selects, from the OI memory area 286, one of the time-related selectable images which corresponds to the date and time provided by the clock circuit 294 and controls, at Step SS9, the printer 26 to record, on the recording sheet 292, the selected time-related image in place of the evaluation image and message 246, 248 and in addition to the other items 232–244. The random or time-related selectable images may include images representing season's flowers, season's landscapes, etc. Those selectable images effectively operate for visually impressing the measured BP values on the subject 12.

Figure 16:
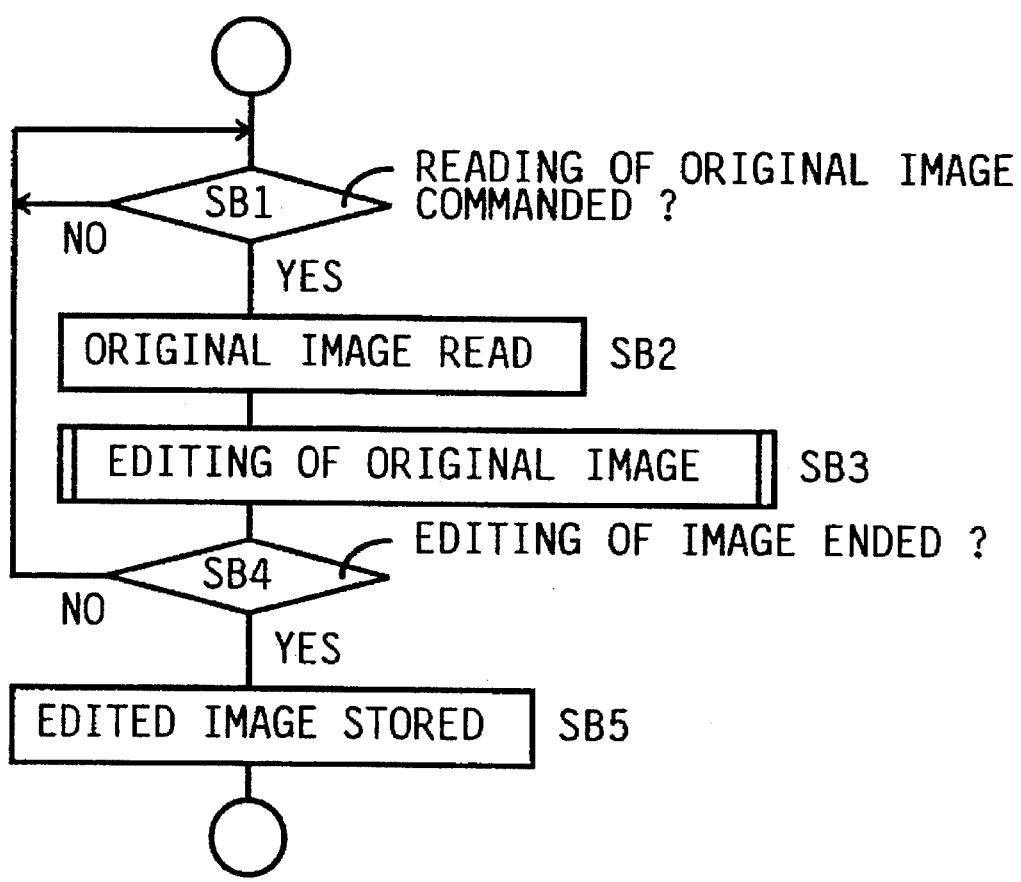
FIG. 16 is a flow chart corresponding to FIG. 9, representing yet another control program according to which the apparatus of FIG. 8 operates in an image/comment edit mode.

While the BP apparatus 208 is placed in the image/comment input and edit mode in response to operation of the mode select dial, the apparatus 208 or CPU 62 operates according to a control program represented by the flow chart of FIG. 16. The routine of FIG. 16 is carried out for preparing various images to be stored in the OI memory area 286 and evaluation comments to be stored in the evaluation comment (EC) memory area 282. First, at Step SB1, the CPU 62 judges whether an original image has been read in from an original upon operation of a reading-in key of the edit device 273. If a negative judgment is made at Step SB1, Step SB1 is repeated. On the other hand, if a positive judgment is made, the control of the CPU 62 goes to Step SB2 to control the image reader 278 to read in the original image from the original, e.g., sheet bearing the original image. The original image may be an original evaluation comment. Usually, an original evaluation comment is recorded on a different or separate sheet from a sheet on which an original pictorial image is recorded. At the following Step SB3, the CPU 62 edits the original image in response to command signals input through operation of the edit device 273. Specifically, the CPU 62 enlarges or reduces the size of the original image, moves the image, or cuts out a part of the image, on the display of the image reader 278, so that the thus edited image is suitable for being output on the recording sheet 92. Step SB3 is followed by Step SB4 to judge whether the editing operation has been finished, by identifying whether an edit end key of the edit device 273 has been operated. If a negative judgment is made at Step SB4, the control of the CPU 62 returns to Step SB1 and the following steps. On the other hand, if a positive judgment is made at Step SB4, the control goes to Step SB5 to store the edited pictorial image in the OI memory area 286, and store the edited evaluation comment in the EC memory area 282, with or without relation with data specifying the attributes of the edited image or comment. The attributes of an edited image or comment may comprise (a) correspondence to the normal or abnormal BP values, (b) correspondence to a specific group for the male, female, young, or old, and (c) correspondence to a specific time such as a season or a month. In this mode, the BP apparatus 208 enables medical workers or other users to easily input and edit, and then register, in the apparatus 208, their desirable pictorial images and/or evaluation comments to be output with measured BP values on a recording sheet 92.

It is to be understood that the BP apparatus 208 may otherwise be modified.

For example, while the control circuit 56 or CPU 62 is capable of carrying out all the control programs represented by the flow charts of FIGS. 9, 13, 14, 15, and 16, the CPU 62 may be modified to carry out one or more (but not all) of those programs.

While the memory device 280 is incorporated in the BP apparatus 208, it is possible to provide the memory device 280 outside the BP apparatus 208 and connect the memory device 280 to the BP apparatus 208. Otherwise, the memory device 280 may be provided in a host computer to which the BP apparatus 208 is connected via a communication line such as a telephone line.

Next, there will be described a third embodiment of the present invention. The third embodiment relates a blood pressure (BP) measuring apparatus 310 having a side view and a front view shown in FIGS. 17 and 18, respectively. The BP measuring apparatus 310 is similar to the BP measuring apparatus 8 shown in FIGS. 1 and 2. Therefore, the same reference numerals as used in FIGS. 1 and 2 are used to designate corresponding elements or parts of the BP apparatus 310, and the description of those elements or parts is omitted. The following description will be focused on the differences of the BP apparatus 310 from the BP apparatus 8.

Figure 18:
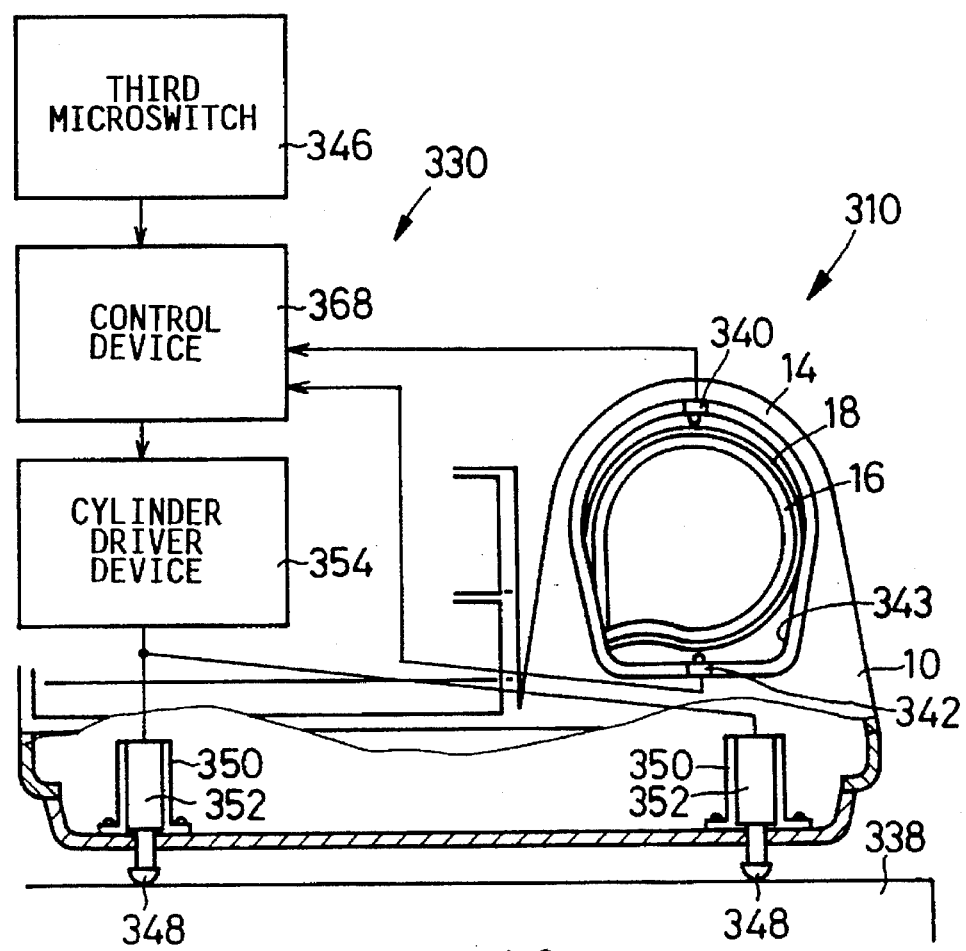
FIG. 18 is a diagrammatic view of a partly structural and partly electric arrangement of the apparatus of FIG. 17, showing an arm-receiver positioning device and a misalignment detector.

The BP apparatus 310 has an automatic cuff winding device 330, shown in FIG. 18, which automatically winds an inflatable cuff 16 (and an elongate belt 18) around an upper arm of a living subject 12 (FIG. 1). For carrying out a BP measurement using the BP apparatus 310, the subject 12 is required to insert his or her arm into an arm receiver 14 in the same manner as that used on the BP apparatus 8 of FIG. 1. More specifically, the subject 12 inserts his or her arm in the receiver 14 such that the elbow of the arm comes out of a rear-side opening of the tunnel-like arm receiver 14. In the present embodiment, the cuff winding device 330 includes the arm receiver 14, cuff 16, belt 18, and other elements (described later); the cuff 16 serves as an inflatable bag; and the belt 18 serves as a bag support. The cuff 16 and the belt 18 cooperate with each other to provide an arm belt for pressing the subject's arm.

Figure 17:
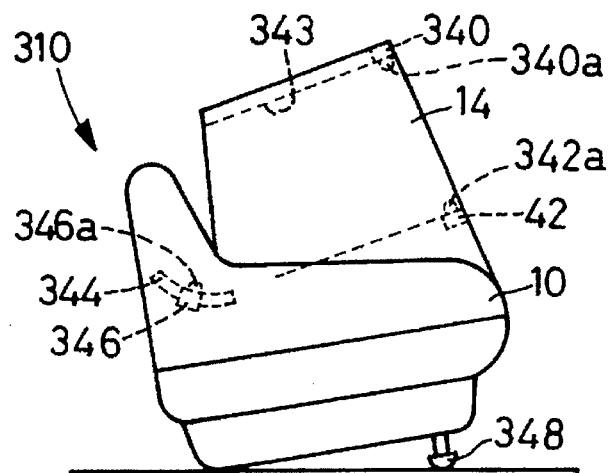
FIG. 17 is a side view of a BP measuring apparatus as a third embodiment of the present invention.

In FIG. 17, the BP apparatus 310 is placed on a table 338. A first and a second microswitch 340, 342 are provided at a top and a bottom of a front-side opening of the tunnel-like arm receiver 14. Each of the two microswitches 340, 342 has a contact member 340a, 342a and is embedded in an inner surface 343 of a housing 10 such that the contact member 340a, 342a is exposed to an inner space of the arm receiver 14. When the subject's arm 12 is inserted in the receiver 14 and appropriately positioned relative to the receiver 14, the respective contact members 340a, 342a of the two microswitches 340, 342 do not contact the upper arm 12 so that each contact member 340a, 342a takes its original state and each microswitch 340,342 takes its OFF state. Each microswitch 340, 342 supplies a detection or non-detection signal indicative of its ON or OFF state, to a control device 368 (FIG. 18). Thus, the microswitches 340, 342 serve as a detector for identifying whether the longitudinal axis line of the subject's upper arm 12 is aligned with the longitudinal axis line of the cylindrical arm receiver 14.

At the rear opening of the arm receiver 14, there is provided an elbow rest 344 having a curved surface shown in FIG. 17. The elbow rest 344 is fixed to the housing 10 with a fixing member (not shown). A third microswitch 346 is embedded in the curved surface of the elbow rest 344 such that a contact member 346a of the microswitch 346 is exposed in the curved surface. When the elbow of the subject's arm 12 is placed on the elbow rest 344, the contact member 346a of the switch 346 contacts the elbow and is pushed. Consequently, the third switch 346 is changed from its OFF state to its ON state and supplies the detection signal indicative of the ON state to the control device 368. Thus, the third microswitch 346 identifies whether a sufficient length of the subject's arm 12 has been inserted into the arm receiver 14.

As shown in FIG. 18, the BP apparatus 310 has, near the front end thereof, a left and a right adjustable legs 348, 348 which extend downward from a bottom wall 10a of the housing 12. The length of extension of the legs 348 from the outer surface of the bottom wall 10a is adjustable in a manner described later. When the length of extension of the legs 348 is adjusted, the angle of inclination of the housing 10, therefore also the arm receiver 14, is changed relative to the table 338.

Figure 19:
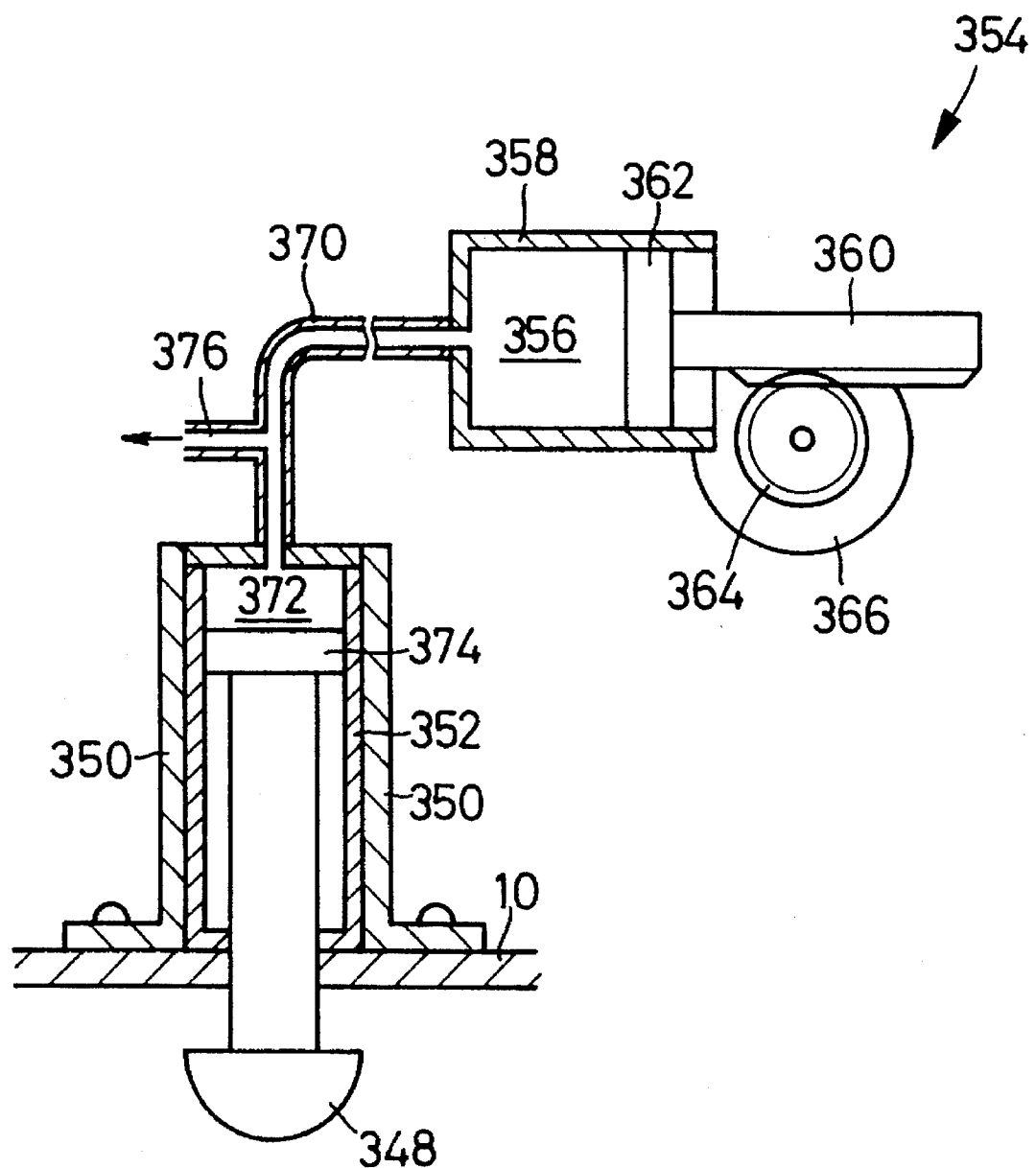
FIG. 19 is a view of a cylinder drive device of the apparatus of FIG. 17.

Each leg 348 fits in a first cylinder 352 fixed to the inner surface of the bottom wall 10a using a metal member 350, such that each leg 348 is advanceable outward from the corresponding first cylinder 352. The amount of advancement of the legs 348 from the first cylinders 352, i.e., length of extension of the legs 348 from the bottom wall 10a is adjusted by a cylinder drive device 354 provided in the housing 10. As shown in FIG. 19, the cylinder drive device 354 includes a second cylinder 358 having a working fluid in a fluid chamber 356; a piston 362 movable in the second cylinder 358 in an axial direction of the cylinder 358 and fixed to a rack 360; a motor 366 having a reduction gear unit and a rotation shaft which supports a pinion 364 engaged with the rack 360.

The motor 366 with the reduction gear unit is driven or rotated in response to a command from the control device 368, so that an appropriate fraction of the working fluid is supplied via piping 370 from the fluid chamber 356 of the second cylinder 358 to a fluid chamber 372 of the first cylinder 352, or so that an appropriate fraction of the working fluid is removed via the piping 370 from the fluid chamber 372 of the first cylinder 352 into the fluid chamber 356 of the second cylinder 358. Each leg 348 is fixed to a piston 374 provided in the corresponding first cylinder 352. When the amount of working fluid in the fluid chamber 372 is increased or decreased and therefore the piston 374 is moved forward or backward in the first cylinder 352, the amount of advancement of each leg 348 from the corresponding first cylinder 352 is adjusted. Since the two first cylinders 352, 352 are connected via the piping 370 and a bypass passage 376 to the cylinder drive device 354, the single drive device 354 operates for simultaneously adjusting the advancement amounts of the two legs 348, 348.

The control device 368 starts to adjust the angle of inclination of the housing 10 or arm receiver 14, in response to the detection or non-detection signal supplied from the third microswitch 346. The control device 368 continues to adjust the inclination angle of the housing 10 so long as at least one of the first and second microswitches 340, 342 continues to supply the detection signal indicative of the ON state to the control device 368, i.e., so long as the subject's arm 12 continues to contact at least one of the top and bottom of the front opening of the arm receiver 14. In the present embodiment, the adjustable legs 348, first cylinders 352, and cylinder drive device 354 cooperate with each other to serve as an arm-receiver positioning device. The control device 368 may be constituted by a microcomputer.

When the BP apparatus 310 is used to carry out a BP measurement on the subject 12, a START switch 22 is operated, and then the subject inserts his or her arm 12 into the arm receiver 14 from the front opening thereof and places the elbow of the arm 12 on the elbow rest 344. If a sufficient length of the arm 12 is inserted into the receiver 14 and the third microswitch 346 provided in the elbow rest 344 is placed in the ON state, the control device 368 starts to adjust the inclination angle of the housing 10. If, in this situation, the first or second microswitch 340, 342 is placed in the ON state as a result of contact of the contact member 340a, 342a with the arm 12, the control device 368 controls the motor 366 to operate or rotate so that the working fluid is supplied to, or removed from, the fluid chambers 372 of the first cylinders 352. Thus, the amount of advancement of the legs 348 is adjusted. In the case where the first microswitch 340 is pushed by the arm 12, the motor 366 is rotated in a counterclockwise direction as seen in FIG. 19, so that the legs 348 are advanced. On the other hand, in the case where the second microswitch 342 is pushed by the arm 12, the motor 366 is rotated in a clockwise direction as seen in FIG. 19, so that the legs 348 are retracted. When the control device 368 does not receive any detection signal from the two microswitches 340, 342 as a result of the adjusting operation, the control device 368 stops the operation of the cylinder drive device 354 and starts to tight up the belt 18 and inflate the cuff 16 by supplying a pressurized air to the cuff 16. Thus, a BP measurement is started. Since the tightening up of the belt 18 and the inflation of the cuff 16 wound around the subject's upper arm 12, and the BP measuring method using the cuff 16 are well known in the art, the description of those steps is omitted. Following completion of the BP measurement, the cuff 16 is deflated and the belt 18 is loosened, thereby permitting the subject to withdraw his or her arm 12 from the arm receiver 14. Thus, a series of steps are ended. Once a BP measurement has been started, the control device 368 does not operate the cylinder drive device 354 again before the elbow of the arm 12 is lifted up and the contact member 346a of the third microswitch 346 is restored to the OFF state thereof. Since the motor 366 is provided with the reduction gear unit, the amount of advancement of the legs 348 cannot be changed with the motor 366 being stopped.

It emerges from the foregoing description of the the third embodiment that when the arm 12 is inserted in the arm receiver 14 and the elbow of the arm 12 is placed on the elbow rest 344, the control device 368 controls the cylinder drive device 354 to adjust the amount of advancement of the legs 348 so that each of the first and second microswitches 340, 342 supplies a non-detection signal indicative of the OFF state in which the corresponding contact member 340a, 342a is not held in contact with the arm 12. Stated differently, the control device 368 controls the cylinder drive device 354 to adjust the angle of inclination of the arm receiver 14 relative to the table 338 so that the longitudinal axis line of the upper arm 12 is substantially aligned with the longitudinal axis line (i.e., central axis line) of the arm receiver 14. Thus, the present BP apparatus 310 establishes an appropriate position of the arm receiver 14 relative to the subject's arm 12 where the arteries of the arm 12 are not locally or partially pressed by the cuff 16, without requiring the subject to adjust his or her arm 12 relative to the receiver 14. Stated differently, the BP apparatus 310 accurately measures the BP values of the subject 12 while permitting the subject 12 to take a natural posture.

Since in the present embodiment the control device 368 starts to adjust the inclination angle of the arm receiver 14 when the contact member 346a of the third microswitch 346 is pushed under the elbow of the subject's arm 12 and starts a BP measurement following completion of the adjusting of the inclination angle, the BP apparatus 310 carries out the BP measurement with the arm 12 being appropriately inserted in the arm receiver 14.

Figure 20:
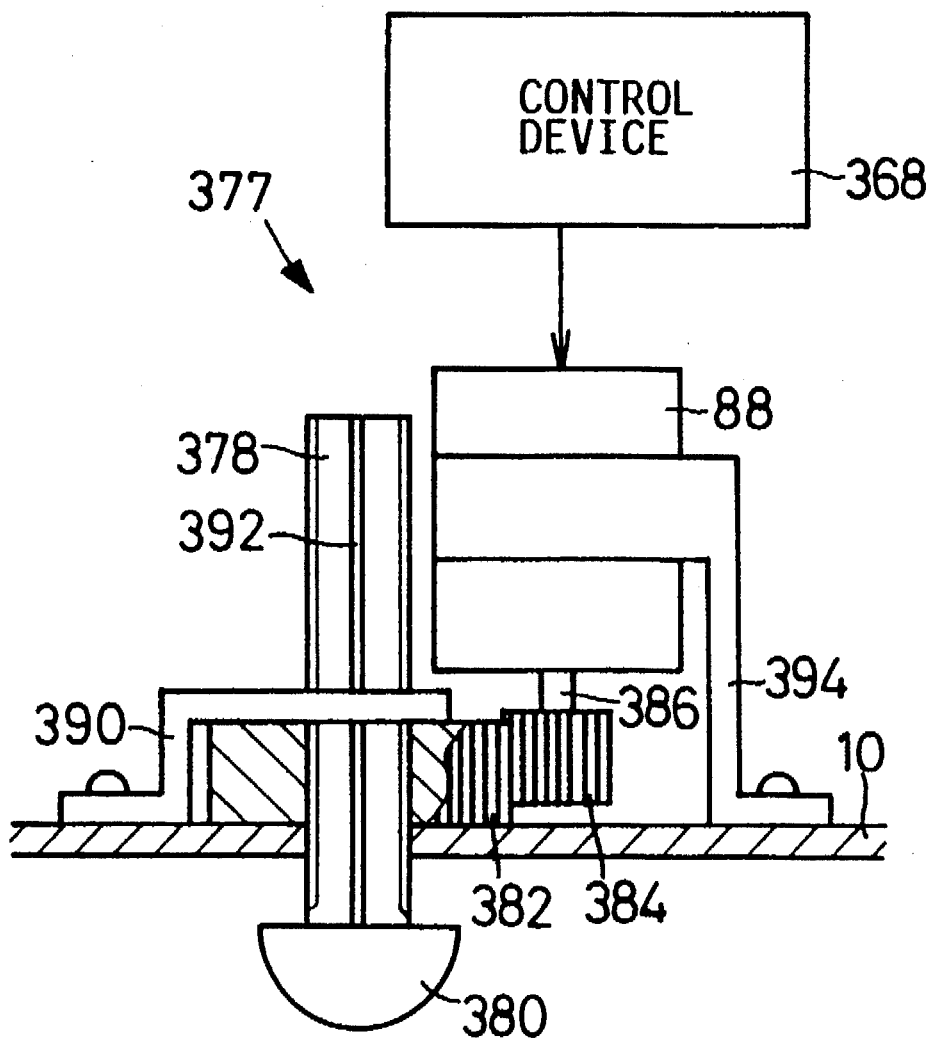
FIG. 20 is a view of another arm-receiver positioning device which may be employed in the apparatus of FIG. 17.

FIG. 20 shows another arm-receiver positioning device 377 which may be employed, in place of the legs 348, cylinders 352, and drive device 354 shown in FIG. 18, for adjusting the inclination angle of the housing 10 of the BP apparatus 310 relative to the table 338. The positioning device 377 includes two legs 380, 380 each of which includes an externally threaded axis portion 378; an internally threaded nut 382 held in threaded engagement with the axis portion 378 of each leg 380 and having teeth in an outer circumferential surface thereof; and a motor 388 having a rotation shaft 386 which supports a pinion 384 held in engagement with the teeth of the nut 382. A fixing metal member 390 having a hole (not shown) through which the axis portion 378 of each leg 380 extends, holds the corresponding nut 382 such that the nut 382 cannot be moved in an axial direction of the axis portion 378 of the leg 380. Each adjustable leg 380 has an axial groove 392 formed in the threaded outer surface of the axial portion 378. Since the metal member 390 has a key (not shown) extending into the hole through which the axial portion 378 extends, and held in engagement with the axial groove 392 of the axial portion 378. Consequently, each leg 380 is prevented from being rotated about the axis thereof, and is permitted to displace in the axial direction thereof with rotation of the corresponding nut 382. The motor 388 is fixed with a fixing metal member 394 to the inner surface of the bottom wall of the housing 10, and operates or rotates in response to a command from the control device 368. The two legs 388 are associated with the corresponding motors 388, respectively. The arm-receiver positioning device 377 may be made more compact than the positioning device constituted by the legs 348, cylinders 352, and drive device 354 shown in FIG. 18. The motors 388 need not be provided with a reduction gear unit unlike the motor 366 shown in FIG. 19.

Figures 21A, 21B:
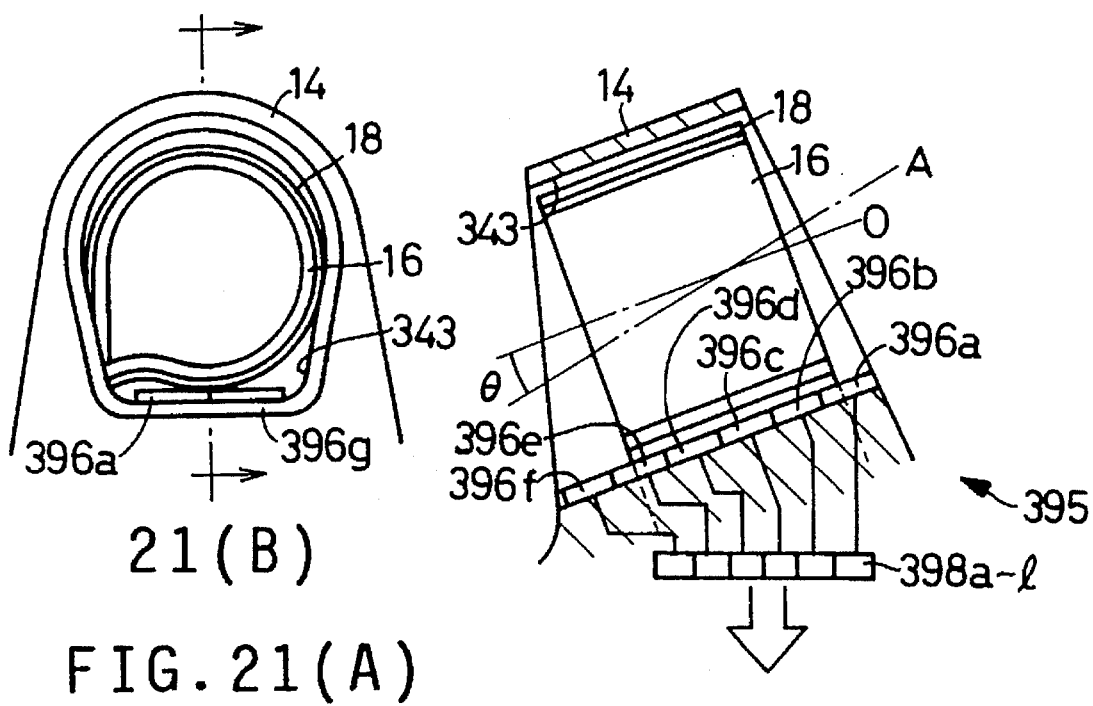
FIG. 21(A) is a front view of another misalignment detector which may be employed in the apparatus of FIG. 17.
FIG. 21(B) is a cross section of the misalignment detector of FIG. 21(A) taken along Line 21(B)—21(B)

FIGS. 21(A) and 21(B) show another detector 395 which may be employed, in place of the microswitches 340, 342 shown in FIG. 18, for identifying whether the longitudinal axis line of the upper arm 12 is substantially aligned with the longitudinal axis line of the arm receiver 14. The detector 395 includes a number of air chambers 396 provided on the bottom of the inner surface 343 of the tunnel-like arm receiver 14. In the present embodiment, the air chamber 396 includes twelve air chambers 396a to 396l, i.e. first array of air chambers 396a to 396f and second array of air chambers 396g to 396l. Each array 396a–396f, 396g–396l extends parallel to the longitudinal axis line of the arm receiver 14. The air chambers 396h to 396l are not shown in FIG. 21(A) or 21(B) since those chambers are provided in rear of the air chambers 396b to 396f shown in FIG. 21(B). The twelve air chambers 396a–396l communicate with pressure switches 398a to 398l, respectively. When each air chamber 396 is pressed, a pressure change is produced in the corresponding pressure switch 398, which supplies a pressure signal indicative of the detected pressure of each chamber 396, to the control device 368. When the subject's arm 12 is inserted into the arm receiver 14 for a BP measurement, the control device 368 starts to adjust the inclination angle of the housing 10, based on the pressure signals supplied from the pressure switches 398a–398l, so that the longitudinal axis line of the upper arm 12 is substantially aligned with the longitudinal axis line of the arm receiver 14. In the case where an angle, θ, of the longitudinal axis line, A, of the upper arm 12 from the longitudinal axis line, o, of the arm receiver 14 is positive as shown in FIG. 21(b) (it is assumed that any angle of rotation in a counterclockwise direction from the reference axis o is positive), the respective pressures in the air chambers 396e, 396f, 396k, 396l provided in the rear portion of the arm receiver 14 are increased. Accordingly, the control device 368 operates for increasing the inclination angle of the housing 10 and thereby decreasing the respective pressures of those chambers 396e, 396f, 396k, 396l. On the other hand, in the case where the angle θ of the axis line A of the upper arm 12 from the axis line o of the arm receiver 14 is negative, the respective pressures in the air chambers 396a, 396b, 396g, 396h provided in the front portion of the receiver 14 are increased. Accordingly, the control device 368 operates for decreasing the inclination angle of the housing 10 and thereby decreasing the respective pressures of those chambers 396a, 396b, 396g, 396h. That is, the control device 368 operates for positioning the housing 10 or arm receiver 14 so that the pressing forces exerted by the upper arm 12 to the air chambers 396a to 396l are made substantially uniform with one another. Consequently, the axis line A of the upper arm 12 is substantially aligned with the axis line o of the arm receiver 14.

Figure 22:
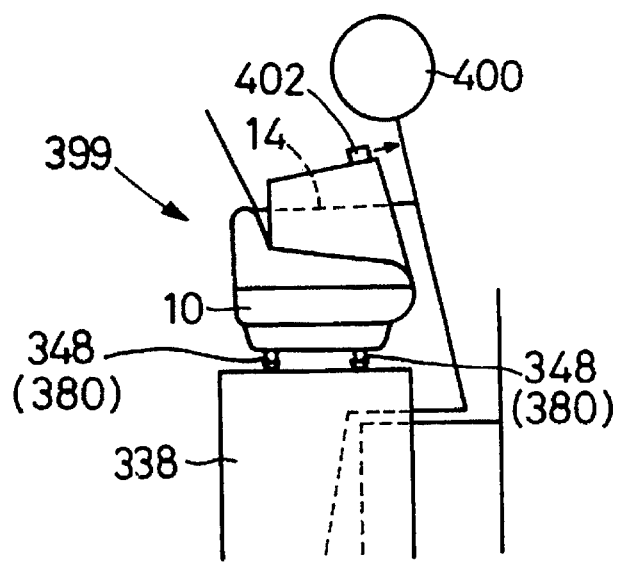
FIG. 22 is a view of yet another arm-receiver positioning device and yet another misalignment detector which may be employed in the apparatus of FIG. 17.

FIG. 22 shows another arm-receiver positioning device 399 which may be employed for adjusting the height of the housing 10 of the BP apparatus 310 from the table 338. The present positioning device 399 includes four adjustable legs 348 or 380 provided at the four corners of the bottom wall of the housing 10. The control device 368 adjusts the respective amounts of advancement of the four legs 348, 380 from the bottom of the housing 10, all in the same manner using the positioning device 348, 352, 354 shown in FIG. 18, or the positioning device 377 shown in FIG. 20, in such a manner that the inclination angle of the housing 10 relative to the table 2338 is not adjusted but the height of the housing 10 from the table 338 is adjusted. In FIG. 22, the first and second microswitches 340, 342 or the air chambers 396 and pressure switches 398 are not provided on the inner surface 343 of the arm receiver 14, but an optical sensor 402 which measures the sitting height of a living subject 400 or the height of the subject's shoulder, is provided on the top of the outer circumferential surface of the arm receiver 14.

When the subject 400 sits in front of the BP apparatus 310 and inserts his or her arm 12 into the arm receiver 14 for a BP measurement, the control device 368 starts to measure, using the sensor 402, the sitting height or shoulder's height of the subject 400. Based on the measured height, the control device 368 operates to adjust the height of the housing 10 so that the longitudinal axis line of the upper arm 12 is substantially aligned with the longitudinal axis line of the arm receiver 14. Assuming that the inclination angle of the arm receiver 14 is constant and the length of the upper arm 12 (i.e. length between the elbow and the shoulder) is constant, the control device 368 can determine, based on the measured sitting or shoulder height of the subject 400, an appropriate height of the housing 10 which ensures that the longitudinal axis line of the upper arm 12 is aligned with the longitudinal axis line of the arm receiver 14. Data or a map representing a prescribed relationship between the sitting (or shoulder's) heights of the subject 400 and the heights of the housing 10 are/is pre-stored in a read only memory (ROM) provided in the control device 368. The control device 368 determines, based on a measured sitting or shoulder's height of the subject 400, a desirable height of the housing 10 according to the prescribed relationship. In the arm-receiver positioning device 399, the sensor 402 indirectly measures the amount of misalignment of the longitudinal axis line of the upper arm 12 from the longitudinal axis line of the receiver 14.

It is to be understood that the BP apparatus 310 may be modified in various manners.

For example, while the BP apparatus 310 adjusts the inclination angle or height of the housing 10 as a whole, it is possible to provide an automatic cuff winding device including the arm receiver 14, cuff 16, belt 18, etc., outside the housing 10, and place the winding device on the housing 10. Alternatively, it is possible to provide an automatic cuff winding device, separately from the housing 10, and place the winding device on the table 338. In the latter cases, the BP apparatus 310 may be adapted to adjust the inclination angle of only the winding device relative to the housing 10 or table 338, or the height of only the winding device from the housing 10 or table 338.

Although the detector 395 shown in FIGS. 21(A), 21(B) includes twelve air chambers 396, it is possible to employ a different number of air chambers 396. For example, the detector 395 may include only the four air chambers 396a, 396g, 396f, 396l provided at the front and rear ends of the arm receiver 14. The detector 395 essentially needs at least one air chamber 396 at the front and rear ends of the receiver 14, respectively, i.e., at least two air chambers 396 in total.

In the BP apparatus 310 shown in FIG. 22, it is possible to replace the sensor 402 with the microswitches 340, 342 or the air chambers 396 and pressure switches 398. On the contrary, in the BP apparatus shown in FIGS. 17–20 or the BP apparatus shown in FIGS. 21(A) and 21(B), it is possible to replace the microswitches 340, 342 or the air chambers 396 and pressure switches 398, with the sensor 402. The sensors 340, 342, 396, 398, 402 may be replaced with other sorts of pressure sensors which detect the pressing of the subject's arm 12.

Although in FIG. 22 the BP apparatus 310 adjusts the height of the housing 10, the apparatus 310 may further include a device for adjusting the height of the table 338 on which the apparatus 310 is placed. In the latter case, the height of the housing 10 can be adjusted.

While the BP apparatus 31C has the detector 340, 342, 396, 398, 402 for detecting a misalignment of the upper arm 12 from the arm receiver 14, only in a vertical plane, and adjusts the vertical misalignment of the upper arm 12, it is possible that the BP apparatus 310 have a horizontal misalignment detector for detecting a misalignment of the upper arm 12 or the arm receiver 14 in a horizontal plane, and a horizontal adjusting device for adjusting the horizontal misalignment of the upper arm 12 or the arm receiver 14. The horizontal misalignment detector may include microswitches provided at the left and right ends of the inner surface 343 of the receiver 14. The horizontal adjusting device may include a device for rotating the housing 10 as a whole, or the automatic cuff winding device 14, 16, 18, about a vertical axis line extending through the elbow rest 344 and perpendicular to the tale 338. In the latter case, the subject is not required to adjust his or her arm 12 relative to the arm receiver 14, also in the horizontal plane.

In the BP apparatus 310, it is possible to omit the third microswitch 346. In the latter case, however, the BP apparatus 310 needs a start key operable for commanding the control device 368 to start, after insertion of the arm 12 into the arm receiver 14, adjusting the position of the receiver 14.

The arm-receiver positioning device 348, 352, 354 shown in FIG. 18, device 377 shown in FIG. 20, or device 399 shown in FIG. 22 may be replaced by other sorts of positioning devices; such as a gear device which includes adjustable legs 348 or 380 each having an axial portion with teeth, i.e., rack portion, a pinion engaged with the rack portion of each leg, and a motor with a reduction gear unit which operates for directly advancing and retracting each leg from and into the housing 10.

Figure 23:
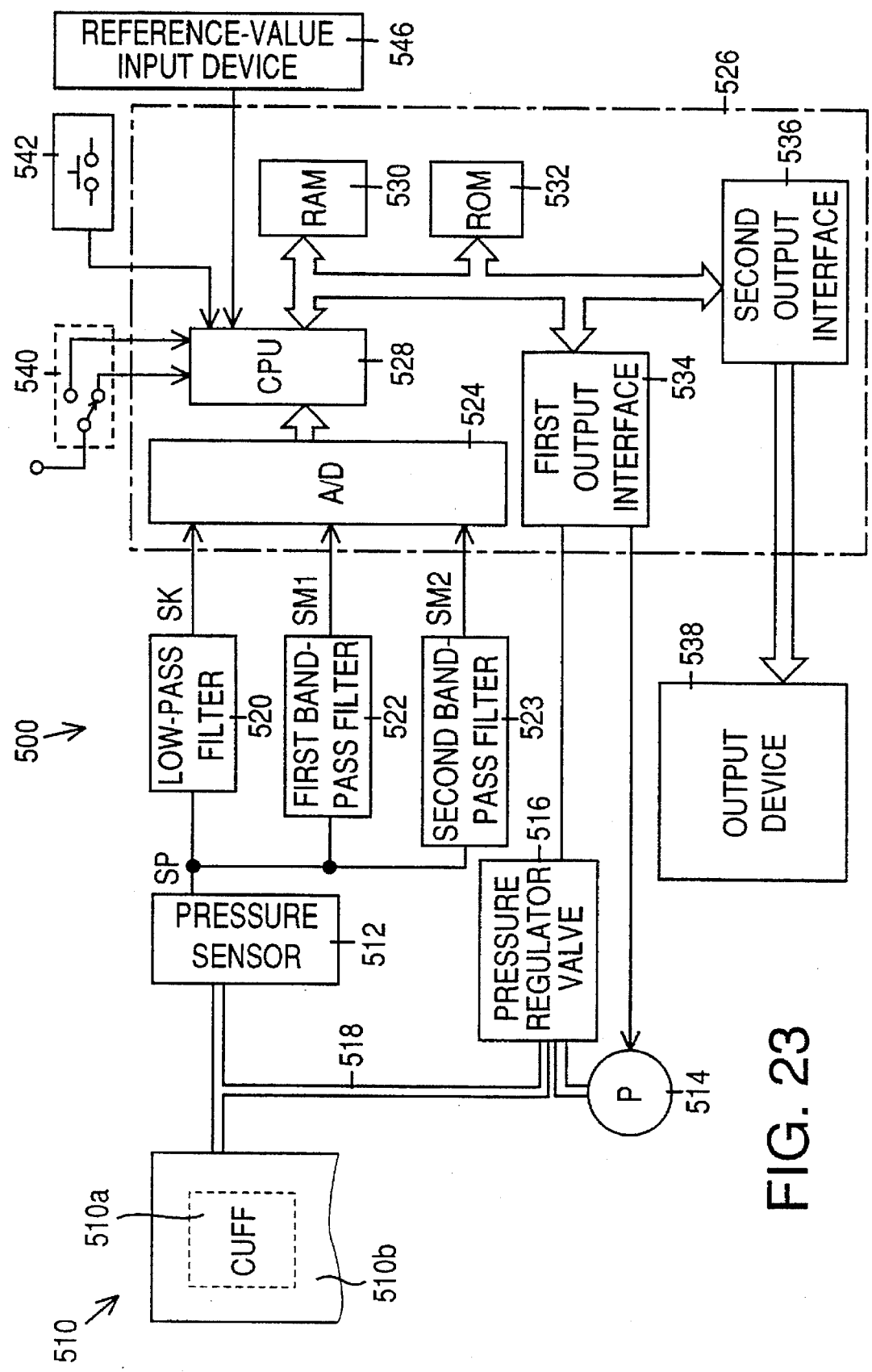
FIG. 23 is a diagrammatic view of a BP monitor apparatus as a fourth embodiment of the present invention.

Referring next to FIG. 23, there is shown a blood pressure (BP) monitor apparatus 500 as a fourth embodiment of the present invention.

In FIG. 23, reference numeral 510 designates an inflatable cuff adapted to be wound around a body portion (e.g., upper arm) of a living subject (e.g., patient) so as to press the upper arm. The cuff 510 includes an inflatable bag 510a formed of an elastic sheet (e.g., rubber sheet or vinyl sheet), and an inextensible arm belt 510b in which the bag 510a is accommodated. The bag 510a of the cuff 510 is connected via piping 518 to a pressure sensor 512, an air pump 514, and a pressure regulator valve 516.

The pressure sensor 512 includes, e.g., a semiconductor pressure sensing element (not shown) which detects an air pressure in the cuff 510 ("cuff pressure") and supplies a detection signal, SP, to a low-pass filter 520, a first band-pass filter 522, and a second band-pass filter 523. The low-pass filter 520 permits only a DC (direct current) or static-pressure component of the detection signal SP to pass therethrough, thereby supplying a cuff-pressure signal, SK, representing the detected static cuff pressure, $P_c$, to an analog-to-digital (A/D) converter 524.

The first band-pass filter 522 permits only a 1 to 10 Hz frequency AC (alternating current) component of the detection signal SP to pass therethrough, thereby supplying a first pulse-wave signal, SM1, representing a pulse wave of the subject, to the A/D converter 524. The pulse wave is produced in the cuff 510 because of the pulsation of arteries of the upper arm under the cuff 510 in synchronism with the heartbeats of the subject, while the cuff pressure $P_c$ is changed within an appropriate pressure range. Thus, the pulse wave produced in the cuff 510 is obtained as the AC component of the detection signal SP supplied from the pressure sensor 512.

The second band-pass filter 523 permits only a 0.5 to 20 Hz frequency AC component of the detection signal SP to pass therethrough, thereby supplying a second pulse-wave signal, SM2, to the A/C converter 524. The first band-pass filter 522 has a narrow frequency range (e.g., 1 to 10 Hz) for obtaining, from the detection signal SP, successive pulse amplitudes free from artifact noise possibly mixed therewith because of physical motion of the subject. Pulse amplitudes are pressure oscillations produced in the cuff 510 in synchronism with the heartbeats of the subject while the cuff pressure $P_c$ is slowly changed at a rate of, e.g., 2 to 3 mmHg/sec in measuring a blood pressure (BP) of the subject. On the other hand, the second band-pass filter 523 has a comparatively wide frequency range (e.g., 0.5 to 20 Hz) for obtaining, from the same signal SP, a pulse wave having a waveform similar to that of a pulse wave which is directly or invasively obtained from inside an artery of the subject. The second band-pass filter 523 is used to obtain the waveform of a pulse wave while the cuff pressure $P_c$ is held at a prescribed value (described later). The A/D converter 524 has a time division multiplexer for time sharing of the three analog signals SK, SM1, SM2, and concurrently converts those analog signals to respective digital signals. In the present embodiment, the first and second band-pass filters 522, 523 serve as a pulse wave detector.

The present BP monitor apparatus 500 has an arithmetic control device 526 which is essentially constituted by a microcomputer including a CPU 528, a RAM 530, a ROM 532, a first output interface 534, and a second output interface 536. The CPU 528 receives the three digital signals SK, SM1, SM2 from the A/D converter 524, and processes those signals by utilizing the temporary-storage function of the RAM 530 and the control programs pre-stored in the ROM 532, so that the CPU 528 controls the operations of the air pump 514 and the regulator valve 516 via the first output interface 534 and controls an output device 538 via the second output interface 536. The output device 538 includes an image display panel (e.g., liquid-crystal panel) which has a number of picture elements and is capable of displaying numerals and curves representing the measured BP values and the detected pulse-wave waveform of the subject. The output device 538 may further include a printer, as needed, which records using an ink numerals and curves on a recording sheet.

A mode switch 540 is manually operable for selecting one of a single-BP-measurement mode and a BP-monitor mode. The mode switch 540 selectively supplies one of a first signal indicative of the single-measurement mode and a second signal indicative of the monitor mode, to the CPU 528. An ON/OFF switch 542 is manually operable for starting and stopping the present BP monitor apparatus 500, and alternatively supplies a START signal and a STOP signal to the CPU 528 upon operation thereof.

Thus, the BP monitor apparatus 500 includes a pulse wave detector (i.e., first and second band-pass filters 522, 523) for detecting, as a pulse wave, a pressure oscillation produced in the cuff 510 wound around a body portion of a living subject, in synchronism with the heartbeats of the subject, while the cuff 510 presses the subject's body portion. The BP monitor apparatus 500 also includes a BP measuring device 508 which determines a BP value of the subject based on the change of pulse amplitudes, $A_m$, which are obtained as the cuff pressure $P_c$ is changed. The BP measuring device 508 includes the elements 510, 512, 514, 516, 518, 520, 522, 523, and 526. The control device 526 or CPU 528 controls the pressure regular valve 516 for repetitively changing and holding the cuff pressure Pc to and at a prescribed pressure value lower than a mean BP value of the subject (hereinafter, this period is referred to as the "operative period"), in each non-BP-measuring period, $T_{2M}$ (FIG. 27), in which the BP measuring device 508 does not operate for a BP measurement. A prescribed non-operative period, $T_{1M}$, is inserted between two successive operation periods. The CPU 528 operates for determining a rate of change, $\theta(=\Delta A_m/\Delta P_c)$, of the pulse amplitudes $A_m$ with respect to the cuff pressure $P_c$. The CPU 528 also operates for identifying, based on the determined rate of change $\theta$, whether the subject is suffering an abnormal blood pressure.

Figure 29:
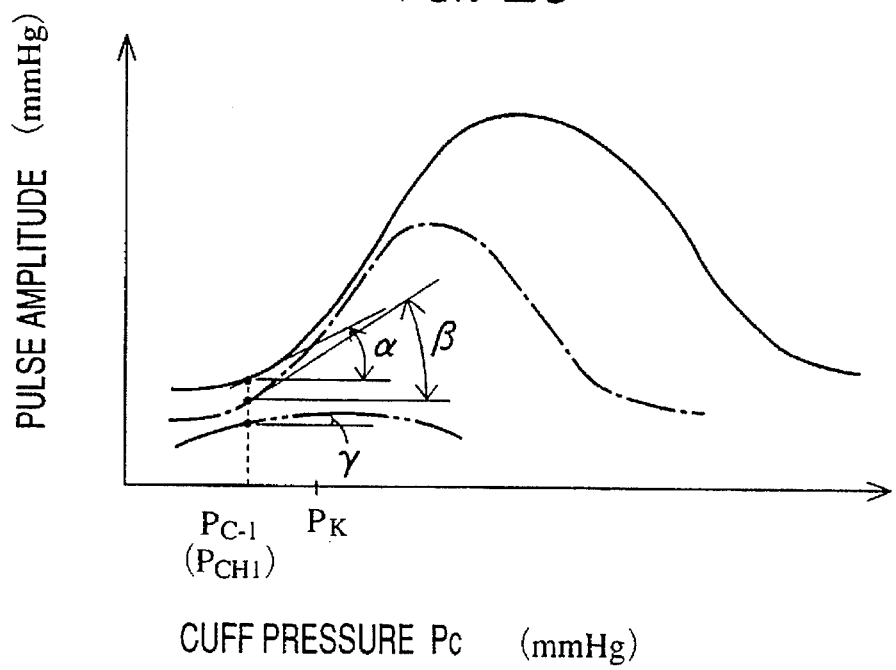
FIG. 29 is a view showing the respective envelopes of pulse amplitudes of a living subject having a normal blood pressure, a subject suffering an abnormally low blood pressure, and a subject being in a shock state.

In the case where the subject has a normal blood pressure, the BP monitor apparatus 500 obtains successive pulse amplitudes whose envelope is shown at solid line in FIG. 29. This envelope has an angle, $\alpha$, approximating a rate of change $\theta$ thereof corresponding to a certain cuff pressure $P_{c-1}$. On the other hand, in the case where the subject is suffering an abnormally low blood pressure, the monitor apparatus 500 obtains successive pulse amplitudes whose envelope is shown at one-dot chain line in FIG. 29. This envelope has an angle, $\beta$, approximating a rate of change $\theta$ thereof corresponding to the same cuff pressure $P_{c-1}$. The angle $\beta$ is significantly greater than the angle $\alpha$, because the respective values of the one-dot-chain-line envelope are slightly smaller than those of the solid-line envelope and simultaneously the upper peak of the former envelope corresponds to a lower cuff pressure than a lower cuff pressure to which the upper peak of the latter envelope corresponds. In view of this fact, the control device 526 or CPU 528 judges that the subject is suffering an abnormally low blood pressure, if the rate of change $\theta$ exceeds a reference value, $\theta_o$. However, if the subject is in the state of shock, the BP apparatus 500 provides successive pulse amplitudes whose envelope is shown at two-dot chain line in FIG. 29. This envelope has an angle, $\gamma$, approximating a rate of change $\theta$ thereof corresponding to the same cuff pressure $P_{c-1}$. The angle $\gamma$ is smaller than the angle $\alpha$. However, the respective values of the two-dot-chain-line envelope are significantly smaller than those of the solid-line envelope. Therefore, the CPU 328 further judges whether a detected pulse amplitude is smaller than a reference amplitude, $Am_o$, and if a positive result or judgment is made the CPU 328 identifies that the subject is suffering an abnormally low blood pressure. When the CPU 528 makes a judgment that the subject has an abnormal blood pressure, the BP measuring device 508 automatically measures a BP value of the subject according to a control program pre-stored in the ROM 532.

The pressure regulator valve 516 is controlled to change the cuff pressure $P_c$ from atmospheric pressure to a prescribed pressure level, $P_{CH}$, so that the first band-pass filter 522 detects a plurality of pulses having different amplitudes $A_m$, and the CPU 528 determines, based on the detected pulse amplitudes $A_m$, a rate of change $\theta$ of the pulse amplitudes $A_m$ with respect to the cuff pressure $P_c$. Thereafter, the regulator valve 516 is controlled to hold the cuff pressure $P_c$ at the prescribed pressure $P_{CH}$ for a prescribed pressure-hold period, $T_{3M}$, so that the band-pass filter 522 detects a pulse wave, or respective pulses of the pulse wave, which are to be utilized for other purposes described below in short and later in detail.

The control device 526 or CPU 528 further judges whether the blood pressure of the subject is abnormal, based on a pulse magnitude $A_m$ detected in a pressure-hold period $T_{3M}$, in a manner described later. When the CPU 528 makes a positive judgment in this manner, the BP measuring device 508 immediately starts to carry out a BP measurement on the subject. Thus, whenever the control device 526 or CPU 528 judges that the subject is suffering an abnormal blood pressure, the BP measuring device 508 measures a BP value of the subject.

In FIG. 23, reference numeral 546 designates an reference-value input device which is manually operable to input or specify the reference values which are to be used by the control device 526 or CPU 528 in judging whether the subject is suffering an abnormal blood pressure. The control device 526 or CPU 528 further functions to change the prescribed pressure value $P_{CH}$, based on the reference values input through the input device 546. When the control device 526 or CPU 528 judges that the subject is suffering an abnormal blood pressure, the output device 538 displays that judgment on the image-display panel thereof.

There will be described the operation of the BP monitor apparatus 500 constructed as described above, by reference to the flow charts of FIGS. 24 and 25. Initially, at Step S101, the CPU 528 judges whether the START/STOP switch 542 has been operated for starting the operation of the present apparatus 500, based on the START or STOP signal supplied from the switch 542. If a negative judgment is made at Step S101, the control of the CPU 528 waits for receiving the START signal from the switch 542. Meanwhile, if a positive judgment is made, the control proceeds with Step S102 to operate the air pump 514 and the pressure regulator valve 516 so as to supply a pressurized air to the inflatable cuff 510 (i.e., bag 510a) and thereby quickly increase the air pressure in the cuff 510, i.e., cuff pressure Pc.

Step S102 is followed by Step S103 to judge whether the cuff pressure $P_c$ has reached a prescribed target pressure, $P_{CM}$ (e.g., 180 mmHg). If a negative judgment is made at Step S103, the CPU 528 repeats Steps S102 and S103. Meanwhile, if a positive judgment is made, the control of the CPU 528 proceeds with Step S104 to stop the air pump 514 and change the degree of opening of the pressure regulator valve 516 so as to slowly deflate the cuff 510, i.e., reduce the cuff pressure $P_c$. This slow cuff deflation is effected at a rate of, e.g., 2 to 3 mmHg/sec suitable for BP measurements. Step S104 is followed by Step S105 to judge whether the CPU 528 has received a length of first pulse wave signal SM1 corresponding to one pulse having an amplitude, i.e., one cycle of heartbeat of the subject. If a negative judgment is made at Step S105, the CPU 528 repeats Steps S104 and S105.

Figure 28:
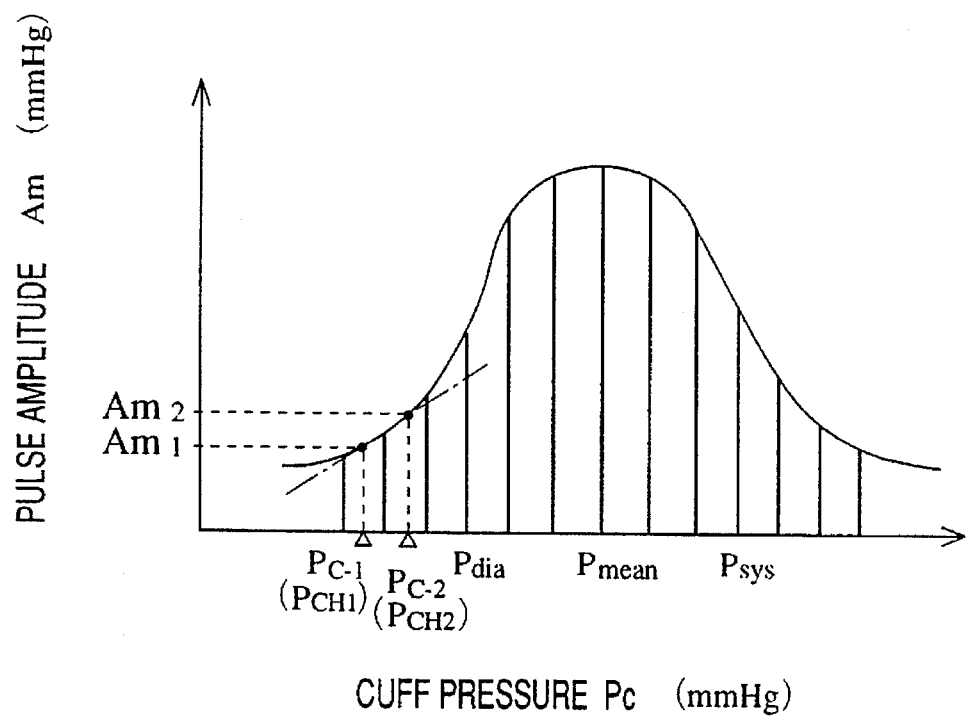
FIG. 28 is a view explaining a manner in which a rate of change $\theta$ of pulse amplitudes $A_m$ with respect to cuff pressures $P_c$ is calculated in a step of the flow chart of FIG. 25.

Meanwhile, if a positive judgment is made at Step S105, the control of the CPU 528 proceeds with Step S106 to operate according to a known oscillometric BP measurement algorithm, i.e., determine the BP values of the subject. Step S106 is followed by Step S107 to judge whether the BP measurement subroutine at Step S106 has been completed. While the cuff pressure $P_c$ is slowly reduced in the BP measuring period, the respective amplitudes of successive pulses of the pulse wave, i.e., pulse wave signal SM1 initially increase and then decrease as shown in FIG. 28. The amplitude of one pulse ("pulse amplitude") is obtained by subtracting the lower-peak magnitude of the one-pulse signal SM1 from the upper-peak of the same. In the known oscillometric BP measurement algorithm, a cuff pressure $P_c$ at the time when the pulse amplitudes significantly greatly increase is determined as a systolic BP value, $P_{sys}$, of the subject; a cuff pressure $P_c$ at the time of detection of the greatest pulse amplitude is determined as a mean BP value, $P_{mean}$; and a cuff pressure $P_c$ at the time when the pulse amplitudes significantly greatly decrease is determined as a diastolic BP value, $P_{dia}$.

If a negative judgment is made at Step S107, the CPU 528 repeats Steps S104 through S107. Meanwhile, if a positive judgment is made at Step S107, the control of the CPU 528 proceeds with Step S108 to store the three BP values $P_{sys}$, $P_{mean}$, $P_{dia}$ in the RAM 530 and display those BP values in digits on the image-display panel of the output device 538. At the following Step S109, the CPU 528 fully opens the pressure regulator valve 516 so as to quickly deflate the cuff 510, i.e., quickly decrease the cuff pressure $P_c$ and thereby release the subject's upper arm from the cuff pressure $P_c$. In the present embodiment, Steps S102 to S109 serve as a part of the BP measuring device 508 that automatically carries out a BP measurement in a series of prescribed steps.

Figure 26:
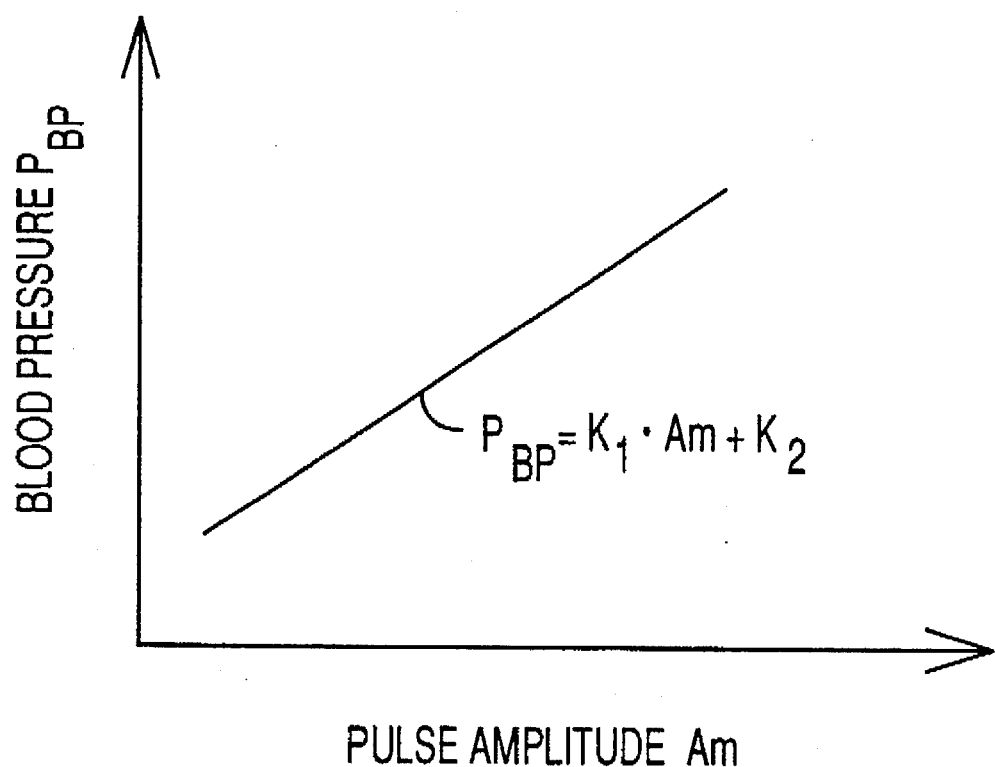
FIG. 26 is a view showing a linear function defining a relationship between pulse amplitude and blood pressure, the function being determined in a step of the flow chart of FIG. 24.

Step S109 is followed by Step S110 to determine a relationship between BP values, $P_{BP}$, and pulse amplitudes $A_m$ which relationship is utilized at Step S124 described later. Specifically, the CPU 528 determines a first $P_{BP}$-$A_m$ relationship based on the BP value $P_{sys}$ and the pulse amplitude $A_m$ corresponding to the cuff pressure $P_c$ determined as the BP value $P_{sys}$, and a second $P_{BP}$-$A_m$ relationship based on the BP value $P_{dia}$ and the pulse amplitude $A_m$ corresponding to the cuff pressure $P_c$ determined as the BP value $P_{dia}$. The first or second $P_{BP}$-$A_m$ relationship may be defined by the following linear expression: $P_{BP}=K_1 \times A_m+K_2$, where $K_1$ and $K_2$ are constants, as shown in FIG. 26. This linear expression defines a $P_{BP}$-$A_m$ relationship proper to the specific living subject. The constant $K_2$ may be a prescribed value, or zero.

At the following Step S111, the CPU 528 judges whether the BP monitor apparatus 500 is currently placed in the BP-monitor mode, based on a mode signal supplied from the mode switch 540. If a negative judgment is made at Step S111, that is, if the apparatus 500 is currently placed in the single-BP-measurement mode, the current control cycle of the CPU 528 in accordance with this main routine is ended, and the control of the CPU 528 returns to Step S101 and the following steps. On the other hand, if a positive judgment is made at Step S111, that is, if the apparatus 500 is currently placed in the BP-monitor mode, the control of the CPU 528 goes to Step S112 and the following steps, i.e., BP monitor subroutine. The CPU 528 repeats Steps S113 through S128 at a prescribed period of time, $T_{1M}$ (e.g., 1 to 3 minutes).

At Steps S112 and S113, the CPU 528 clears the contents of a second and a first time counter (i.e., timers) T2 and T1, respectively. Step S113 is followed by Step S114 to increment the contents of the two timers T1, T2 each by one, i.e., T1←T1+1 and T2←T2+1. At the following Step S115, the CPU 528 judges whether the contents of the first timer T1 has reached the prescribed time period $T_{1M}$. Each time the first timer T1 counts up the reference time $T_{1M}$, the CPU 528 controls the air pump 514 and the regulator valve 516 to increase the cuff pressure $P_c$ up to the hold pressure $P_{CH}$ so as to monitor the blood pressure of the subject.

Shortly after the beginning of the BP monitor operation, negative judgments are made at Step S115, so that the CPU 528 repeats Steps S114 and S115. Meanwhile, if a positive judgment is made at Step S115, the control of the CPU 528 proceeds with Step S116 to operate the air pump 514 and the regulator valve 516 to slowly increase the cuff pressure $P_c$. The rate of increasing of the cuff pressure $P_c$ is predetermined at, e.g., 3 mmHg/sec so that the BP monitor apparatus 500 can obtain at least three pulses before the cuff pressure $P_c$ is raised up to the hold pressure $P_{CH}$.

Step S116 is followed by Step S117 to detect each pulse which occurs during the slow increasing of the cuff pressure $P_c$ and store the amplitude $A_m$ of each detected pulse in an appropriate area of the RAM 530. In addition, the CPU 528 determines a straight line approximating the detected at least three pulse amplitudes $A_m$. As shown in FIG. 28, this straight line fits to a low-pressure-side portion of the envelope of the subject's pulse amplitudes $A_m$ obtained in the BP measuring period at Step S106. On the approximation line, the CPU 528 determines a rate of change $\theta(=\Delta A_m/\Delta P_c)$ of the pulse amplitudes $A_m$ with respect to the cuff pressure $P_c$, based on prescribed cuff pressure values $P_{c-1}$ and $P_{c-2}$, according to the following expression (1):

$$\theta=(A_{m2}-A_{m1})/(P_{c-2}-P_{c-1}) \quad (1)$$

where $A_{m1}$ and $A_{m2}$ are respective pulse amplitudes corresponding to the cuff pressure values $P_{c-1}$, $P_{c-2}$ on the approximation line.

In the present embodiment, Step S117 and a portion of the control device 526 for carrying out this step cooperate with each other to serve as means for determining a rate of change of pulse amplitudes $A_m$ with respect to cuff pressure $P_c$.

Step S117 is followed by Step S118 to judge whether the determined rate of change $\theta$ is greater than a reference value $\theta_0$. The reference value $\theta_0$ corresponds to the angle $\beta$ obtained on the low-pressure-side portion of the envelope (indicated at one-dot-chain line in FIG. 29) of the pulse amplitudes of a living subject suffering abnormally low blood pressure values, e.g., 90 mmHg systolic BP value and 50 mmHg diastolic BP value. If a positive judgment is made at Step S118, the control of the CPU 528 goes to Step S119 to operate the output device 438 to indicate that the subject's blood pressure is abnormal. Following Step S119, the control of the CPU 528 returns to Step S102 and the following steps to immediately measure a BP value of the subject at the time of identification of the subject's BP abnormality.

On the other hand, if a negative judgment is made at Step S118, the control of the CPU 528 goes to Step S120 to judge whether each pulse amplitude $A_m$ is greater than a reference value $A_{m0}$. The reference value $A_{m0}$ corresponds to the angle $\gamma$ obtained on the low-pressure-side portion of the envelope (indicated at two-dot-chain line in FIG. 29) of the pulse amplitudes of a living subject who is currently in the state of shock. If a negative judgment is made at Step S120, the control of the CPU 528 goes to Step S119 to control the output device 438 to indicate that the subject is in the state of shock. Following Step S119, the control of the CPU 528 returns to Step S102 and the following steps to immediately measure a BP value of the subject at the time of identification of the subject's shock state. In the present embodiment, Steps S118 and S120 and a portion of the control device for carrying out these steps cooperate with each other to serve as first abnormality judging means for identifying a blood pressure abnormality of a living subject.

On the other hand, if a positive judgment is made at Step S120, the control of the CPU 528 goes to Step S121 to judge whether the cuff pressure $P_c$ has reached the prescribed hold pressure $P_{CH}$. The hold pressure $P_{CH}$ is pre-determined to fall within a range of 20 to 30 mmHg which is adequately lower than the mean BP value $P_{mean}$ of the subject and which ensures that the BP monitor apparatus 500 detects a time change of the pulse amplitudes $A_m$. If a negative judgment is made at Step S121, the control of the CPU 528 goes back to Step S116 and the following steps. Meanwhile, if a positive judgment is made, the control goes to Step S122 to stop the slow increasing of the cuff pressure $P_c$ and temporarily hold the cuff pressure $P_c$ at the hold pressure $P_{CH}$ for the prescribed pressure-hold period $T_{3M}$, for example, 2 seconds.

Step S122 is followed by Step S123 to read in a pulse $A_{mh}$ detected while the cuff pressure $P_c$ is held at the hold pressure $P_{CH}$. At the following Step S124, the CPU 528 estimates a systolic and a diastolic BP value, $P_{sysE}$ and $P_{diaE}$, of the subject, based on the read-in pulse amplitude $A_{mh}$, according to the first and second PBP-Am relationships determined at Step S110.

At the following Step S125, the CPU 528 judges whether the estimated systolic BP value $P_{sysE}$ is smaller than a reference value, $P_{sysE0}$, or whether the estimated diastolic BP value $P_{diaE}$ is smaller than a reference value, $P_{diaE0}$. These reference values $P_{sysE0}$, $P_{diaE0}$ are employed for monitoring an abnormal decrease or fall of the blood pressure of the subject, and are pre-determined at, e.g., 90 mmHg and 50 mmHg, respectively. If a positive judgment is made with respect to at least one of the two questions at Step S125, the control of the CPU 528 goes to Step S126 to operate the output device 538 to indicate an abnormal decrease of the subject's blood pressure. Then, the control of the CPU 528 returns to Step S102 and the following steps to measure a BP value of the subject at the time of detection of the abnormal BP decrease.

On the other hand, if a negative judgement is made with respect to both the two questions of Step S125, the control of the CPU 528 goes to Step S127 to deflate the cuff 510, i.e., reduce the cuff pressure $P_c$ to atmospheric pressure, thereby releasing the subject's upper arm from the pressing of the cuff 510 held at the hold pressure $P_{CH}$. Step S127 is followed by Step S128 to judge whether the contents of the second timer T2 has reached a prescribed reference value $T_{2M}$. This reference value $T_{2M}$ is a regular interval of time at which the control device 526 periodically carries out Steps S102 and the following steps, and is pre-selected at a time of 10 to 30 minutes. Shortly after the beginning of the BP monitor operation, negative judgments are made at Step S128, so that the CPU 528 carries out Steps S113 and the following steps. Meanwhile, if a positive judgment is made at Step S128, the control of the CPU 528 goes back to Step S102 and the following steps.

Figure 24:
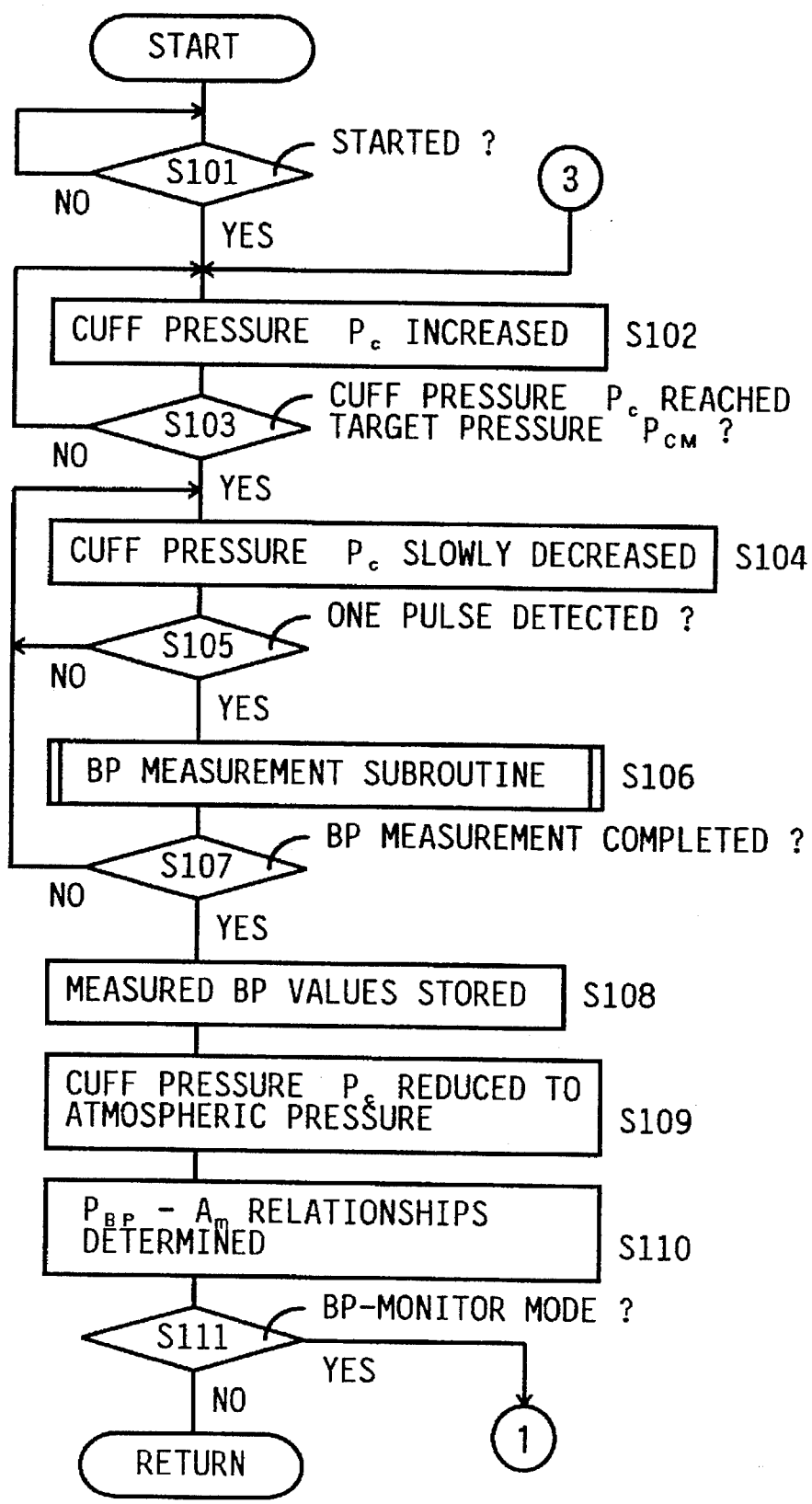
FIG. 24 is a flow chart representing a first half of a control program according to which the apparatus of FIG. 23 operates.
Figure 25:
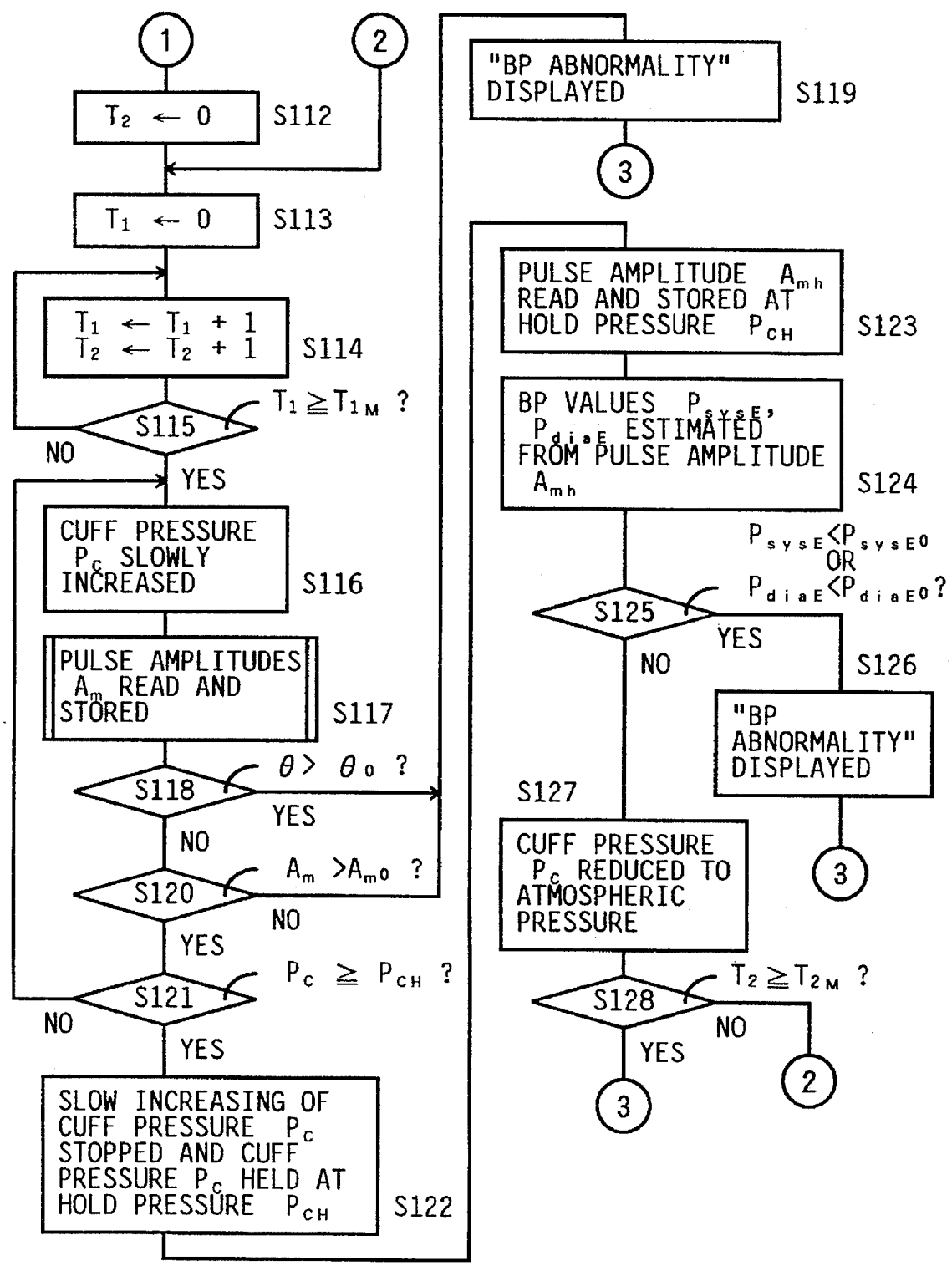
FIG. 25 is a flow chart representing a second half of the control program of FIG. 24.
Figure 27:
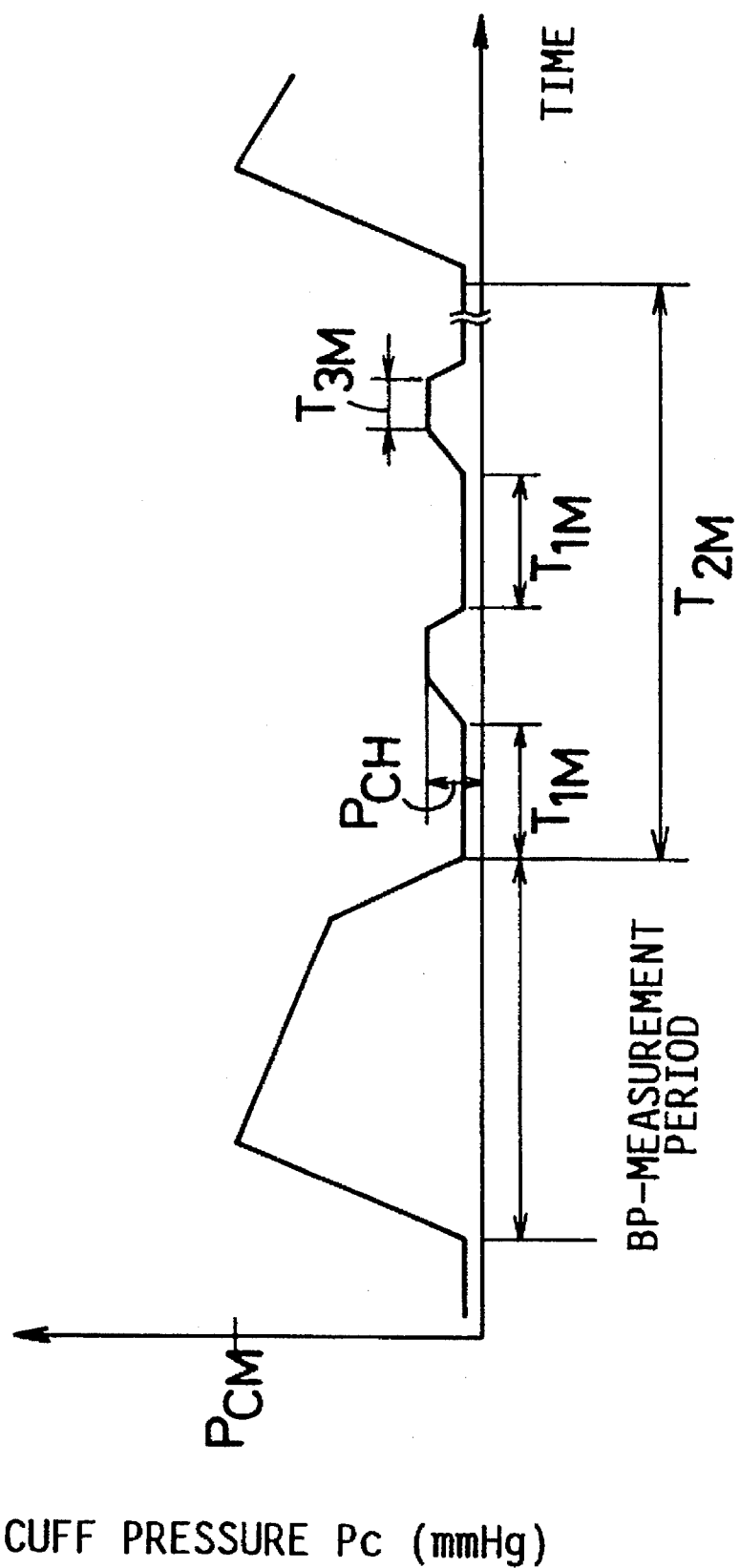
FIG. 27 is a time chart representing the time change of cuff pressure $P_c$ when the monitor apparatus of FIG. 23 operates according to the flow charts of FIGS. 24 and 25.

When the BP monitor apparatus 500 is operated according to the flow charts of FIGS. 24 and 25, the cuff pressure $P_c$ changes as shown in FIG. 27. In the BP monitor period, i.e., non-BP-measuring period following the BP-measuring period effected in response to the starting operation of the ON/OFF switch 540, the CPU 528 periodically operates for slowly increasing the cuff pressure $P_c$ up to the prescribed hold pressure $P_{CH}$, while alternately inserting the prescribed interval time $T_{1M}$ between successive two pressure-hold periods $T_{3M}$. The CPU 528 determines a rate of change $\theta$ of the pulse amplitudes $A_m$ obtained during the slow increasing of the cuff pressure $P_c$, and judges, based on the determined rate of change $\theta$, whether the subject is suffering an abnormally low blood pressure. In addition, the CPU 528 judges whether the subject is suffering an abnormal blood pressure decrease or fall because of being in the state of shock. Furthermore, the CPU 528 estimates, based on the pulse amplitude $A_{mh}$ detected during the pressure-hold period $T_{3M}$, the systolic and diastolic BP values $P_{sysE}$, $P_{diaE}$ and judges whether the subject is suffering an abnormally low blood pressure, based on the estimated BP values $P_{sysE}$, $P_{diaE}$.

It emerges from the foregoing description that in the fourth embodiment, the CPU 528 determines a rate of change $\theta$ of the pulse amplitudes $A_m$ with respect to the cuff pressure $P_c$, each time the CPU 528 operates the air pump 514 and regulator valve 516 to slowly increase, following a prescribed interval $T_{1M}$, the cuff pressure $P_c$ from atmospheric pressure to the prescribed pressure $P_{CH}$ lower than the mean BP value $P_{mean}$ of a living subject. The CPU 528 judges, based on the determined rate of change $\theta$, whether the subject is suffering a blood pressure abnormality. Thus, in the present embodiment, the BP monitor apparatus 500 utilizes, for monitoring the blood pressure of the subject, the phenomenon that the rate of change $\theta$ of the low-pressure-side portion of the envelope representing the change of the pulse amplitudes $A_m$ with respect to the cuff pressure $P_c$, changes as the blood pressure of the subject changes. Therefore, the BP monitoring of the apparatus 500 is carried out with high reliability. Since the rate of change $\theta$ is determined based on the data obtained while the cuff pressure $P_c$ is changed in a low pressure range from atmospheric pressure to the hold pressure $P_{CH}$, the BP monitor operation of the apparatus 500 does not cause the subject to feel discomfort due to the pressing of the inflated cuff 510.

Furthermore, the BP measuring device 508 automatically measures BP values of the subject in a series of prescribed steps, each time the control device 526 or CPU 528 identifies that the subject is suffering a blood pressure abnormality. Thus, the BP measuring device 528 reliably measures the BP values of the subject immediately after the identification of the blood pressure abnormality. The thus obtained BP values of the subject ensure that medical workers such as doctors make appropriate treatments with the subject.

When a living subject is in a shock state, the envelope representing the change of the pulse amplitude $A_m$ with respect to the cuff pressure $P_c$, becomes more or less flat. Therefore, in this case, it is very difficult for the BP apparatus 500 to make an abnormality judgment based on the rate of change $\theta$ of the pulse amplitude $A_m$ with respect to the cuff pressure $P_c$. However, the CPU 528 also judges whether the pulse amplitude $A_m$ detected during the slow increasing of the cuff pressure $P_c$ is smaller than the reference value $A_{m0}$. If the pulse amplitude $A_m$ is smaller than the reference value $A_{m0}$, the CPU 528 judges that the subject is suffering an abnormal blood pressure fall, thereby easily identifying that the subject is in the state of shock.

In the BP monitor apparatus 500, the control device 526 or CPU 528 controls the air pump 514 and the pressure regulator valve 516 to change the cuff pressure $P_c$ to the prescribed hold pressure $P_{CH}$ and then hold the cuff pressure $P_c$ at the pressure level $P_{CH}$ for the prescribed period $T_{3M}$. Based on the pulse amplitude $A_{mh}$ obtained during the pressure-hold period $T_{3M}$, the CPU 528 finds the subject's blood pressure abnormality. Therefore, the BP monitoring of the present apparatus 500 is carried out with high reliability.

Thus, in the present embodiment, whenever the control device 526 or CPU 528 finds a blood pressure abnormality of a living subject, the BP measuring device 508 automatically measures BP values of the subject. Therefore, the reliability of the BP monitoring of the apparatus 500 is improved as such.

It is to be understood that the BP monitor apparatus 500 may be modified in various ways.

Figure 30:
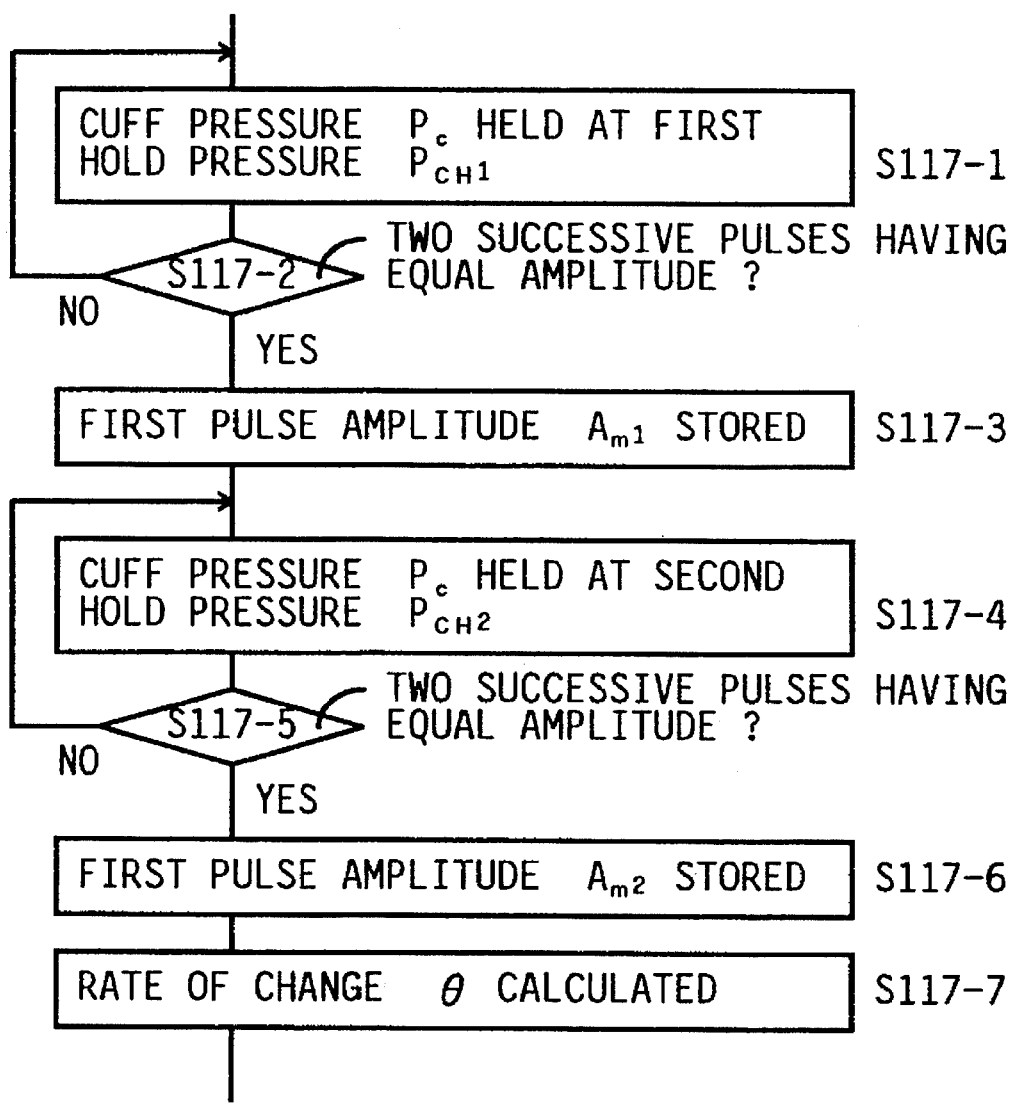
FIG. 30 is a flow chart representing steps which may be carried out in place of Step S117 of FIG. 25 by the monitor apparatus of FIG. 23.

For example, FIG. 30 shows a flow chart representing steps which may be carried out in place of Step S117 of FIG. 25 by the control device 526 or CPU 528. The steps of FIG. 30 serve as a subroutine for determining a rate of change $\theta$ of pulse amplitudes $A_m$.

At Step S117-1, the CPU 528 controls the air pump 514 and the regulator valve 516 to hold the cuff pressure $P_c$ at a first hold pressure $P_{CH1}$. The first hold pressure $P_{CH1}$ is pre-selected at a value which ensures that the monitor apparatus 500 obtains pulse amplitudes $A_m$ suitable for determining a rate of change $\theta$ of the pulse amplitudes $A_m$ on the low-pressure-side portion of the envelope of the pulse amplitudes $A_m$ shown in FIG. 28, and may be pre-determined to fall within a range of 15 to 20 mmHg. Step S117-1 is followed by Step S117-2 to judge whether the respective amplitudes of two successive pulses are substantially equal to each other. This step is provided for the purpose of discarding noise. Since the cuff pressure $P_c$ is not changed at Step S117-2 (and also at Step S117-5 (described later)), the CPU 528 reads in the second pulse wave signal SM2 that has been filtered through the second band-pass filter 523 and is more accurate than the first pulse wave signal SM1. If a negative judgment is made at Step S117-2, the CPU 528 repeats Steps S117-1 and S117-2. On the other hand, if a positive judgment is made at Step S117-2, the control of the CPU 528 proceeds with Step S117-3 to store, as a first pulse amplitude, $A_{m1}$, the two pulse amplitudes substantially equal to each other, in the RAM 530.

At the following Step S117-4, the CPU 528 controls the air pump 514 and the regulator valve 516 to increase and hold the cuff pressure $P_c$ to and at a second hold pressure $P_{CH2}$. The second hold pressure $P_{CH2}$ is pre-selected at a value which ensures that the monitor apparatus 500 obtains pulse amplitudes $A_m$ greater than the pulse amplitude Am1 stored at Step S117-3 and suitable for determining the rate of change $\theta$ on the low-pressure-side portion of the envelope of the pulse amplitudes $A_m$ shown in FIG. 28, and may be pre-determined to fall within a range of 25 to 30 mmHg. Step S117-4 is followed by Step S117-5 to judge whether the respective amplitudes of two successive pulses are substantially equal to each other. If a negative judgment is made at Step S117-2, the CPU 528 repeats Steps S117-4 and S117-5. On the other hand, if a positive judgment is made at Step S117-5, the control proceeds with Step S117-6 to store, as a second pulse amplitude, $A_{m2}$, the two pulse amplitudes substantially equal to each other, in the RAM 530.

At the following Step S117-7, the CPU 528 calculates the rate of change $\theta$ from the first and second hold pressure values $P_{CH1}$, $P_{CH2}$ and the first and second pulse amplitude values $A_{m1}$, $A_{m2}$, according to the following expression (2):

$$\theta=(A_{m2}-A_{m1})/(P_{CH2}-P_{CH1}) \qquad (2)$$

Figure 31:
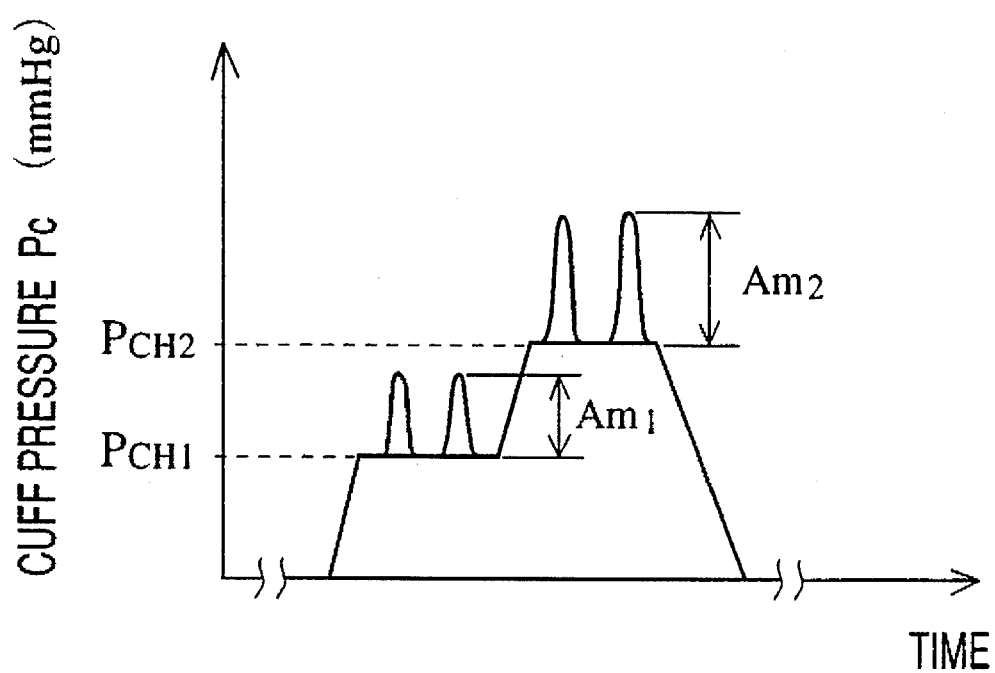
FIG. 31 is a time chart representing the time change of cuff pressure $P_c$ when the monitor apparatus of FIG. 23 operates according to the flow chart of FIG. 30.

FIG. 31 shows a time change of cuff pressure $P_c$ when the monitor apparatus 500 operates according to the flow chart of FIG. 30. Specifically described, the cuff pressure $P_c$ is stepwise increased up to the first hold pressure $P_{CH1}$, and the first hold pressure $P_{CH1}$ is maintained until two successive pulses having equal amplitudes are obtained and the first pulse amplitude $A_{m1}$ is stored. Subsequently, the cuff pressure $P_c$ is stepwise increased from the first hold pressure $P_{CH1}$ to the second hold pressure $P_{CH2}$, and the second hold pressure $P_{CH2}$ is maintained until two successive pulses having equal amplitudes are obtained and the second pulse amplitude $A_{m2}$ is stored. The second hold pressure $P_{CH2}$ may be equal to the hold pressure $P_{CH}$ used as a reference pressure value at Step S121 of FIG. 25. In the latter case, Steps S121 and S122 are omitted from the flow chart of FIG. 25, and at Step S124 the CPU 528 estimates, based on the second pulse amplitude $A_{m2}$, the systolic and diastolic BP values $P_{sysE}$, $P_{diaE}$ of the subject.

This modified control manner enjoys the same advantages as those with the control manner in accordance with the flow charts of FIGS. 24 and 25. Additionally, since the rate of change $\theta$ of the low-pressure-side increasing portion of the pulse-amplitude envelope is calculated based on the first and second pulse amplitudes $A_{m1}$, $A_{m2}$ obtained at the prescribed first and second hold pressures $P_{CH1}$, $P_{CH2}$, the calculated rate of change $\theta$ enjoys a high accuracy and accordingly the accuracy of monitoring of the present apparatus 500 is improved. Moreover, since the apparatus 500 stores and utilizes the equal amplitude of two successive pulses obtained at the prescribed cuff pressure $P_{CH1}$ or $P_{CH2}$, noise which is possibly mixed with heartbeat-synchronous pulses can effectively be removed or omitted, so that the accuracy of monitoring of the apparatus 500 is more improved. Furthermore, in the case where the second hold pressure $P_{CH2}$ is equal to the hold pressure $P_{CH}$, the second pulse amplitude Am2 may be used for identifying a subject's blood pressure abnormality at Step S124 of FIG. 25. Thus, the pressure-hold periods $T_{3M}$ and Steps S121 and S122 may be omitted.

Figure 32:
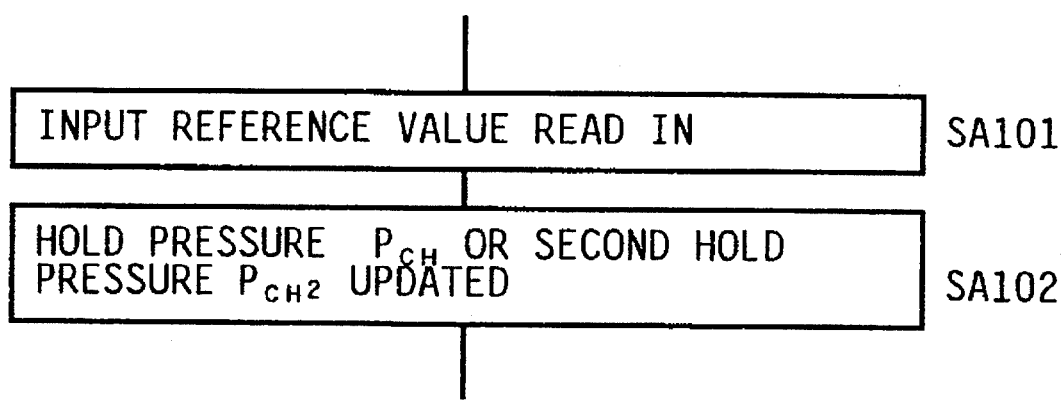
FIG. 32 is a flow chart representing steps which may be carried out in addition to the steps of FIGS. 24 and 25 by the monitor apparatus of FIG. 23.
Figure 33:
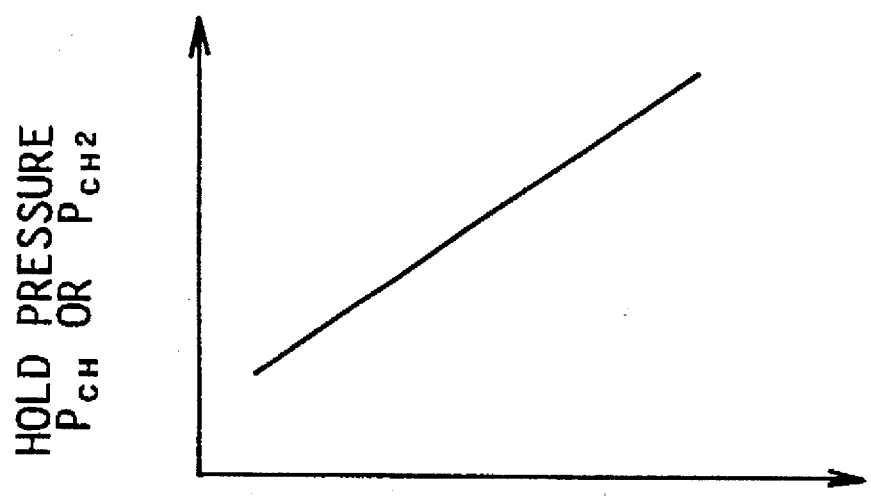
FIG. 33 is a view showing a relationship which is utilized in a step of the flow chart of FIG. 32.

FIG. 32 shows a flow chart including steps which may be carried out in addition to the steps of the flow charts of FIGS. 24 and 25 by the monitor apparatus 500. According to this flow chart, the control device 526 or CPU 528 changes the hold pressure $P_{CH}$ or the second hold pressure $P_{CH2}$ based on a reference value $\theta_0$, or reference value $P_{sysE0}$ or $P_{diaE0}$, which is input through operation of the reference-value input device 546. The input device 546 has three keys for inputting or specifying a reference value $\theta_0$, a reference value $P_{sysE0}$, and a reference value $P_{diaE0}$, respectively, each of which is selected by a medical worker such as a doctor. At Step SA101, the CPU 528 reads in a reference value $\theta_0$, $P_{sysE0}$, $P_{diaE0}$ input through the input device 546, and updates the prior reference value $\theta_0$, $P_{sysE0}$, $P_{diaE0}$ stored in the RAM 530, by replacing the prior value with the newly input value. Step SA101 is followed by Step SA102 to determine a new hold pressure $P_{CH}$ or a new second hold pressure $P_{CH2}$, based on the new reference value $\theta_0$, $P_{sysE0}$, $P_{diaE0}$, according to a map shown in FIG. 33. This map defines a prescribed relationship between reference value $\theta_0$, $P_{sysE0}$, or $P_{diaE0}$ and hold pressure $P_{CH}$ or $P_{CH2}$. Although only a single map is shown in FIG. 33, three different maps are, in fact, used for respective relationships between three sorts of reference values $\theta_0$, $P_{sysE0}$, $P_{diaE0}$ and hold pressure $P_{CH}$ (or second hold pressure $P_{CH2}$). In this modified control manner, Step SA102 and a portion of the control device 526 for carrying out this step cooperate with each other to serve as means for changing the hold pressure $P_{CH}$ or second hold pressure $P_{CH2}$. This modified control manner enjoys the advantage that the hold pressure $P_{CH}$ or second hold pressure $P_{CH2}$ is made as low as possible and accordingly the discomfort which the subject may feel due to the cuff pressure $P_c$ in the BP monitor mode is minimized.

Although in the fourth embodiment the rate of change $\theta$ of pulse amplitudes $A_m$ with respect to cuff pressure $P_c$ is determined according to the expression (1) or (2), it is possible to determine, as a rate of change $\theta$, a maximum rate of change, $(dA_m/dP_c)_{max}$, of an increasing portion of the pulse-amplitude envelope shown in FIG. 28 which portion is defined as a portion from the smallest pulse amplitude (i.e., lower peak) to the greatest pulse amplitude (i.e., upper peak).

While the BP monitor apparatus 500 holds the cuff pressure $P_c$ at the hold pressure $P_{CH}$ in each pressure-hold period $T_{3M}$, it is possible to omit the pressure-hold periods $T_{3M}$. That is, the BP monitor apparatus 500 may be modified not to operate for identifying a subject's blood pressure abnormality based on a pulse amplitude obtained in each pressure-hold period $T_{3M}$.

In the case where the hold pressure $P_{CH}$ or the second hold pressure $P_{CH2}$ is pre-selected at a prescribed value, the prescribed value is by no means limited to the exemplified pressure range of 20 to 30 mmHg, but may be selected with some effect at any value lower than a mean BP value $P_{mean}$ of a living subject. The prescribed value may be selected at a value lower than a diastolic BP value $P_{dia}$ of the subject, with more effect, because the blood flow of the subject is not stopped under the cuff pressure $P_c$ held at the selected value.

While the monitor apparatus 500 obtains a pulse wave, i.e., respective pulses of the pulse wave via the first or second band-pass filter 522, 523 from the blood pressure cuff 510, it is possible to employ another cuff or inflatable bag different from the cuff 510 and detect a pulse wave as a pressure oscillation produced in the different cuff or bag.

Figure 34:
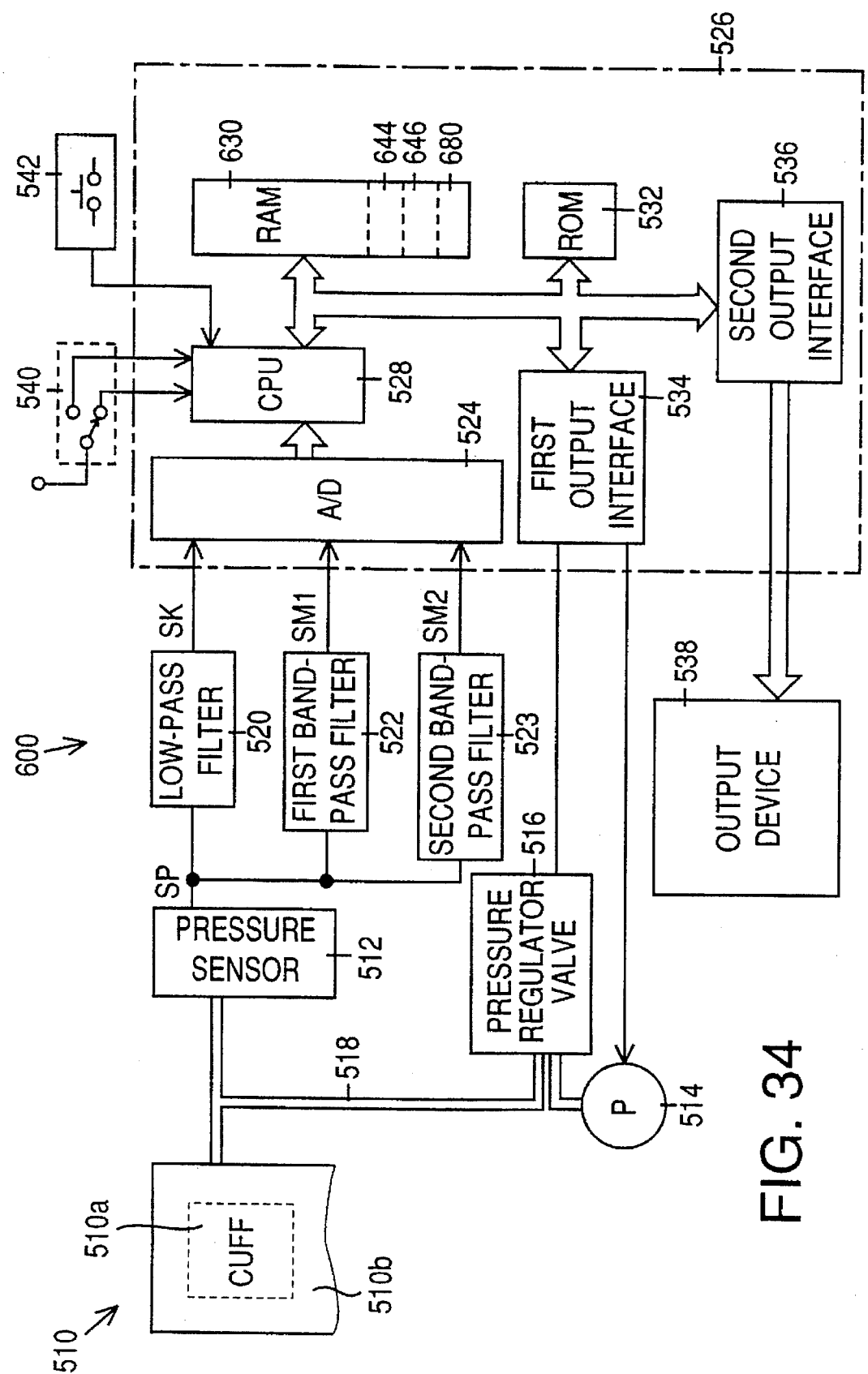
FIG. 34 is a diagrammatic view of a BP measuring apparatus as a fifth embodiment of the present invention.

Referring next to FIG. 34, there is shown an automatic blood pressure (BP) measuring apparatus 600 as a fifth embodiment of the present invention. The BP measuring apparatus 600 has the function of estimating a blood pressure value of a living subject.

The BP measuring apparatus 600 has a construction similar to that of the BP monitor apparatus 500 shown in FIG. 23. Therefore, the same reference numerals as used in FIG. 23 are used to designate the corresponding elements or parts of the BP apparatus 600 shown in FIG. 34, and the description of those elements or parts is omitted. However, the BP apparatus 600 does not have the reference-value input device 546, and has a RAM 630 having three memory areas 644, 646, 680 (described later), in place of the RAM 530.

The BP measuring apparatus 500 includes a pressure sensor 512 and a low-pass filter 520 which provide a static pressure in an inflatable cuff 510 ("cuff pressure $P_c$") wound around a body portion (e.g., upper arm) of a living subject; a BP measuring device 508 which determines a BP value or values of the subject based on the change of respective amplitudes of pulses of a pulse wave as a pressure oscillation produced in the cuff 510 while the cuff pressure $P_c$ is slowly decreased; and an electric air pump 514 and a pressure regulator valve 516 which are controlled to start a BP measuring operation by quickly increasing the cuff pressure $P_c$ up to a target pressure, $P_{CM}$, and subsequently slowly decreasing the same $P_c$ from the target pressure $P_{CM}$, and to reduce the cuff pressure $P_c$ down to atmospheric pressure after a BP value or values of the subject has or have been determined during the slow decreasing of the cuff pressure $P_c$. A first band-pass filter 522 provides a waveform of a pulse of a pulse wave ("pulse waveform") produced in the cuff 510 while the cuff pressure $P_c$ is quickly increased. An arithmetic and control device 526 or a CPU 528 thereof operates for determining, based on (a) the pulse waveform provided by the band-pass filter 523 during the BP measuring operation of the BP measuring device 508 and (b) the BP value or values determined by the BP measuring device 508, a relationship between pulse waveform, cuff pressure $P_c$, and blood pressure which relationship is proper to the living subject. The control device 526 or CPU 528 additionally functions for estimating, according to the thus determined relationship, a BP value or values of the subject, based on (a) a pulse waveform actually supplied from the first band-pass filter 522 and (b) a cuff pressure $P_c$ at the time of supplying of the pulse waveform.

Figure 35A:
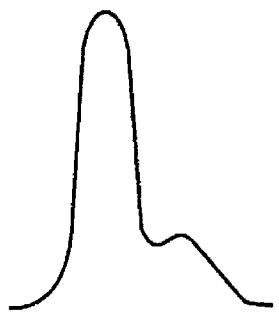
FIG. 35(A) is a view showing an example of a pulse waveform obtained from a cuff wound around a body portion of a living subject when the cuff pressure is taking a value around a systolic blood pressure of the subject.
Figure 35B:
FIG. 35(B) is a view showing a pulse waveform obtained from the cuff when the cuff pressure is taking a value around a mean blood pressure of the subject.
Figure 35C:
FIG. 35(C) is a view showing a pulse waveform obtained from the cuff when the cuff pressure is taking a value around a diastolic blood pressure of the subject.

The waveform of one pulse of a pulse wave produced in the form of a pressure oscillation in the cuff 510 in synchronism with one cycle of heartbeat of a living subject, changes as the cuff pressure $P_c$ changes from a value around a systolic BP value, $P_{sys}$, of the subject, to a value around a mean blood pressure $P_{mean}$ of the same, and to a diastolic BP value, $P_{dia}$, of the same. FIGS. 35(A), 35(B), and 35(C) shows three waveforms of one pulse obtained at three cuff pressure values $P_c$ generally corresponding to systolic, mean, and diastolic BP values $P_{sys}$, $P_{mean}$, $P_{dia}$, respectively. As can be understood from the three waveforms shown in FIGS. 35(A), 35(B), and 35(C), the changing of a pulse waveform means that various characteristics of the pulse waveform change. Those waveform characteristics include a maximum slope of an increasing portion of the pulse waveform obtained in a time period, $T_{ds}$ (FIG. 39); a height of a primary peak of the pulse waveform, i.e., pulse amplitude; a position and a shape of a secondary peak of the pulse waveform, etc. Therefore, the CPU 528 determines in advance a relationship between (a) evaluated values of a waveform characteristic, (b) values of cuff pressure $P_c$, and (c) values of blood pressure and estimates, according to the relationship, a BP value of the subject based on an evaluated value of a characteristic of a pulse waveform actually supplied during the quick increasing of the cuff pressure $P_c$ and a cuff pressure value $P_c$ at the time of supplying of the pulse waveform.

In addition, the control device 526 or CPU 528 operates for determining, based on an estimated BP value of the subject, a target pressure value $P_{CM}$ to which the cuff pressure $P_c$ is quickly increased for a BP measurement. The CPU 528 controls the air pump 514 and the pressure regulator valve 516 to slowly decrease the cuff pressure $P_c$ after the cuff pressure $P_c$ has been raised up to the target pressure $P_{CM}$. The CPU 528 also operates for identifying a subject's blood pressure abnormality by comparing the estimated BP value with a reference value. If the subject's abnormal blood pressure is identified, the CPU 528 controls an output device 538 to indicate that the blood pressure of the subject is abnormal.

Hereinafter, there will be described the operation of the BP measuring apparatus 600 constructed as described above, by reference to the flow charts of FIGS. 36 and 37. First, at Step SA201, the CPU 528 judges whether a START/STOP switch 542 has been operated for starting the operation of the present apparatus 600, based on a START or a STOP signal supplied from the switch 542. If a negative judgment is made at Step SA201, the control of the CPU 528 waits for receiving the START signal from the switch 542. Meanwhile, if a positive judgment is made, the control proceeds with Step SA202 to operate the air pump 514 and the regulator valve 516 so as to supply a pressurized air to the cuff 510 (i.e., bag 510a) and thereby quickly increase the air pressure in the cuff 510, i.e., cuff pressure $P_c$ at a rate of about 30 to 40 mmHg/sec.

Step SA202 is followed by Step SA203 to judge whether the cuff pressure $P_c$ has reached an initial target pressure $P_{CM}$ prescribed at, e.g., 180 mmHg. If a negative judgment is made at Step SA203, the CPU 528 repeats Steps SA202 and SA203. Meanwhile, if a positive judgment is made, the control of the CPU 528 proceeds with Step SA204 to stop the air pump 514 and change the degree of opening of the regulator valve 516 so as to slowly deflate the cuff 510, i.e., reduce the cuff pressure $P_c$. This slow cuff deflation is carried out at a rate of, e.g., 2 to 3 mmHg/sec suitable for BP measurements. Step SA204 is followed by Step SA205 to judge whether the CPU 528 has received a length of first pulse wave signal SM1 corresponding to one pulse, i.e., one cycle of heartbeat of the subject. If a negative judgment is made at Step SA205, the CPU 528 repeats Steps SA204 and SA205.

Figure 38:
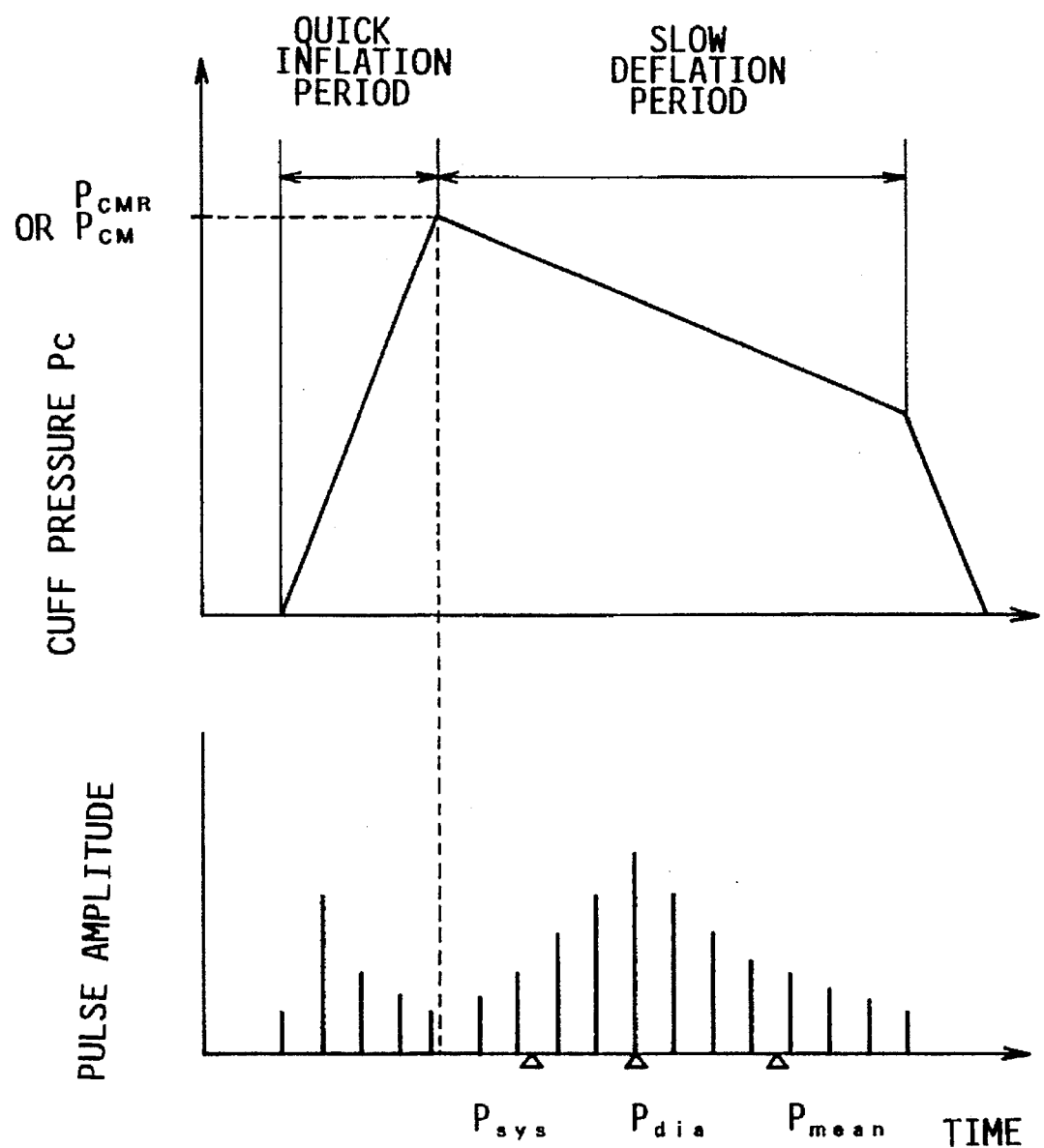
FIG. 38 is a time chart representing the change of cuff pressure $P_c$ in a BP measurement and the change of pulse amplitudes in relation with the change of cuff pressure $P_c$.

Meanwhile, if a positive judgment is made at Step SA205, the control of the CPU 528 proceeds with Step SA206 to store, in a waveform memory area 644 of the RAM 630, the waveform of the one-pulse signal SM1 supplied from the first band-pass filter 522. Step SA206 is followed by Step SA207 where the control device 526 or CPU 528 operates according to a known oscillometric BP measurement algorithm, i.e., determine actual BP values of the subject. Step SA207 is followed by Step SA208 to judge whether the BP measurement subroutine at Step SA207 has been completed. While the cuff pressure $P_c$ is slowly reduced, the respective amplitudes of successive pulses of the pulse wave, i.e., pulse wave signal SM1 initially increase and then decrease as shown in FIG. 38. In the known oscillometric BP measurement algorithm, a cuff pressure $P_c$ at the time when the pulse amplitudes significantly greatly increase is determined as a systolic BP value, $P_{sys}$, of the subject; a cuff pressure $P_c$ at the time of detection of the greatest pulse amplitude is determined as a mean BP value, $P_{mean}$; and a cuff pressure $P_c$ at the time when the pulse amplitudes significantly greatly decrease is determined as a diastolic BP value, $P_{dia}$.

If a negative judgment is made at Step SA208, the CPU 528 repeats Steps SA204 through SA208. Meanwhile, if a positive judgment is made at Step SA208, the control of the CPU 528 proceeds with Step SA209 to store the three BP values $P_{sys}$, $P_{mean}$, $P_{dia}$ in a BP memory area 646 of the RAM 630 and display those BP values in digits on an image-display panel of the output device 538. At the following Step SA210, the CPU 528 fully opens the pressure regulator valve 516 so as to quickly deflate the cuff 510, i.e., quickly decrease the cuff pressure $P_c$ down to atmospheric pressure and thereby release the subject's upper arm from the cuff pressure $P_c$. In the present embodiment, Steps SA204 to SA208 serve as part of the BP measuring device 508 that automatically carries out a BP measurement.

At the following Step SA211, the CPU 528 judges whether a flag, $F_k$, is currently set at one, i.e., $F_k=1$. The state of $F_k=1$ indicates that a relationship used for estimating a BP value of the subject has been determined. Upon initialization of the present BP apparatus 600, the flag $F_k$ is reset to zero, i.e., $F_k=0$. For a while following the starting of operation of the BP apparatus 600, negative judgments are made at Step SA211, and the control of the CPU 528 proceeds with Step SA212 to determine, for the subject around an upper arm of whom the cuff 510 is wound, a relationship between (a) evaluated values of a waveform characteristic, (b) values of cuff pressure $P_c$, and (c) values of blood pressure. Step SA212 is followed by Step SA213 to set the flag $F_k$ to $F_k=1$. Once the flag $F_k$ has been set to $F_k=1$ in a certain control cycle, a positive judgment is made at Step SA211 in the next and following control cycles, so that the control of the CPU 528 proceeds with Step SA214 by bypassing Steps SA212 and SA213.

Figure 39:
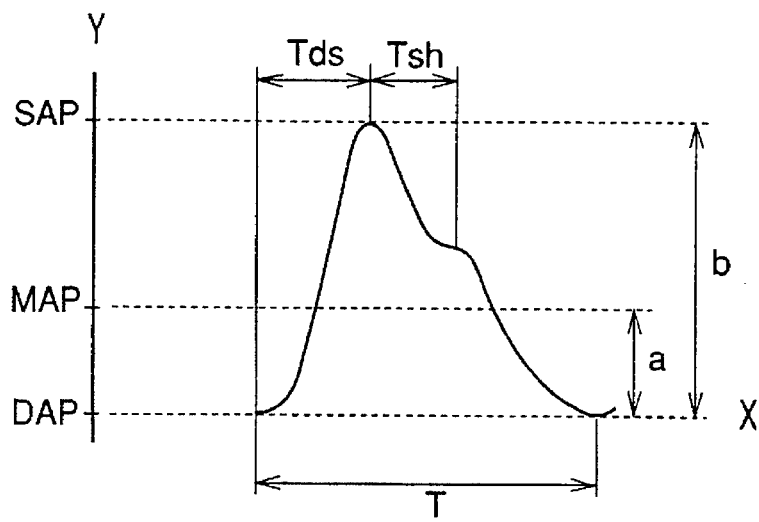
FIG. 39 is a view explaining the respective definitions of various waveform characteristics determined by the apparatus of FIG. 34 to evaluate a pulse waveform.

At Step SA212, the control device 526 or CPU 528 evaluates the waveform of each of the respective pulses stored in the waveform memory area 644 at Step SA206, with respect to each of various waveform characteristics such as pulse amplitude, Amp-b; evaluated value, SLOPE; evaluated value, %MAP; increasing-portion percentage, %IPP; and peak index, PI. As shown in FIG. 39, the pulse amplitude Amp-b of a pulse waveform is defined as the difference between the upper and lower peaks of the pulse waveform (i.e., difference obtained by subtracting the lower peak magnitude, DAP, from the upper peak magnitude, SAP). That is, the pulse amplitude Amp-b evaluates the height of the pulse waveform. The evaluated value SLOPE is defined as the maximum differential, $(dP/dt)_{max}$, of an increasing portion of a pulse waveform, i.e., the greatest slope of the increasing portion of the waveform. The value %MAP is defined as the percentage ($=100\times a/b$) of the y coordinate (i.e., height, $\underline{a}$) of the barycentric coordinates of the area bounded by a pulse waveform and a base line extending parallel to the X axis (i.e., "time" axis) and passing through the lower peak, DAP, of the pulse waveform, with respect to the pulse amplitude $\underline{b}$ (Amp-b). The value %MAP evaluates the degree of sharpness of the waveform. The increasing-portion percentage %IPP is defined as the percentage ($=100\times T_{ds}/T$) of a time duration, $T_{ds}$, of the increasing portion of a pulse waveform with respect to a cyclic period, T (sec), of the pulse waveform. The value %IPP evaluates the degree of imbalance of the waveform. The peak index PI is defined as the percentage ($=100\times T_{sh}/T$) of a time duration, $T_{sh}$, between the upper peak, SAP, and the secondary peak of a pulse waveform, with respect to the cyclic period T (sec) of the pulse waveform. The evaluated value PI indicates the position of the secondary peak on the pulse waveform.

Figure 40:
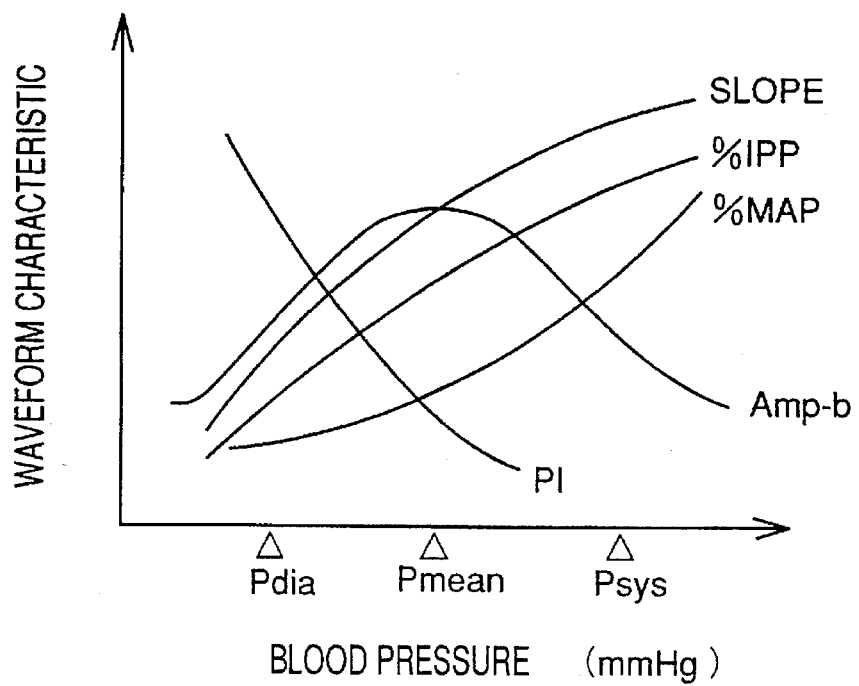
FIG. 40 is a view explaining a relationship between blood pressure (i.e., cuff pressure values $P_c$ as the measured blood pressure values) and each of the waveform characteristics.
Figure 41:
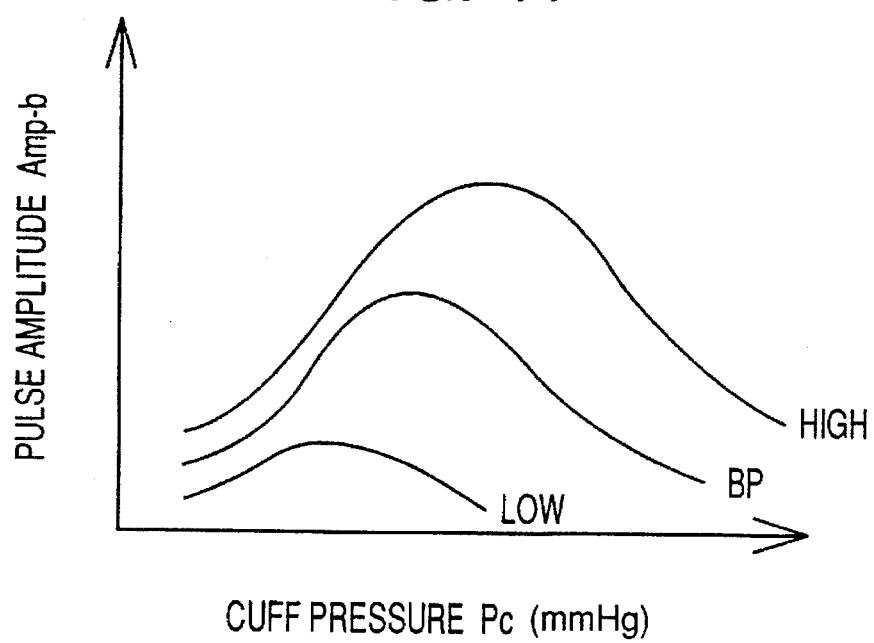
FIG. 41 is a view explaining a relationship between cuff pressure $P_c$ and pulse amplitude Amp-b.
Figure 42:
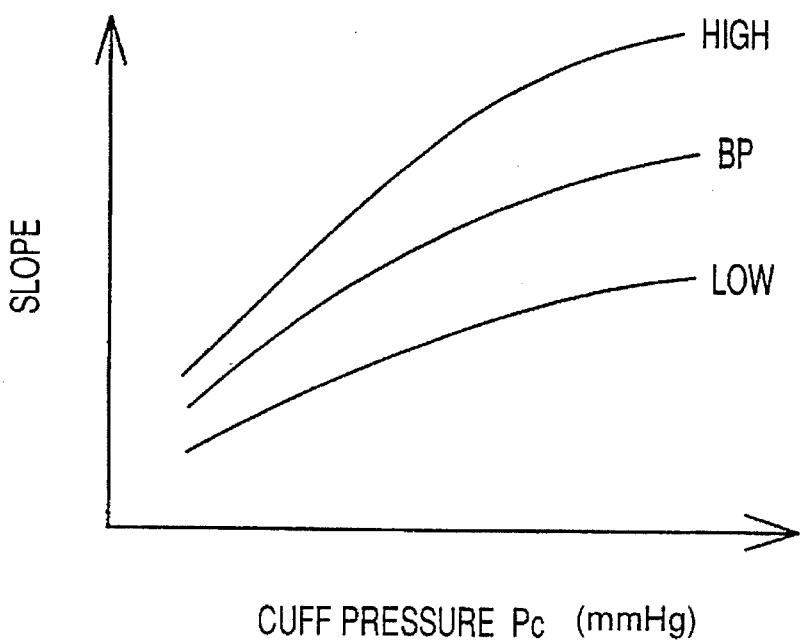
FIG. 42 is a view explaining a relationship between cuff pressure $P_c$ and waveform slope SLOPE.
Figure 43:
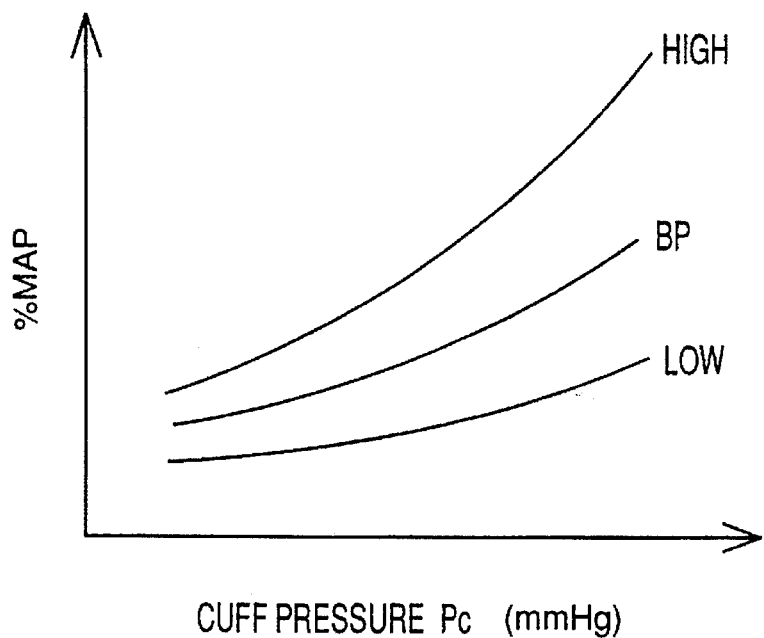
FIG. 43 is a view explaining a relationship between cuff pressure $P_c$ and evaluated value %MAP.
Figure 44:
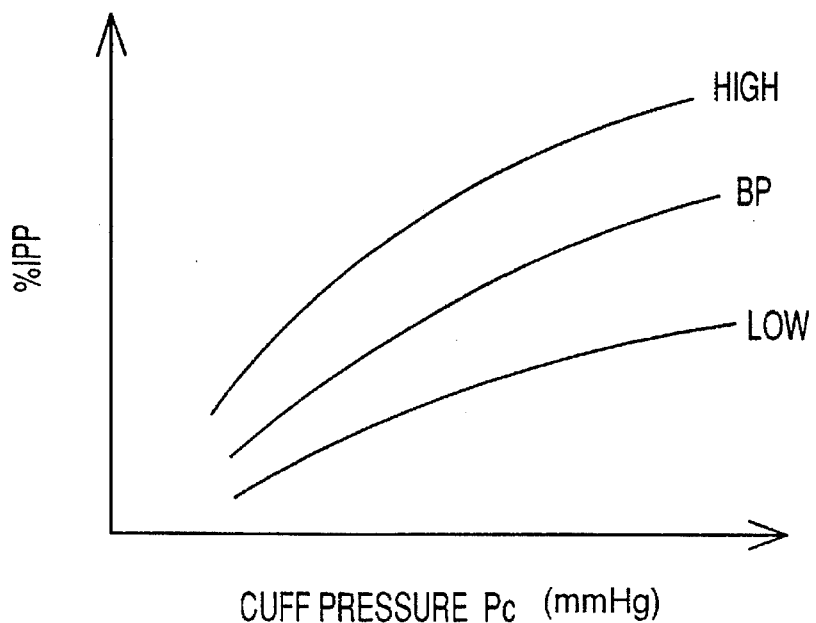
FIG. 44 is a view explaining a relationship between cuff pressure $P_c$ and evaluated value %IPP.
Figure 45:
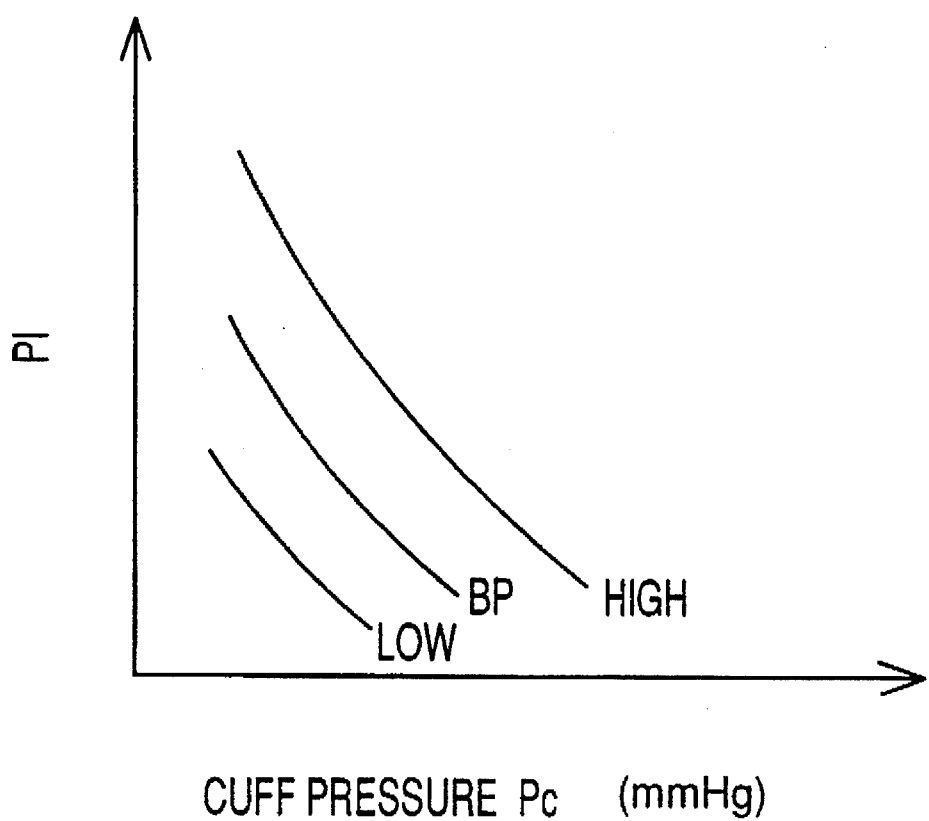
FIG. 45 is a view explaining a relationship between cuff pressure $P_c$ and evaluated value PI.

At Step SA212, the CPU 528 obtains, from the evaluated values of the waveform characteristics Amp-b, SLOPE, %MAP, %IPP, PI, data representing a relationship between the measured BP values of the subject and each waveform characteristic as shown in FIG. 40. Since the BP values $P_{sys}$, $P_{mean}$, $P_{dia}$ of the subject are measured by reading the cuff pressure values $P_c$, the CPU 528 can determine a relationship between blood pressure BP, each waveform characteristic Amp-b, SLOPE, %MAP, %IPP, PI, and cuff pressure Pc as shown in FIGS. 41, 42, 43, 44, and 45 where the blood pressure BP is variable as a parameter. Although only three curves each representing a BP value are shown in each of FIGS. 41–45, a number of curves each representing a BP value are, in fact, employed in each graph or map. Each map contains a number of base curves given according to a prescribed rule, and those base curves are modified based on a measured BP value of the subject which may be one of the measured systolic, mean, and diastolic BP value $P_{sys}$, $P_{mean}$, $P_{dia}$.

Step SA213 is followed by Step S214 to judge whether the BP monitor apparatus 600 is currently placed in the BP-monitor mode, based on a mode signal supplied from a mode switch 540. If a negative judgment is made at Step S214, that is, if the apparatus 600 is currently placed in the single-BP-measurement mode, the current control cycle in accordance with the main routine is ended, and the control of the CPU 528 returns to Step SA201 and the following steps. On the other hand, if a positive judgment is made at Step SA214, that is, if the apparatus 500 is currently placed in the BP-monitor mode, the control of the CPU 528 goes to Step SA215 to clear the contents of a time counter (timer), T3, to zero and subsequently to Step SA216 to judge whether the START/STOP switch 542 has been operated again, based on the START/STOP signal supplied from the switch 542. If a positive judgment is made at Step SA216, the current control cycle is ended, and the control of the CPU 528 goes back to Step SA201.

On the other hand, if a negative judgment is made at Step SA216, the control goes to Step SA217 to increment the contents of the timer T3 by one, i.e., T3←T3+1. At the following Step SA217, the CPU 528 judges whether the contents of the timer T3 has reached a prescribed reference time $T_{4M}$. This reference time $T_{4M}$ is the period of cyclic measurements of the BP measuring apparatus 600, and is pre-selected to fall within a range of several minutes to several tens of minutes. For a while following the beginning of the BP monitor operation, negative judgments are made at Step SA218, so that the CPU 528 repeats Steps SA216, SA217 and SA218. Meanwhile, if a positive judgment is made at Step SA218, the control of the CPU 528 proceeds with Step SA219 and the following steps to estimate a BP value of the subject based on the waveform of a pulse obtained in a quick inflation of the cuff 510.

More specifically described, at Step SA219, the CPU 528 operates, like at Step SA202, the air pump 514 and the pressure regulator valve 516 to quickly increase the cuff pressure $P_c$. Step SA219 is followed by Step SA220 to judge whether a length of the pulse wave signal SM1 corresponding to a cycle of heartbeat of the subject, i.e., the waveform of one pulse is supplied to the control device 526 or CPU 528. If a negative judgment is made at Step SA220, the CPU 528 repeats Steps SA219 and SA220 to quickly increase the cuff pressure $P_c$. Meanwhile, if a positive judgment is made, the control of the CPU 528 goes to Step SA221 to store the waveform of the one-pulse signal SM1 in the waveform memory area 644 of the RAM 630.

At the following Step SA222, i.e., BP estimation subroutine, the CPU 528 estimates a BP value of the subject, based on the pulse waveform stored in the memory 644 at Step SA221, according to the various relationships determined at Step SA212 that are proper to the subject around an upper arm of whom the cuff 510 is currently wound. Specifically, at Step SA222, the CPU 528 calculates one or more of characteristic evaluated values Amp-b, SLOPE, %MAP, %IPP, PI of the stored waveform, and subsequently calculates one or more BP values, based on the calculated one or more evaluated values Amp-b, SLOPE, %MAP, %IPP, PI and a cuff pressure value $P_c$ at the time of supplying of the pulse waveform, according to the corresponding one or more of the relationships or maps shown in FIGS. 41–45. The CPU 528 estimates a BP value of the subject, based on the thus calculated one or more BP values, according to a prescribed arithmetic expression.

As described above, the blood pressure BP employed as a parameter in each of the relationships or maps of FIGS. 41–45 may be the systolic, mean, or diastolic BP value $P_{sys}$, $P_{mean}$, $P_{dia}$ of the subject. For example, in the case where the maps of FIGS. 41–45 are determined for the systolic BP value $P_{sys}$ of the subject, the CPU 528 estimates, at Step SA222, a systolic BP value of the subject according to those maps. This applies to the mean and diastolic BP values of the subject. Therefore, in the case where the maps of FIGS. 41–45 are determined for each of the systolic, mean and diastolic BP values $P_{sys}$, $P_{mean}$, $P_{dia}$ of the subject, the CPU 528 estimates, at Step SA222, a systolic, a mean and a diastolic BP value of the subject according to those maps.

The CPU 528 determines, as an estimated BP value of the subject, an average of the calculated two or more BP values. Otherwise, the CPU 528 may be modified to determine, as an estimated BP value, an average of respective weighted values of the calculated two or more BP values, or an average of one or more BP values obtained by removing the greatest and smallest values from the three or more calculated BP values. However, if the CPU 528 judges that the stored waveform is abnormal, the CPU 528 does not estimate a BP value of the subject. In this case, therefore, a negative judgment is made at the following Step SA223. The CPU 528 judges whether the stored waveform is abnormal, by identifying whether each of one or more characteristic evaluated values Amp-b, SLOPE, %MAP, %IPP, PI of the waveform falls within a corresponding normal range. In the case where the first pulse, i.e., first waveform obtained during the quick inflation of the cuff 510 is normal, the CPU 528 estimates, at Step SA222, a BP value of the subject based on the first waveform. Accordingly, a positive judgment is made at Step SA223.

Steps SA222 is followed by Step SA223 to judge whether a BP estimation at Step SA222 has been completed. If a negative judgment is made at Step SA223, the control of the CPU 528 goes back to Step SA219 and the following steps to quickly increase the cuff pressure $P_c$. On the other hand, if a positive judgment is made, the control goes to Step SA224 to judge whether the estimated BP value of the subject is abnormal. For example, in the case of an estimated systolic BP value, the CPU 528 judges whether the estimated systolic BP value falls within a range of 100 to 200 mmHg; and in the case of an estimated diastolic BP value, the CPU 528 judges whether the estimated diastolic BP value falls within a range of 50 to 150 mmHg. If a negative judgment is made, the CPU 528 judges that the estimated BP value is abnormal.

If a positive judgment is made at Step SA224, i.e., if the estimated BP value is found to be abnormal, the control of the CPU 528 goes to Step SA225 to control the output device 538 to indicate that the estimated BP value is abnormally high or low. On the other hand, if a negative judgment is made at Step SA224, the control goes to Step SA226 to determine a modified target pressure, $P_{CMR}$, such that the pressure $P_{CMR}$ is equal to an estimated BP value of the subject. This estimated systolic BP value may be equal to the estimated systolic BP value obtained at Step SA222, or a systolic BP value estimated based on the mean or diastolic BP value obtained at Step SA222. Step SA226 is followed by Step SA227 to judge whether the cuff pressure $P_c$ has reached a pressure value, $P_{CMR}+\alpha$, obtained by adding a prescribed buffer or excess value to the pressure $P_{CMR}$. If a negative judgment is made at Step SA227, the control of the CPU 528 goes back to Step SA219 and the following steps to quickly increase the cuff pressure $P_c$. On the other hand, if a positive judgment is made, the control goes to Step SA204 and the following steps to slowly decrease the cuff pressure $P_c$ and carry out a BP measurement according to the oscillometric method.

As is apparent from the foregoing description, in the fifth embodiment, Step SA212 and a portion of the control device 526 for carrying out this step cooperate with each other to serve as means for determining the relationships shown in FIGS. 41–45, and Step SA222 and a portion of the control device 526 for carrying out this step cooperate with each other to serve as means for estimating a systolic, a mean or a diastolic BP value of the subject, based on (a) each characteristic evaluated value of a pulse waveform supplied from the first band-pass filter 522 during the quick inflation of the cuff 510, and (b) a cuff pressure value $P_c$ at the time of supplying of the pulse waveform, according to a corresponding one of the relationships or maps of FIGS. 41–45. The second pulse wave signal SM2 supplied from the second band-pass filter 523 may be used in place of the first pulse wave signal SM1, for supplying a pulse waveform to the control device 526 or CPU 528.

The present BP measuring apparatus 600 estimates a BP value of the subject, based on (a) a characteristic evaluated value of a pulse waveform supplied during a quick cuff inflation period before a slow cuff deflation period, and (b) a cuff pressure value $P_c$ at the time of supplying of the pulse waveform. Thus, the apparatus 600 provides a considerably accurate estimated BP value of the subject shortly after the beginning of each of cyclic BP measurements carried out in the BP-monitor mode.

In the case where, at Step SA222, two or more BP values of the subject are calculated according to the two or more relationships determined at Step SA212, the CPU 528 estimates a BP value of the subject based on the two or more calculated BP values. Therefore, the thus estimated BP value of the subject enjoys a high accuracy.

Step SA226 and a portion of the control device 526 for carrying out this step cooperate with each other to serve as means for determining a modified target pressure $P_{CMR}$ based on an estimated BP value of the subject provided at Step SA222; and the pressure regulator valve 516 and a portion of the control device 526 for controlling the valve 516 cooperate with each other to serve as means for regulating the cuff pressure $P_c$ by quickly increasing the pressure $P_c$ up to a pressure higher by an access $\alpha$ than the determined target pressure $P_{CMR}$ and thereafter slowly decreasing the pressure $P_c$. Since the pressure higher by the access $\alpha$ than the determined target pressure $P_{CMR}$ is a necessary and adequate pressure higher than the estimated systolic BP value of the subject, the BP apparatus 600 effectively prevents the cuff pressure $P_c$ from being increased up to an unnecessarily high value, thereby preventing the subject from feeling discomfort due to the unnecessarily high pressure.

Step SA224 and a portion of the control device 526 for carrying out this step cooperate with each other to serve as judging means for judging whether the blood pressure of the subject is abnormal, by comparing the estimated BP value of the subject obtained at Step SA222, with a reference pressure range. The output device 538 and a portion of the control device 526 for controlling the output device 538 cooperate with each other to serve as means for outputting an indication that the blood pressure of the subject is abnormal, when the judging means makes a positive judgment. Therefore, the present apparatus 600 ensures that medical workers can recognize a subject's blood pressure abnormality at an early point of time in a quick cuff inflation period. Accordingly, the medical workers such as doctors can take appropriate medical actions on the subject.

It is to be understood that the BP measuring apparatus 600 as the fifth embodiment may be modified in various ways.

Figure 46:
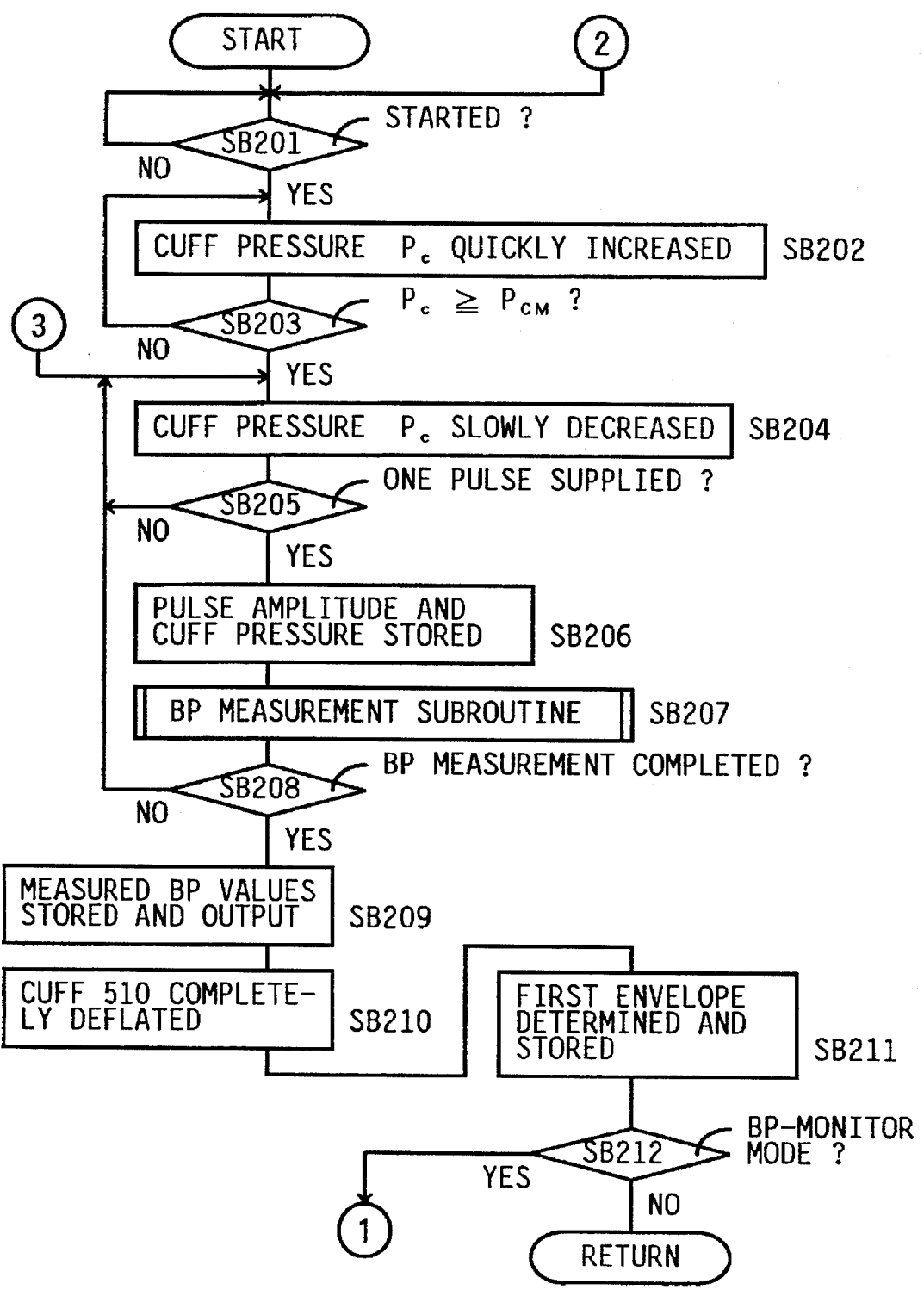
FIG. 46 is a flow chart representing a first half of a modified control program according to which the apparatus of FIG. 34 operates.
Figure 47:
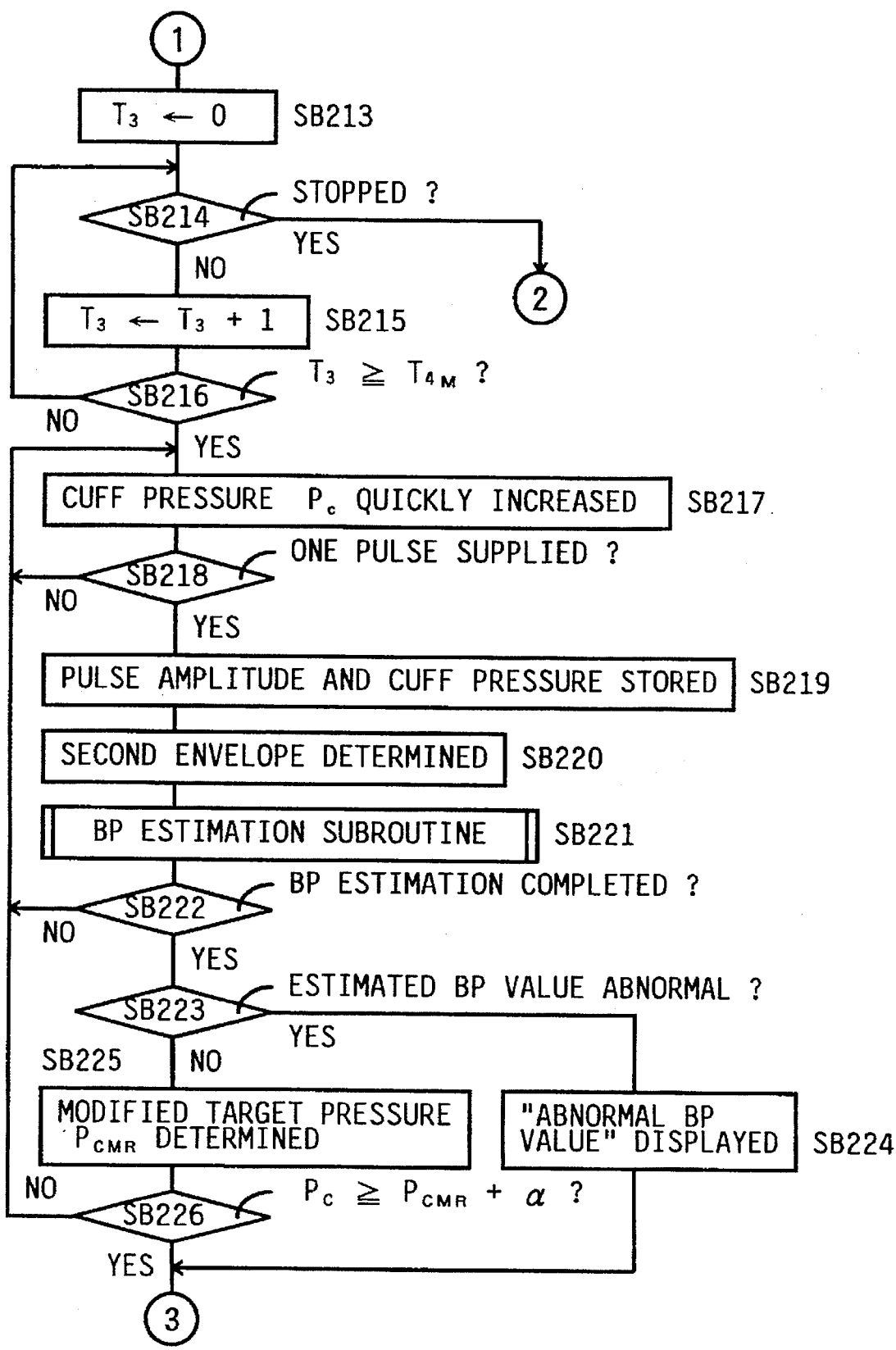
FIG. 47 is a time chart representing a second half of the modified control program of FIG. 46.

For example, the BP apparatus 600 may be modified to operate according to the control program represented by the flow charts of FIGS. 46 and 47. In this modified manner of operation, the pressure sensor 512 serves as a pressure detector which detects a cuff pressure $P_c$, i.e., pressing pressure of the cuff 510 wound around a body portion of a living subject; the first or second band-pass filter 522, 523 serves as a pulse wave detector which detects, as a pulse wave, a pressure oscillation mixed with the cuff pressure $P_c$ detected by the pressure sensor 512; the BP measuring device 508 determines a BP value of the subject based on the change of successive pulse amplitudes produced during the slow decreasing of the cuff pressure $P_c$; the pressure regulator valve 516 and a portion of the control device 526 for controlling the valve 516 cooperate with each other to start a BP measurement by quickly increasing the cuff pressure $P_c$ up to a prescribed target pressure value $P_{CM}$ and subsequently slowly decreasing the cuff pressure $P_c$ and terminates the BP measurement by completely deflating the cuff 510 after the BP value of the subject has been determined during the slow decreasing of the cuff pressure $P_c$ by the BP measuring device 508; a pulse amplitude/cuff pressure (PA/CP) memory area 680 of the RAM 630 stores each of the successive pulse amplitudes detected by the band-pass filter 522, 523 and a cuff pressure value $P_c$ at the time of detection of each pulse amplitude, in the order of detection of the pulse amplitudes. The control device 526 or CPU 528 determines an envelope representing a relationship between (a) the pulse amplitudes detected during the quick cuff inflation period by the band-pass filter 522, 523 and (b) the cuff pressure values $P_c$ at the times of detection of those pulse amplitudes. In addition, the CPU 528 operates for estimating a BP value of the subject, based on the determined envelope, according to a prescribed rule or relationship.

The control device 526 determines, in advance, a first envelope based on (a) a considerable great number of pulse amplitudes obtained by the BP measuring device 508 in measuring a BP value of the subject and (b) the cuff pressure values $P_c$ when those pulse amplitudes are obtained. Since the first envelope is determined based on the many pulse amplitudes, the first envelope has a considerably high accuracy. Additionally, this envelope has a curved pattern proper to the subject. In a manner similar to that employed for determining the above envelope, the control device 526 determines a second envelope or curve connecting a considerable small number of pulse amplitudes obtained during a quick cuff inflation, over the respective cuff pressure values $P_c$ when those pulse amplitudes are obtained. Based on the second envelope, the CPU 528 estimates a BP value of the subject. For example, like in the oscillometric BP measurement technique, a cuff pressure value $P_c$ corresponding to a maximum value of the second envelope is estimated as a mean BP value of the subject; and two cuff pressure values $P_c$ corresponding to two maximum slopes of the second envelope are estimated as a systolic and a diastolic BP value of the subject (the higher cuff pressure $P_c$ is estimated as the systolic BP value and the lower cuff pressure $P_c$ is estimated as the diastolic BP value).

In this modified manner, the control device 526 or CPU 528 operates for determining, based on an estimated BP value of the subject, a modified target pressure $P_{CMR}$ to which the cuff pressure $P_c$ is quickly increased in a BP measurement. The CPU 528 controls the air pump 514 and the pressure regulator valve 516 to slowly decrease the cuff pressure $P_c$ after the pressure $P_c$ has been raised up to the modified target pressure $P_{CMR}$. The CPU 528 also operates for identifying a subject's blood pressure abnormality by comparing the estimated BP value with a reference pressure value or range. If the subject's abnormal blood pressure is identified, the CPU 528 controls the output device 538 to indicate that the blood pressure of the subject is abnormal.

Hereinafter, there will be described the operation of the BP apparatus 600 as modified as described above, by reference to the flow charts of FIGS. 46 and 47 employed in place of the flow charts of FIGS. 36 and 37.

Steps SB201 through SB205 are the same as Steps SA201 through SA205 of FIG. 36, and are carried out to quickly increase the cuff pressure $P_c$, subsequently slowly decrease the cuff pressure $P_c$, and judge whether one pulse has been supplied from the first band-pass filter 522.

At the following Step SB206, the CPU 528 stores, in the PA/CP memory area 680 of the RAM 630, the amplitude of one pulse supplied from the first band-pass filter 522 and the cuff pressure value Pc at the time of supplying of the one-pulse signal SM1. Step SB207 is the same as Step SA207 of FIG. 36, and is carried out to measure an actual BP value of the subject. Steps SB208 through SB210 are the same as Steps SA208 through SA210 of FIG. 36, and are executed to judge whether the BP measurement has been completed, output the measured BP value or values, and reduce the cuff pressure $P_c$ down to atmospheric pressure, thereby releasing the subject's upper arm from the pressing of the cuff 510.

Figure 48:
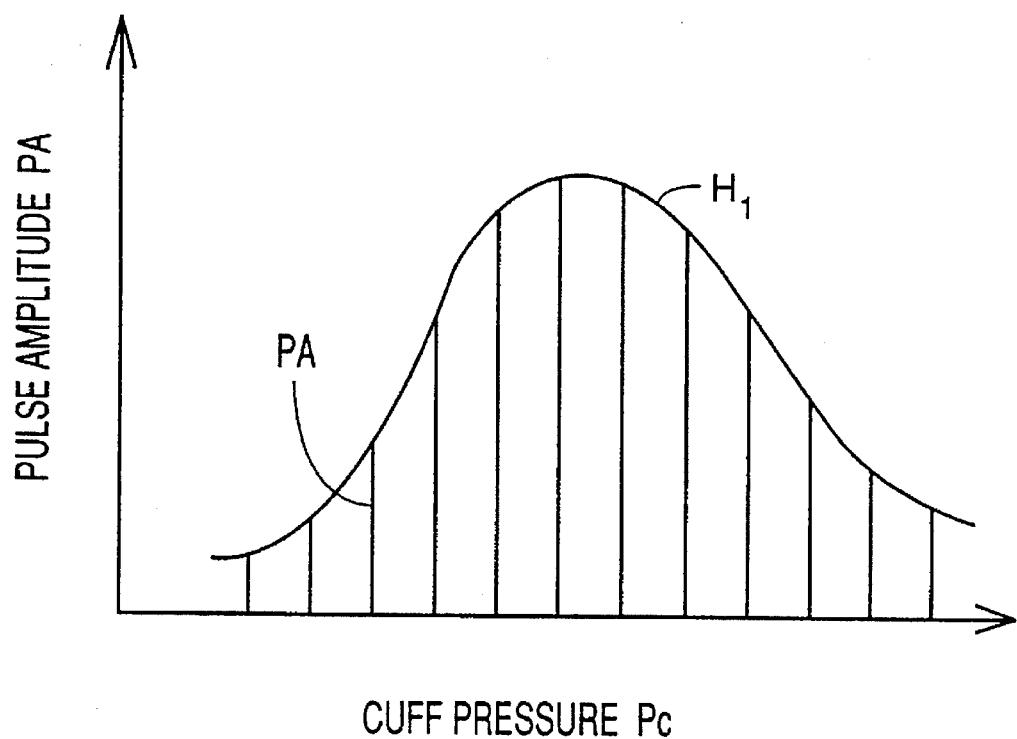
FIG. 48 is a view explaining a first envelope $H_1$ representing a relationship between cuff pressure values $P_c$ and pulse amplitudes PA, the pulse amplitudes being obtained while the cuff pressure $P_c$ is slowly decreased according to the flow chart of FIG. 46.

At the end of a BP measurement carried out at Steps SB201 through SB210, a considerably great number of pulse amplitudes and corresponding cuff pressure values $P_c$ which are obtained in the BP measurement, are stored in the PA/CP memory area 680. Therefore, at the following Step SB211, the control device 526 or CPU 528 determines a first envelope, $H_1$, connecting data points representing the pulse amplitudes, PA, and the corresponding cuff pressure values $P_c$, as shown in FIG. 48. Since the first envelope $H_1$ is obtained based on the considerably great number of data points obtained in the BP measurement, the first envelope $H_1$ enjoys a considerably high accuracy, and represents a curved pattern proper to the subject.

Figure 36:
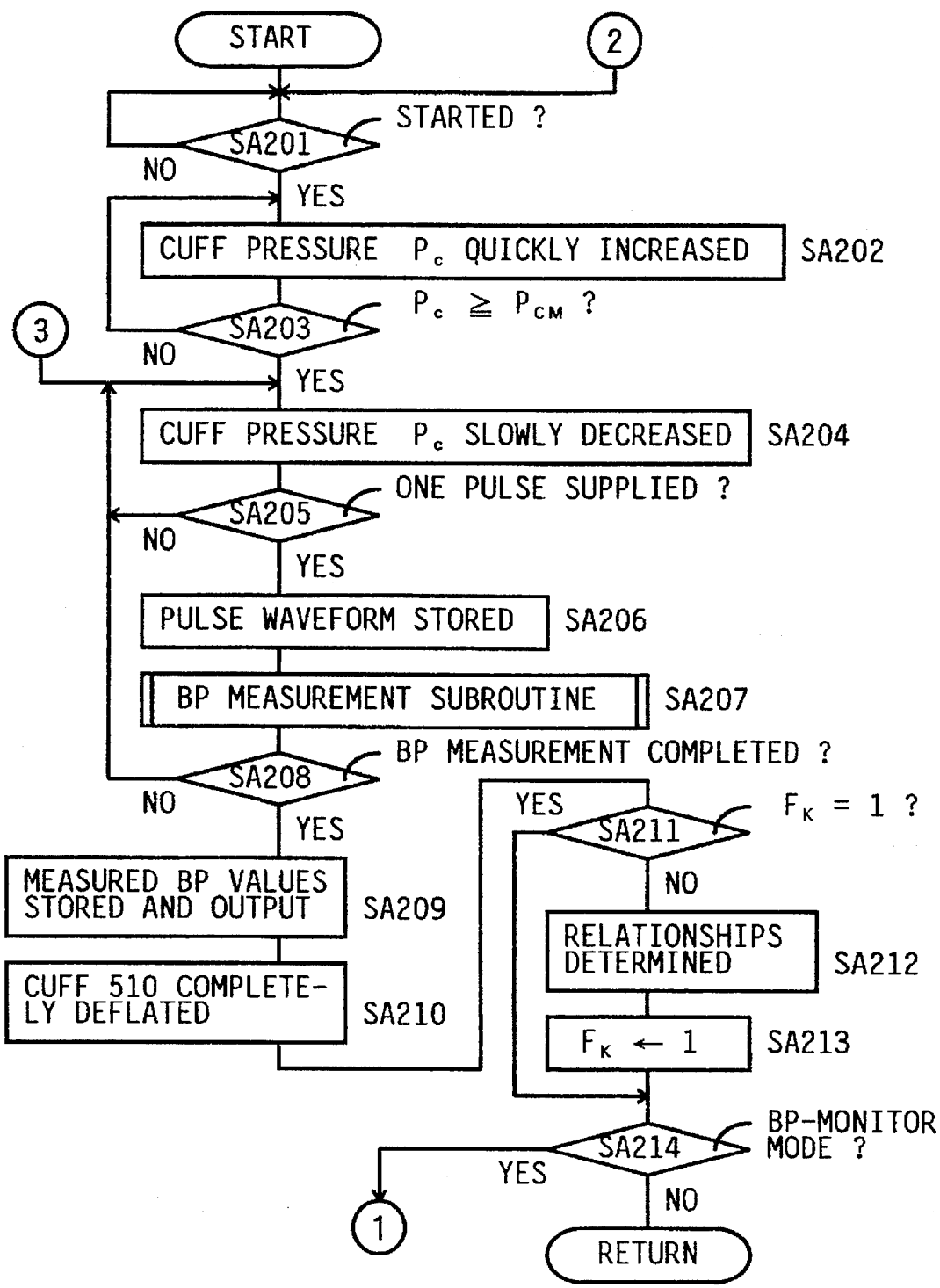
FIG. 36 is a flow chart representing a first half of a control program according to which the apparatus of FIG. 34 operates.

Step SB212 is the same as Step SA214 of FIG. 36. If a positive judgment is made at Step SB212, the CPU 528 carries out Steps SB213 through SB217 that are the same as Steps SA215 through SA219 of FIG. 37, thereby quickly increasing the cuff pressure $P_c$. At the following Step SB220, the CPU 528 judges whether one pulse has been supplied from the first band-pass filter 522 during the quick increasing of the cuff pressure $P_c$, i.e., during the quick cuff inflation period. However, the CPU 528 adopts, as a correct or true pulse, only a pulse which falls within a reference range, T (pulse period) ±20%. The pulse period T is defined as the time distance between the respective upper (or lower) peaks of the last pair of successive two pulses each pulse of which has been adopted as a true pulse. If the current pulse does not fall within the reference range, i.e., time window, the CPU 528 discards the pulse as noise. If a positive judgment is made at Step SB211, the control of the CPU 528 goes to Step SB219 to store, in the PA/CP memory area 680, the amplitude of the pulse and the cuff pressure value $P_c$ at the time of supplying of the pulse amplitude. Step SB219 is followed by Step SB220 to determine, according to an envelope determination algorithm, a second envelope, $H_2$, representing a relationship between (a) the pulse amplitudes obtained during the quick cuff inflation period and (b) the cuff pressure values $P_c$ when those pulse amplitudes are obtained. Since the number of the data points used to determine the second envelope $H_2$ is considerably small, the CPU 528 modifies the original polygonal line $H_2$ obtained by connecting the data points with one another, in such a manner that the modified curved line, i.e., second envelope $H_2$ is similar to the pattern of the first envelope $H_1$. FIGS. 49(A), 49(B), 49(C), and 49(D) shows examples of the second envelope $H_2$ which can be obtained at Step SB220.

At the following Step SB221, the CPU 528 estimates a BP value of the subject based on the second envelope $H_2$ which is determined at Step SB220 based on the pulses obtained during the quick cuff inflation period. Specifically described, like the oscillometric BP determination technique, a cuff pressure value corresponding to the maximum value of the second envelope $H_2$ is determined as an estimated mean BP value of the subject, and two cuff pressure values corresponding to two maximum slopes of the second envelope $H_2$ are determined as an estimated systolic and an estimated diastolic BP value of the subject (the higher cuff pressure is determined as the estimated systolic BP value and the lower cuff pressure is determined as the estimated diastolic BP value).

Step SB221 is followed by Step SB222 to judge whether the BP estimation at Step SB221 has been completed. If a negative judgment is made at Step SB222, the control of the CPU 528 goes back to Step SB217 and the following steps to read in subsequent pulses. On the other hand, if a positive judgment is made, the control goes to Steps SB223 through SB226 that are the same as Steps SA224 through SA227. If at Step SB523 the CPU 528 judges that the estimated BP value of the subject determined at Step SB221 is abnormal, the CPU 528 controls, at Step SB224, the output device 538 to indicate that the estimated BP value of the subject is abnormal. On the other hand, if at Step SB523 the CPU 528 does not judge that the estimated BP value of the subject determined at Step SB221 is abnormal, the CPU 528 determines, at Step SB225, a modified target pressure $P_{CMR}$. If the actual cuff pressure $P_c$ reaches a pressure higher by an excess or buffer value $\alpha$ than the modified target pressure $P_{CMR}$, the control of the CPU 528 goes back to Step SB204 and the following steps.

In the modified BP monitor operation in accordance with the flow charts of FIGS. 46 and 47, the first band-pass filter 522 serves as a pulse detector which detects pulse amplitudes while the cuff pressure $P_c$ is quickly increased. Step SB220 and a portion of the control device 526 for carrying out this step cooperate with each other to serve as means for determining a second envelope $H_2$ representing a relationship between (a) the respective amplitudes of the pulses detected by the pulse detector during the quick cuff inflation period and (b) the respective cuff pressure values at the times of detection of those pulse amplitudes. Step SB221 and a portion of the control device 526 for carrying out this step cooperate with each other to serve as means for estimating a BP value of the subject, based on the second envelope $H_2$ determined at Step SB220, according to a prescribed BP estimation rule such as a known oscillometric BP determination rule. Thus, the apparatus 600 modified as described above provides a considerably accurate estimated BP value of the subject based on the second envelope $H_2$ obtained in each quick cuff inflation period before each slow cuff deflation period, i.e., shortly after the beginning of each cyclic BP measurement carried out in the BP-monitor mode. Thus, medical workers can quickly know the considerably accurate BP value or values of the subject.

In addition, since at Step SB218 the CPU 528 adopts only pulses each of which falls inside an appropriate time window, i.e., discards "noise" pulses which do not fall inside the time window, the estimated BP values of the subject enjoy a high reliability.

Step SB225 and a portion of the control device 526 for carrying out this step cooperate with each other to serve as means for determining a modified target pressure $P_{CMR}$ based on an estimated BP value of the subject provided at Step SB221; and the pressure regulator valve 516 and a portion of the control device 526 for controlling the valve 516 cooperate with each other to serve as means for regulating the cuff pressure $P_c$ by quickly increasing the pressure $P_c$ up to a pressure higher by the access $\alpha$ than the determined target pressure $P_{CMR}$ and then slowly decreasing the pressure $P_c$. Since the pressure higher by the access $\alpha$ than the modified target pressure $P_{CMR}$ is a necessary and adequate pressure higher than an estimated systolic BP value of the subject, the BP apparatus 600 effectively prevents the cuff pressure $P_c$ from being increased up to an unnecessarily high value, thereby preventing the subject from feeling discomfort due to the unnecessarily high pressure.

Step SB223 and a portion of the control device 526 for carrying out this step cooperate with each other to serve as judging means for judging whether the blood pressure of the subject is abnormal, by comparing the estimated BP value of the subject obtained at Step SB221, with a reference pressure value or range. The output device 538 and a portion of the control device 526 for controlling the output device 538 cooperate with each other to serve as means for outputting an indication that the blood pressure of the subject is abnormal, when the judging means makes a positive judgment. Therefore, the present apparatus 600 as modified also ensures that medical workers can recognize a subject's blood pressure abnormality at an early point of time in a quick cuff inflation period. Accordingly, the medical workers such as doctors can take appropriate medical actions on the subject.

Figure 37:
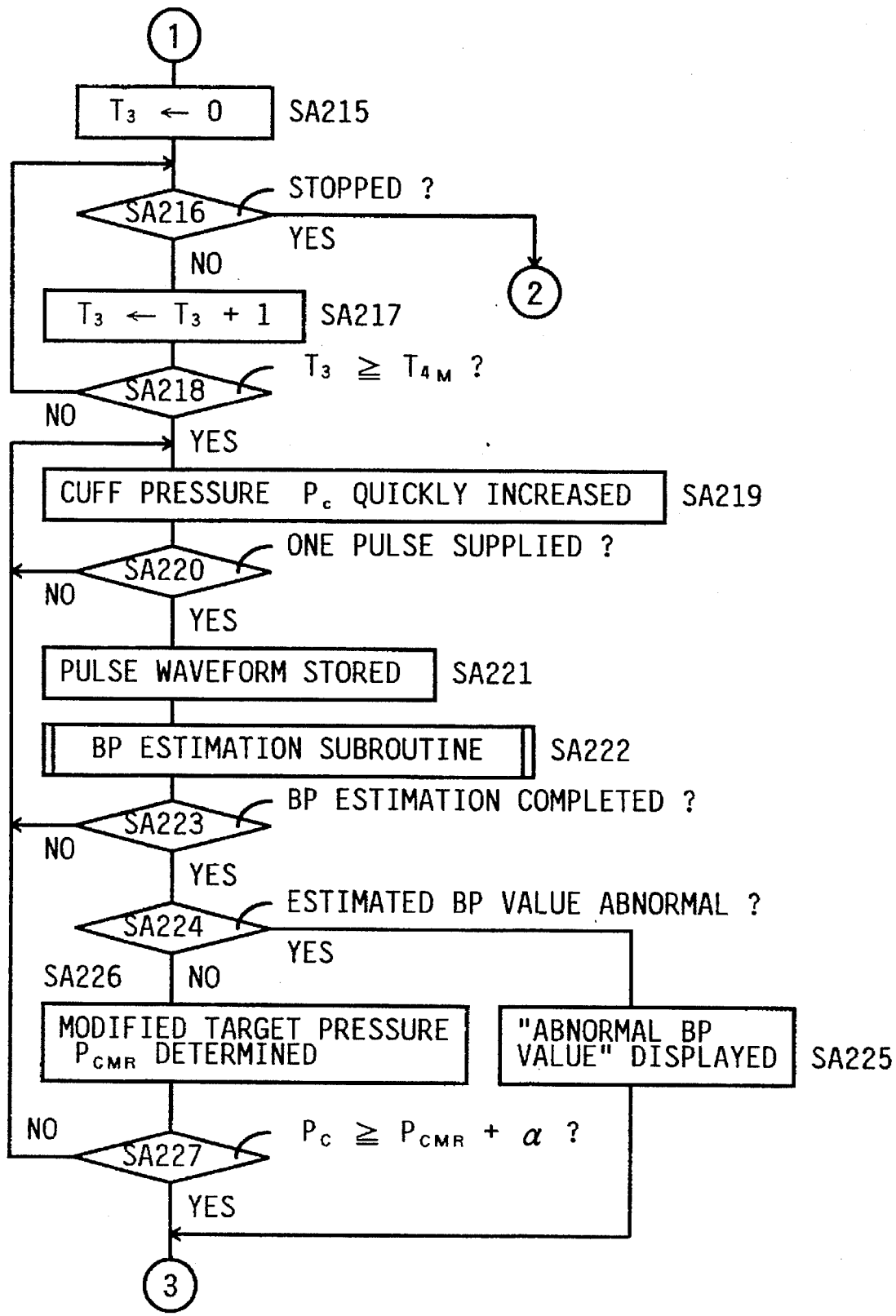
FIG. 37 is a flow chart representing a second half of the control program of FIG. 36.

While in the BP monitor operation in accordance with the flow charts of FIGS. 36 and 37 the relationships determined at Step SA212 once in the first BP monitor cycle following each BP measurement are used to estimate a BP value of the subject also in each of the subsequent BP monitor cycles, without being updated, it is possible to modify the BP apparatus 600 to carry out BP measurements at regular intervals of time and periodically determine new relationships based on the BP value or values determined in each BP measurement.

Although the cuff pressure $P_c$ is monotonously increased during each quick cuff inflation period and pulse amplitudes are obtained in the process in which the cuff pressure $P_c$ is increased in that manner, it is possible to stepwise increase the cuff pressure $P_c$ while holding the pressure $P_c$ at pressure steps each for a prescribed short duration, so that the control device 526 obtains one or more pulses when the pressure $P_c$ is held at each step. In the latter case, the control device 526 can utilize pulses having more accurate waveforms.

Figure 49A:
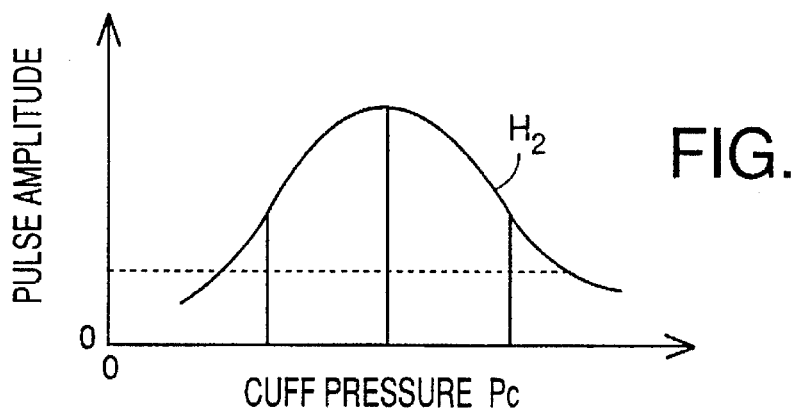
FIG. 49(A) is a view explaining a first example of a second envelope $H_2$ representing a relationship between cuff pressure values $P_c$ and pulse amplitudes PA, the pulse amplitudes being obtained while the cuff pressure $P_c$ is quickly increased according to the flow chart of FIG. 47.
Figure 49B:
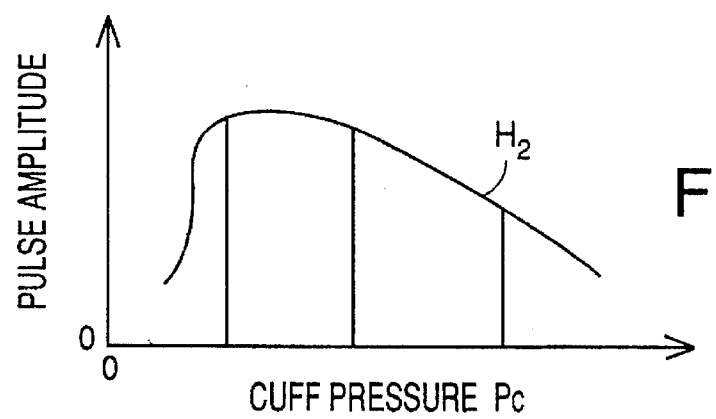
FIG. 49(B) is a view explaining a second example of the second envelope $H_2$.
Figure 49C:
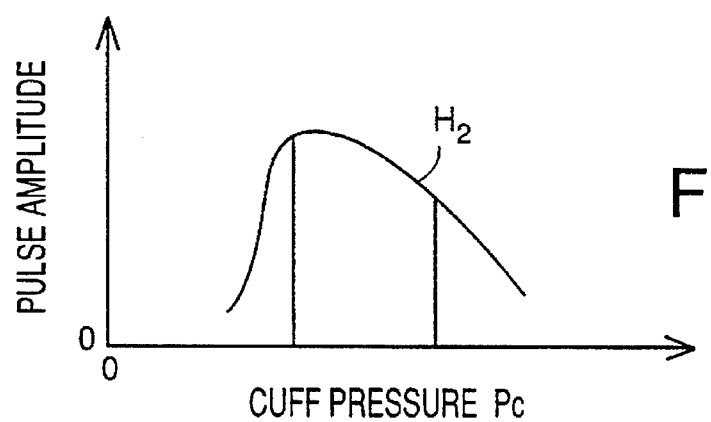
FIG. 49(C) is a view explaining a third example of the second envelope $H_2$.
Figure 49D:
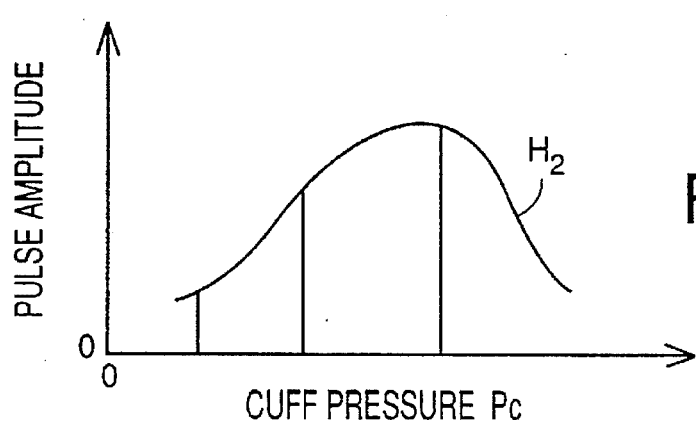

While at Step SB221 of the flow chart of FIG. 47 the oscillometric BP determination technique is utilized to estimate a BP value of the subject based on the second envelope $H_2$, it is possible to employ other BP estimation methods or techniques. For example, it is possible to employ an easier technique to determine, as an estimated systolic, mean, or diastolic blood pressure of the subject, a cuff pressure value $P_c$ corresponding to a point of intersection of the second envelope $H_2$ and a broken line corresponding to a prescribed pulse amplitude, as shown in FIG. 49(A).

Figure 50:
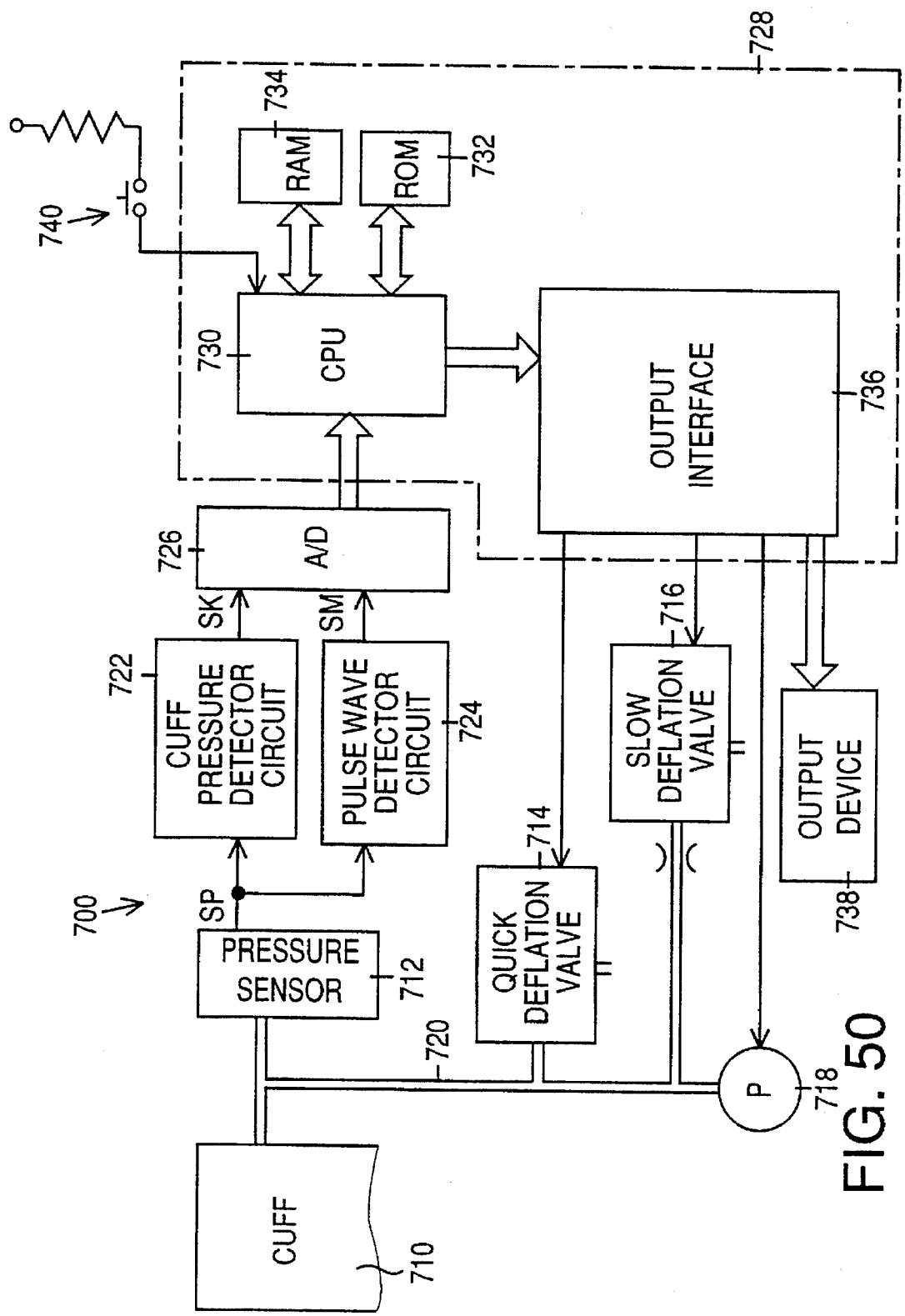
FIG. 50 is a diagrammatic view of an automatic BP measuring apparatus as a sixth embodiment of the present invention.

Referring next to FIG. 50, there is shown an automatic blood pressure (BP) measuring apparatus 700 as a sixth embodiment of the present invention.

In FIG. 50, reference numeral 710 designates an inflatable cuff adapted to be wound around an upper arm of a living subject (e.g., patient) so as to press the upper arm. The cuff 710 includes an inflatable bag (not shown). The inflatable bag of the cuff 510 is connected via piping 720 to a pressure sensor 712, a quick deflation valve 714, a slow deflation valve 716, and an air pump 718.

The pressure sensor 712 detects an air pressure in the cuff 710 ("cuff pressure") and supplies a detection signal, SP, to a cuff-pressure detector circuit 722 and a pulse-wave detector circuit 724. The cuff-pressure detector circuit 722 includes a low-pass filter (not shown) which permits only a static-pressure component of the detection signal SP to pass therethrough, thereby supplying a cuff-pressure signal, SK, representing the detected static cuff pressure, $P_c$, to a control circuit 728 via an analog-to-digital (A/D) converter 726. The pulse-wave detector circuit 724 includes a band-pass filter (not shown) which permits only an oscillation component of the detection signal SP to pass therethrough, thereby supplying a pulse-wave signal, SM, representing a pulse wave of the subject, to the control circuit 728 via the A/D converter 726. The pulse wave is generated in the cuff 710 because of the pulsation of arteries of the upper arm under the cuff 710 in synchronism with the heartbeats of the subject, while the cuff pressure $P_c$ changes within an appropriate pressure range. Thus, the pulse wave generated in the cuff 710 is obtained as the oscillation component of the detection signal SP supplied from the pressure sensor 712.

The control circuit 728 is essentially constituted by a microcomputer including a CPU 730, a ROM 732, a RAM 734, and an output interface 736. The CPU 730 receives the digital signals SK and SM from the A/D converter 726, and processes those signals by utilizing the temporary-storage function of the RAM 734 and the control programs or algorithms pre-stored in the ROM 732. The CPU 730 supplies drive signals to the quick deflation valve 714, slow deflation valve 716, and air pump 718, to measure a blood pressure (BP) value of the subject. The CPU 730 carries out the pre-stored algorithms to supply, to an output device 738, a BP signal representing the measured BP value, a measurement-condition signal indicating whether the condition of measurement of the BP value is sufficiently proper, and a pulse-amplitude signal representing respective amplitudes of a series of successive pulses of the pulse wave (i.e., pulse-wave signal SM). The output device 738 includes an image display panel (not shown; e.g., liquid-crystal display panel) which has a matrix of picture elements. The output device 738 may further include a printer, as needed, which records using an ink an image on a recording sheet. The output device 738 outputs, on the image display panel or the recording sheet, the BP value of the subject, the propriety or non-propriety of the condition of the BP measurement, and the series of pulse amplitudes. Reference numeral 740 designates a START/STOP button manually operable for alternately starting and stopping the operation of the present BP measuring apparatus 700.

Hereinafter, there will be described the automatic BP measuring operation of the BP apparatus 700 constructed as described above, by reference to the flow charts of FIGS. 51 and 52.

Initially, at Step S301, the CPU 730 judges whether the START/STOP button 740 has been operated for starting the operation of the present apparatus 700, based on a START or STOP signal supplied from the button 740. If a negative judgment is made at Step S301, the control of the CPU 730 waits for receiving the START signal from the button 740. Meanwhile, if a positive judgment is made, the control of the CPU 730 proceeds with Step S302 to close the quick and slow deflation valves 714, 716 and drive the air pump 718 so as to start supplying a pressurized air to the inflatable cuff 710 and thereby increasing the air pressure in the cuff 510, i.e., cuff pressure $P_c$.

Step S302 is followed by Step S303 to judge whether the cuff pressure $P_c$ has been increased up to a prescribed target pressure, $P_m$ (e.g., 180 mmHg), which is sufficiently higher than a systolic blood pressure of the subject. If a negative judgment is made at Step S303, the CPU 730 repeats Step S303 to continue to increase the cuff pressure $P_c$. Meanwhile, if a positive judgment is made at Step S301, the control of the CPU 730 proceeds with Step S304 to stop the air pump 718 and open the slow deflation valve 716 so as to start deflating the cuff 710, i.e., decreasing the cuff pressure $P_c$. This cuff deflation or pressure decreasing is carried out slowly at a rate of, e.g., 2 to 3 mmHg/sec suitable for BP measurements. During this slow cuff deflation, Steps S305 and S306 are repeatedly carried out for determining a BP value of the subject.

Figure 52:
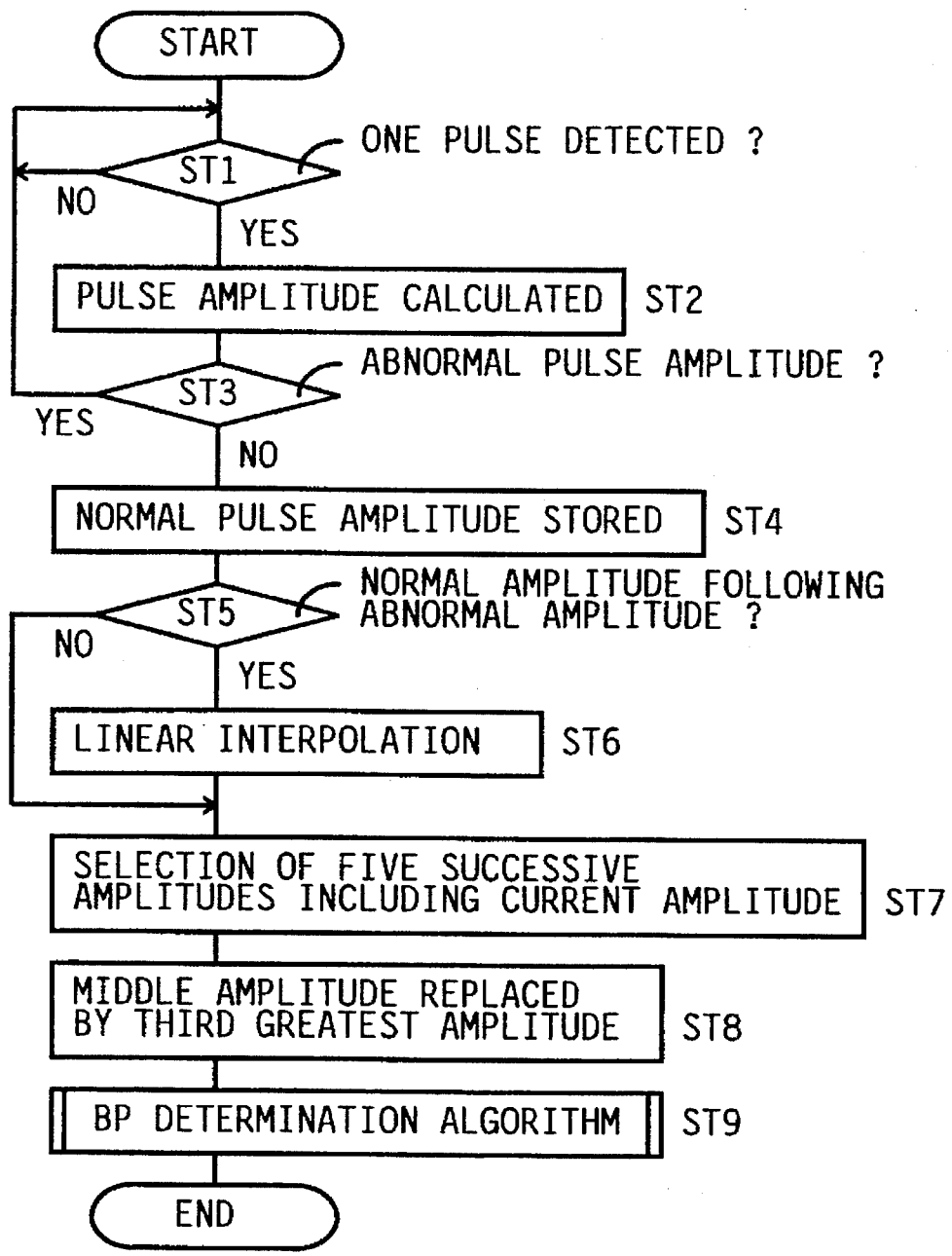
FIG. 52 is a flow chart representing the steps carried out in the subroutine of Step S305 of FIG. 51.

At Step S305, the BP determination subroutine represented by the flow chart of FIG. 52 is repeated at a short cycle or period, e.g., every four milliseconds. In this subroutine, respective amplitudes, R, of a series of successive pulses of the pulse wave signal SM are determined and pre-treated, and a BP value or values of the subject is or are determined based on the pulse amplitudes R according to a known BP determination algorithm.

First, at Step ST1, the CPU 730 reads, at a sampling period, respective magnitudes of the pulse wave signal SM supplied thereto from the A/D converter 726, and judges whether the CPU 730 has received a length of the pulse wave signal SM corresponding to one pulse having an amplitude, i.e., one cycle of heartbeat of the subject. If a negative judgment is made at Step ST1, the CPU 730 repeats Step ST1. Meanwhile, if a positive judgment is made at Step ST1, that is, if the CPU 730 reads in an upper peak and a lower peak of one pulse, the control of the CPU 730 proceeds with Step ST2 to calculate an amplitude, $R_i$, of the pulse by subtracting the lower-peak magnitude thereof from the upper-peak magnitude thereof. Step ST2 is followed by Step ST3 to judge whether the calculated pulse amplitude $R_i$ is abnormal, by identifying such a change of the current amplitude $R_i$ from the preceding amplitude $R_{i-1}$ which cannot physiologically be expected to occur. For example, in the case where the current amplitude $R_i$ is obtained before the cuff pressure $P_c$ is decreased below a mean BP value of the subject, the CPU 730 makes a positive or "abnormality" judgment if the current amplitude $R_i$ is smaller than half the preceding amplitude $R_{i-1}$ or greater than four times the same $R_{i-1}$; and, in the case where the current amplitude $R_i$ is obtained after the cuff pressure $P_c$ is decreased below the mean BP value of the subject, the CPU 730 makes an "abnormality" judgment if the current amplitude $R_i$ is smaller than half the preceding amplitude $R_{i-1}$ or greater than one and a half times the same $R_{i-1}$.

If a positive judgment is made at Step ST3, the control of the CPU 730 goes back to Step ST1 and the following steps. On the other hand, if a negative judgment is made at Step ST3, the control goes to Step ST4 to store, in an appropriate memory area of the RAM 734, the current pulse amplitude $R_i$ and a cuff pressure value $P_c$ at the time of supplying of the pulse amplitude $R_i$. Step ST4 is followed by Step ST5 to judge whether the current amplitude $R_i$ is the first normal amplitude following the last abnormal amplitude. If a negative judgment is made at Step ST5, the control of the CPU 730 bypasses Step ST6 and goes to Step ST7. On the other hand, if a positive judgment is made at Step ST5, the control goes to Step ST6 to carry out the "amp-filter" treatment that is disclosed in, e.g., the aforementioned non-examined Japanese patent application laid open under Publication No. 63-51837. That is, one or more abnormal amplitudes $R_{i-k}, \ldots, R_{i-2}, R_{i-1}$ preceding the current normal amplitude $R_i$ is or are subjected to linear interpolation based on the current amplitude $R_i$ and the normal amplitude $R_{i-k-1}$ preceding the one or more abnormal amplitudes $R_{i-k}, \ldots, R_{i-2}, R_{i-1}$.

At the following Steps ST7 and ST8, the series of pulse amplitudes $R_n$ that have been subjected to the amp-filter treatment at Step ST6, as needed, are subjected to the "median-filter" treatment so as to smoothen the amplitudes $R_n$. The median-filter treatment is disclosed in, e.g., the above Japanese patent application. Specifically, at Step ST7, the CPU 730 selects an odd number (e.g., five) of successive pulse amplitudes $R_{i-4}, R_{i-3}, R_{i-2}, R_{i-1}, R_i$ including the current amplitude $R_i$. Step ST7 is followed by Step ST8 to replace the middle amplitude $R_{i-2}$ by the third greatest amplitude $R_j$ of all the five amplitudes. In the present embodiment, Steps ST5 to ST8 and a portion of the control circuit 728 for carrying out those steps cooperate with each other to serve as means for smoothening the detected pulse amplitudes $R_n$. At Step ST7, the CPU 730 may be programmed to select three or seven or other odd number of successive pulse amplitudes other than five successive amplitudes.

After at Step ST8 the series of pulse amplitudes $R_n$ are smoothened, the control of the CPU 730 proceeds with Step ST9, i.e., BP determination algorithm for determining a systolic and a diastolic BP value of the subject based on the thus smoothened pulse amplitudes, $S_n$. Specifically described, the respective cuff pressure values $P_c$ corresponding to the two pulse amplitudes $S_i$ at which the series of pulse amplitudes $S_n$ significantly greatly change, are selected, and the selected two pressure values $P_c$ are determined as the systolic and diastolic BP values of the subject. The two determined BP values may be corrected, as needed, based on a prescribed relationship between systolic and diastolic BP values and/or a prescribed relationship between systolic or diastolic BP value and mean BP value. The two determined BP values are stored in an appropriate memory area of the RAM 734. Thus, in the present embodiment, the BP values of the subject are determined based on a pulse wave in the form of a heartbeat-synchronous signal wave, i.e., a pressure oscillation produced in the cuff 710 in synchronism with the heartbeats of the subject, the cuff 710 being wound around a body portion of the subject to press the body portion.

Figure 51:
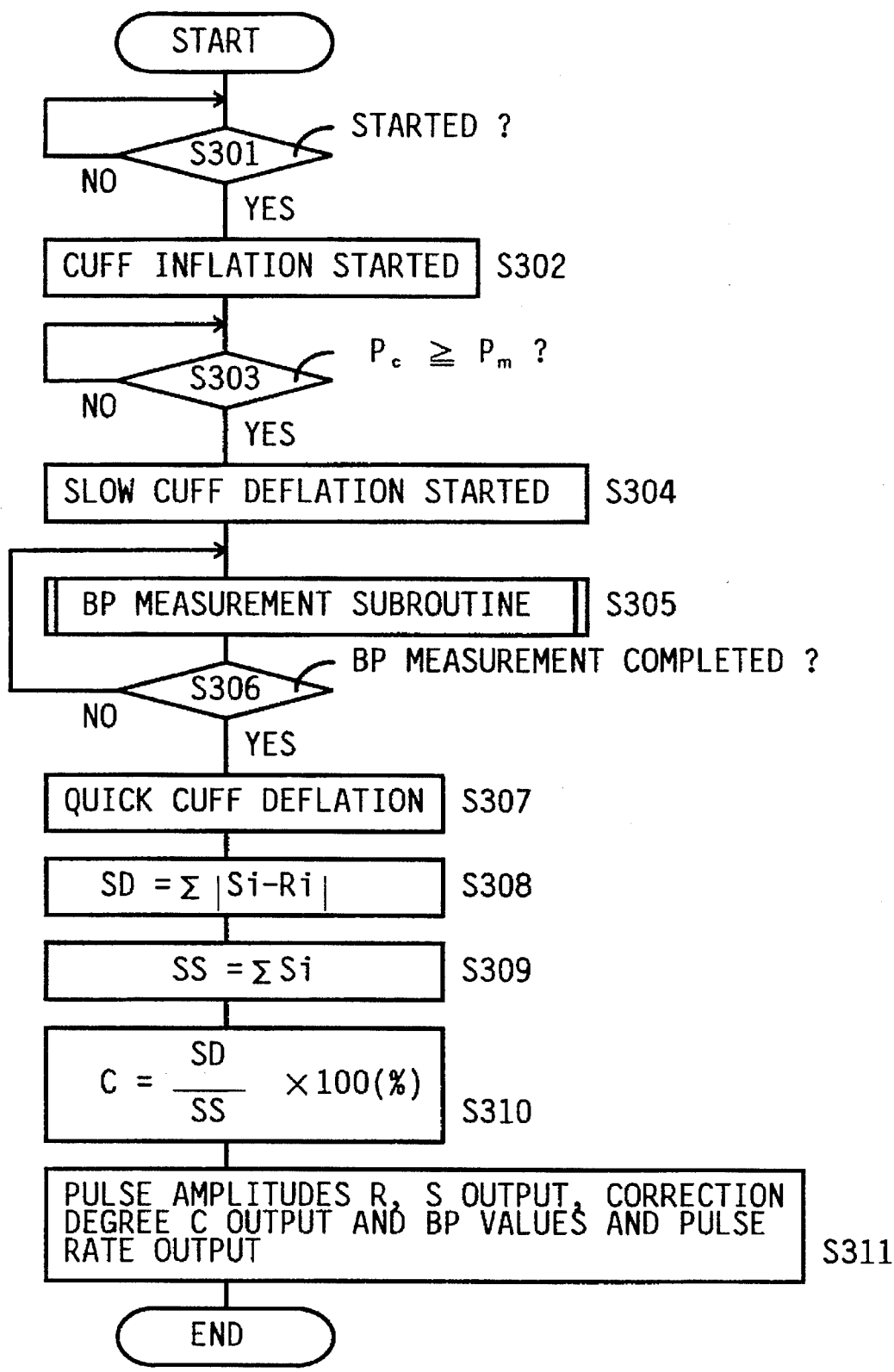
FIG. 51 is a flow chart representing a control program according to which the apparatus of FIG. 50 operates.

Back to the flow chart of FIG. 51, the control of the CPU 730 subsequently goes to Step S306 to judge whether the BP determination subroutine at Step S305 has been completed. For a while shortly after the beginning of the slow decreasing of the cuff pressure $P_c$, a sufficient number of pulse amplitudes $S_n$ have not been obtained. Therefore, the CPU 730 repeats Steps S305 and S306. Meanwhile, if a positive judgment is made at Step S306, that is, if the BP values of the subject have been determined at Step ST9 of FIG. 52, the control of the CPU 730 goes to Step S307.

At Step S307, the CPU 730 opens the quick deflation valve 715 to completely deflate the cuff 710, i.e., reduce the cuff pressure $P_c$ down to atmospheric pressure. At the following Steps S308, S309, and S310, the CPU 730 calculates a correction degree, C, i.e., degree of correction of the series of smoothened pulse amplitudes $S_n$ from the series of detected pulse amplitudes $R_n$. More specifically, at Step S308, the CPU 730 calculates a sum, SD of respective absolute values, $|S_i - R_i|$, each of which is obtained as a difference of pulse amplitudes $R_i$ and $S_i$ which correspond to a cuff pressure value $P_c$ within a prescribed pressure range, according to the following expression (3):

$$SD = \Sigma |S_i - R_i| \tag{3}$$

The above-mentioned pressure range may be predetermined to cover the pulse amplitudes $R_i, S_i$ ranging from the pulse amplitude $R_{u-1}, S_{u-1}$ outside and adjacent the pulse amplitude $R_u, S_u$ corresponding to the systolic BP value of the subject determined at Step ST9, to the pulse amplitude $R_{r+1}, S_{r+1}$ outside and adjacent the pulse amplitude $R_r, S_r$ corresponding to the determined diastolic BP value of the subject.

At the following Step S309, the CPU 730 calculates a sum, SS, of respective smoothened pulse amplitudes $S_i$ which correspond to the cuff pressure values $P_c$ within the above-mentioned pressure range, according to the following expression (4):

$$SS = \Sigma S_i \tag{4}$$

Step S309 is followed by Step S310 to calculate, as the correction degree C, a percentage of the sum SD to the sum SS, according to the following expression (5):

$$C=(SD/SS)\times 100(\%) \tag{5}$$

Thus, in the present embodiment, Steps S308 to S310 and a portion of the control circuit 728 for carrying out those steps cooperate with each other to serve as means for calculating the correction degree C.

Figure 53:
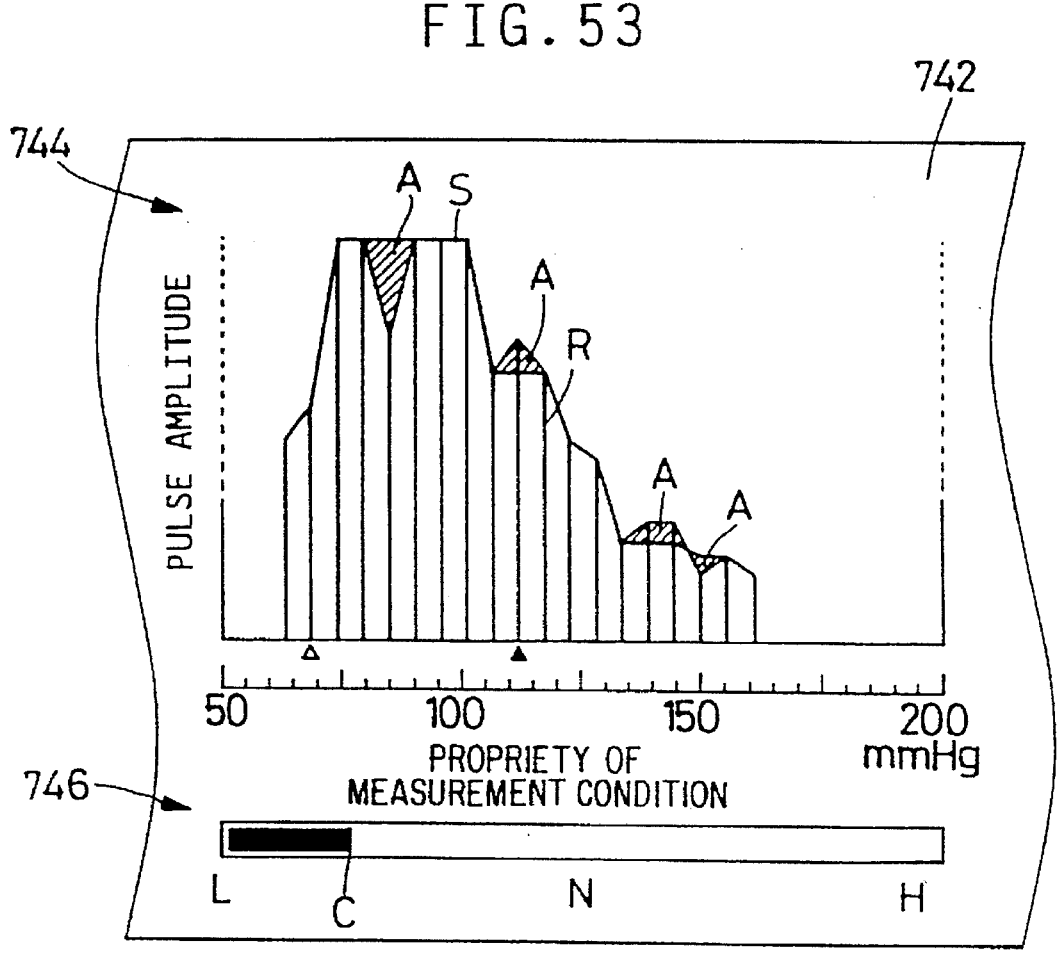
FIG. 53 is a view of an example of a pulse-amplitude indication (i.e., a series of detected pulse amplitudes and a series of smoothened pulse amplitudes) and a measurement-condition indication both of which are output by an output device of the apparatus of FIG. 50.

In FIG. 53, the first sum SD corresponds to a first area as a sum of shadowed areas, A; the second sum SS corresponds to a second area bounded by a polygonal line representing the series of smoothened pulse amplitudes $S_i$ and a base line parallel to the axis of abscissa, i.e., axis indicative of cuff pressure $P_c$. Therefore, the correction degree C corresponds to a ratio of the first area to the second area.

Step S310 is followed by Step S311 to control the output device 738 and/or another output device (not shown) to output the systolic and diastolic BP values, and pulse rate, of the subject. The pulse rate is determined based on the difference between the times of detection of respective upper (or lower) peaks of two successive pulses. In addition, at Step S311, the CPU 730 controls the output device 738 to record, on a recording sheet 742 shown in FIG. 53, a first graphic representation 744 including the first series of detected pulse amplitudes R and the second series of smoothened pulse amplitudes S, superimposed on each other, in a two-dimensional coordinate system defined by a first axis indicative of cuff pressure $P_c$ and a second axis indicative of pulse amplitudes R, S. The output device 738 also records, on the sheet 742, a second graphic representation 746 in a side-by-side relation with the first graph 744. The second graph 746 is indicative of a propriety of measurement condition, i.e., a correction degree C. The length of the "black" horizontal bar 746 corresponds to the determined correction degree C. The longer the bar 746 is, the higher the correction degree C is. The higher correction degree C indicates the higher degree of mixing of "noise" pulses with true pulses. In the first graph 744, the first series of detected pulse amplitudes R are indicated at vertical lines, and the second series of smoothened pulse amplitudes S are indicated at a polygonal line. The shadowed areas A bounded by (a) the envelope of the vertical lines and (b) the polygonal line represents the first sum SD. The two cuff pressure values $P_c$ corresponding to the systolic and diastolic BP values of the subject determined at Step ST9, are indicated at symbols ▲ and △, respectively, recorded along the first axis. The second graph 746 includes three marks "L", "N", and "H" indicating a low, a normal, and a high correction degree C, i.e., three degrees of mixing of "noise" pulses with true pulses, respectively. Thus, the second graph 746 indicates the degree of propriety of the current measurement condition under which the current BP values of the subject have been measured. Medical workers can recognize the current measurement condition by comparing the length of the "black" horizontal bar C with the marks "L", "N" or "H". For example, the normal correction degree C corresponding to the mark "N" may be selected at 5%, and the high correction degree C corresponding to the mark "H" may be selected at 9%. In the present embodiment, the control circuit 728 serves as a control device which controls the output device 738.

As is apparent from the foregoing description, the BP measuring apparatus 700 operates in such a way that at Step S311 the output device 738 outputs the first series of detected or sampled pulse amplitudes R and the second series of smoothened or processed pulse amplitudes S, the two sorts of pulse amplitudes R, S being superimposed on each other in the common two-dimensional graph 744. Therefore, medical workers such as doctors can visually recognize the differences, $D_i$, of the detected pulse amplitudes $R_i$ and the corresponding smoothened pulse amplitudes $S_i$. The differences $D_i$ correspond to the sun of areas A shown in FIG. 53. The differences $D_i$ may be increased due to external causes such as the physical motion of the subject or noise due to peripheral devices. Medical workers can easily judge whether the measured BP values of the subject contain excessively large errors due to the external causes, by recognizing the respective positions of the differences $D_i$, i.e., areas A with respect to the first axis, i.e., cuff-pressure axis of the common two-dimensional graph 744. That is, the medical workers can easily identify whether the condition of the BP measurement is proper. For example, in the case where the sum SD of the differences $D_i$ is excessively large because the series of smoothened pulse amplitudes S have been excessively largely corrected particularly in a range of cuff pressure $P_c$ between the determined systolic and diastolic BP values of the subject indicated at the respective symbols ▲, △ in the graph 744, medical workers can easily judge that the series of detected pulse amplitudes R have been excessively largely influenced by external causes and that the accuracy of measured BP values of the subject is insufficiently low and the condition of the BP measurement is not appropriate.

Since in the present embodiment the first series of detected pulse amplitudes R are indicated by vertical lines, the second series of smoothened pulse amplitudes S are indicated by a polygonal line, and the differences D of the two sorts of pulse amplitudes R, S are indicated by the shadowed areas A bounded by (a) the envelope of the vertical lines and (b) the polygonal line, observers can easily recognize the magnitude or amount of the sum of differences D, i.e., first sum SD.

In the present embodiment, the control circuit 728 or CPU 730 calculates the correction degree C as the percentage of the sum of areas A to the area bounded by (a) the polygonal line of the smoothened pulse amplitudes S and (b) the base line. The correction degree C indicates the degree of correction of the smoothened pulse amplitudes S from the detected pulse amplitudes R. The correction degree C is indicated by the horizontal bar in the second graph 746 provided in a side-by-side relation with the first graph 744 on the recording sheet 742 or on the image display panel (not shown) of the output device 738. Thus, observers can visually know what percent of correction has been made on the detected pulse amplitudes R. The observers can judge, based on the correction degree C, whether the measured BP values of the subject contain excessively large errors due to external factors, i.e., whether the condition of the BP measurement is proper. In addition, the second graph 746 includes the three marks or indicias "L" (i.e., 'noise is low'), "N" ('noise is normal') and "H" ('noise is high') respectively indicating the three degrees of propriety of the measurement condition. Thus, operators who are not familiar with the BP apparatus 700 can easily judge, based on the horizontal bar and the marks of the second graph 746, whether the measurement condition is proper or appropriate. For example, in the case where the right-hand end of the horizontal bar indicative of the correction degree C reaches a position between the marks "L" and "N", that is, a position where the correction degree C is smaller than 5%, the operators can judge that the condition of the BP measurement is proper. In the present embodiment, the correction degree C indicates the degree of propriety of the measurement condition, and the horizontal bar representing the correction degree C is output in a side-by-side relation with the marks "L", "N", "H" each representing a degree of propriety of measurement condition.

Figure 54:
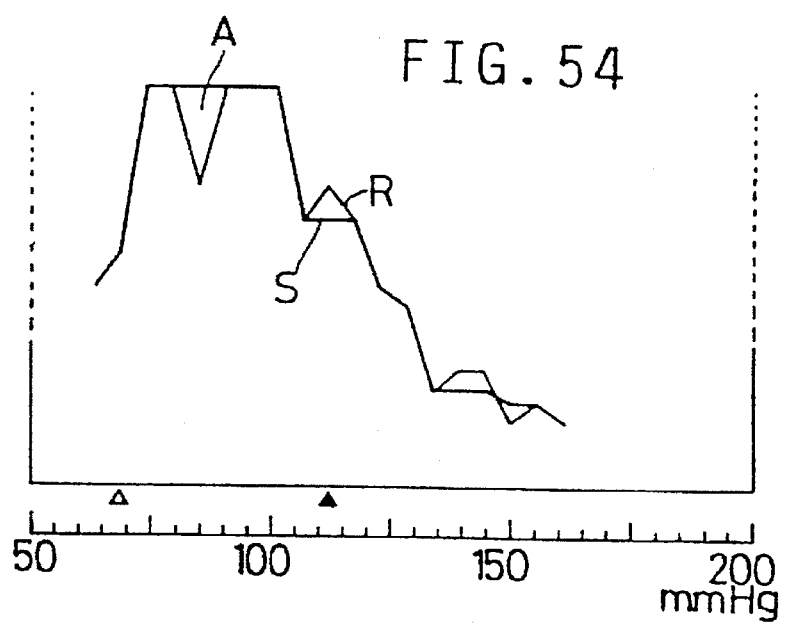
FIG. 54 is a view corresponding to FIG. 53, showing another example of a series of detected pulse amplitudes and a series of smoothened pulse amplitudes output by the apparatus of FIG. 50.
Figure 53:
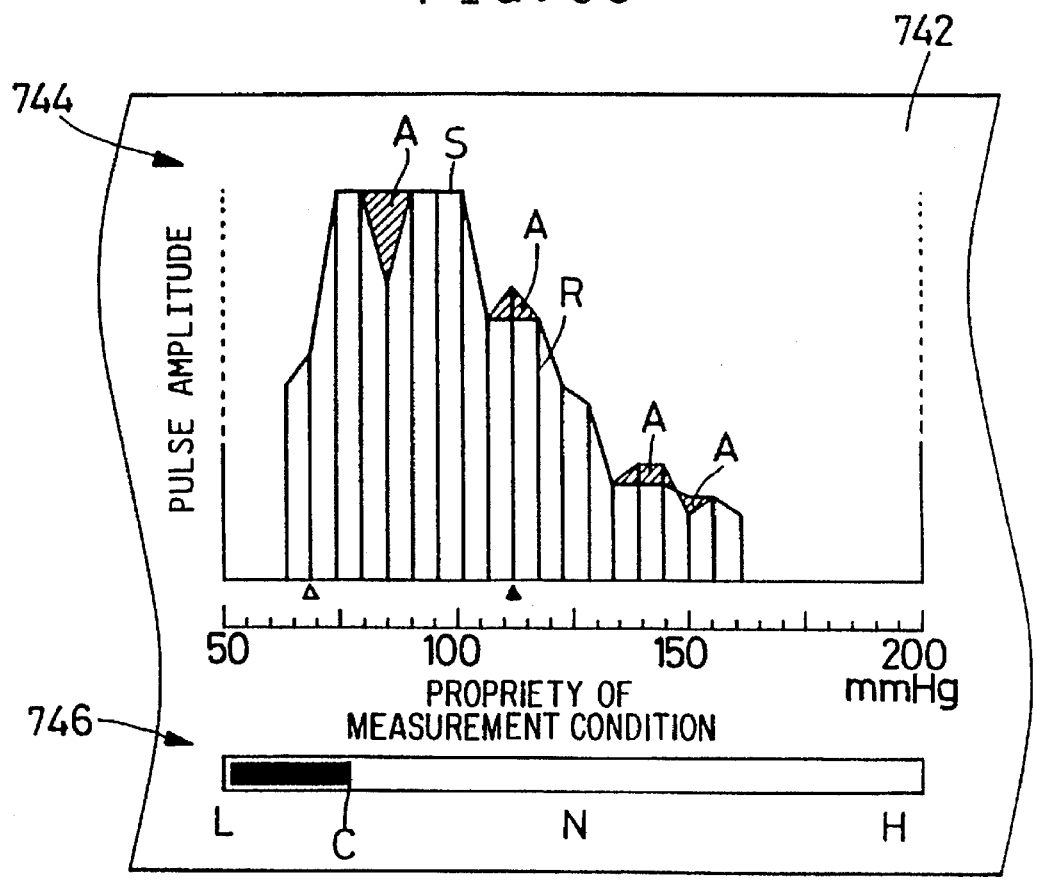
Figure 54:
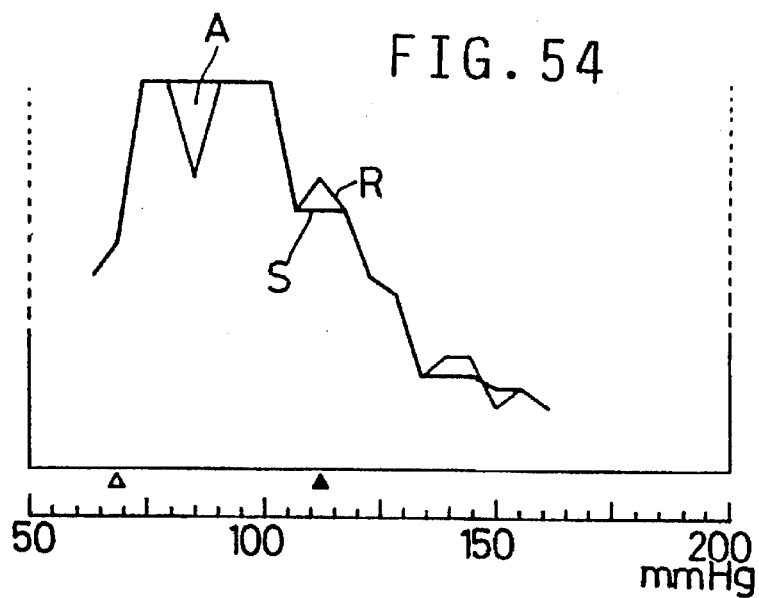

FIGS. 54, 55, 56, and 57 shows other forms of expression each corresponding to the two-dimensional graph 744 shown in FIG. 53. In FIG. 54, the series of smoothened pulse amplitudes S are indicated in the same manner as that employed in FIG. 53, but the series of detected pulse amplitudes R are indicated by not vertical lines but a polygonal line, like the smoothened pulse amplitudes S. In addition, areas A bounded by those two polygonal lines are not shadowed. Also in this case, observers can clearly recognize the differences $D_i$ of the two sorts of pulse amplitudes R, S in the common two-dimensional graph, and can easily judge whether the measured BP values of the subject contain excessively large errors due to external factors, i.e., whether the measurement condition is proper, based on (a) the sum of differences $D_i$ and (b) the respective positions of the differences $D_i$ with respect to the first axis of the common two-dimensional graph.

In the two-dimensional graph shown in FIG. 54, a portion or portions of the polygonal line of the smoothened pulse amplitudes S which is or are separate from a corresponding portion or portions of the polygonal line of the detected pulse amplitudes R, indicate(s) that data correction has been carried out on the portion or portions. Therefore, observes can easily recognize the differences $D_i$ of the two sorts of pulse amplitudes R, S.

Figure 55:
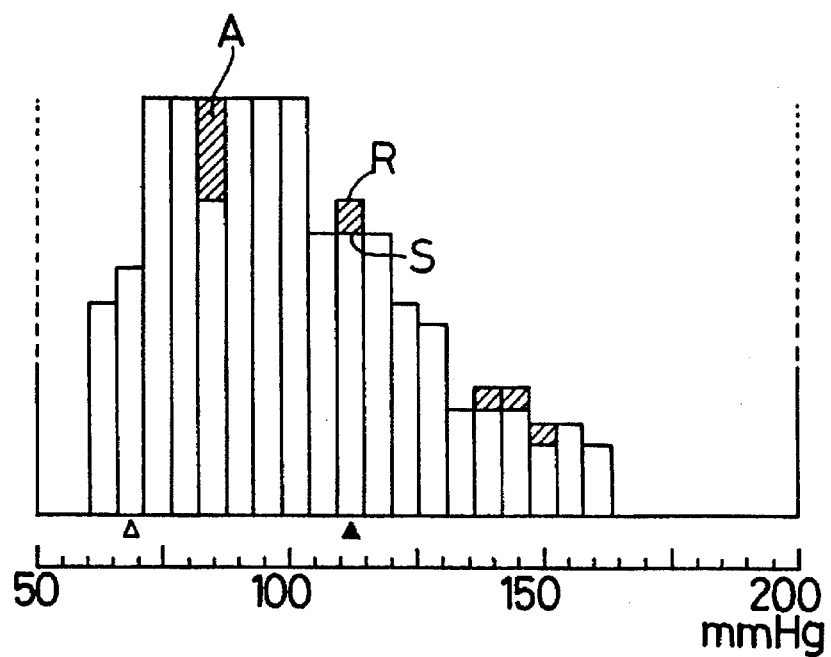
FIG. 55 is a view corresponding to FIG. 53, showing yet another example of a series of detected pulse amplitudes and a series of smoothened pulse amplitudes output by the apparatus of FIG. 50.

In the two-dimensional graph shown in FIG. 55, both the two sorts of pulse amplitudes R, S are indicated at bars, and areas A corresponding to the differences $D_i$ of the two sorts of pulse amplitudes R, S are indicated in a color or pattern different from a color or pattern used to indicate the other portions of the bars. For example, a light and a dark color may be used to distinguish the areas A and the other portions from each other. In this case, too, observers can clearly recognize the differences $D_i$ of the two sorts of pulse amplitudes R, S in the common two-dimensional graph, and can easily judge whether the measured BP values of the subject contain excessively large errors due to external factors, i.e., whether the measurement condition is proper, based on (a) the sum of differences $D_i$ and (b) the respective positions of the differences $D_i$ with respect to the first axis of the common two-dimensional graph.

Figure 56:
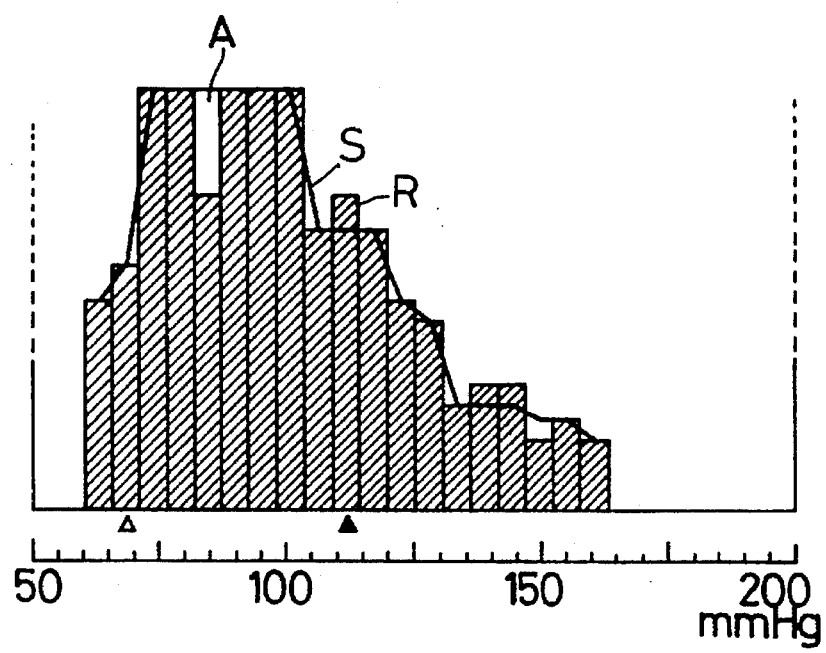
FIG. 56 is a view corresponding to FIG. 53, showing yet another example of a series of detected pulse amplitudes and a series of smoothened pulse amplitudes output by the apparatus of FIG. 50.

In the two-dimensional graph shown in FIG. 56, one of the two sorts of pulse amplitudes R, S (the smoothened pulse amplitudes S in the figure) are indicated at a polygonal line and the other (the detected pulse amplitudes R in the figure) are indicated at vertical bars. In this case, observers can visually recognize (a) a vertical bar or bars higher than a corresponding portion or portions of the polygonal line, (b) a portion or portions of the polygonal line higher than a corresponding vertical bar or bars, and (c) the differences $D_i$ of the heights of the higher bars and the heights of the corresponding portions of the polygonal line and the differences $D_i$ of the heights of the higher portions of the polygonal line and the heights of the corresponding bars. Thus, the observers can clearly recognize the differences $D_i$ of the two sorts of pulse amplitudes R, S in the common two-dimensional graph, and can easily judge whether the measured BP values of the subject contain excessively large errors due to external factors, i.e., whether the measurement condition is proper, based on (a) the sum of differences $D_i$ and (b) the respective positions of the differences $D_i$ with respect to the first axis of the common two-dimensional graph.

Figure 57:
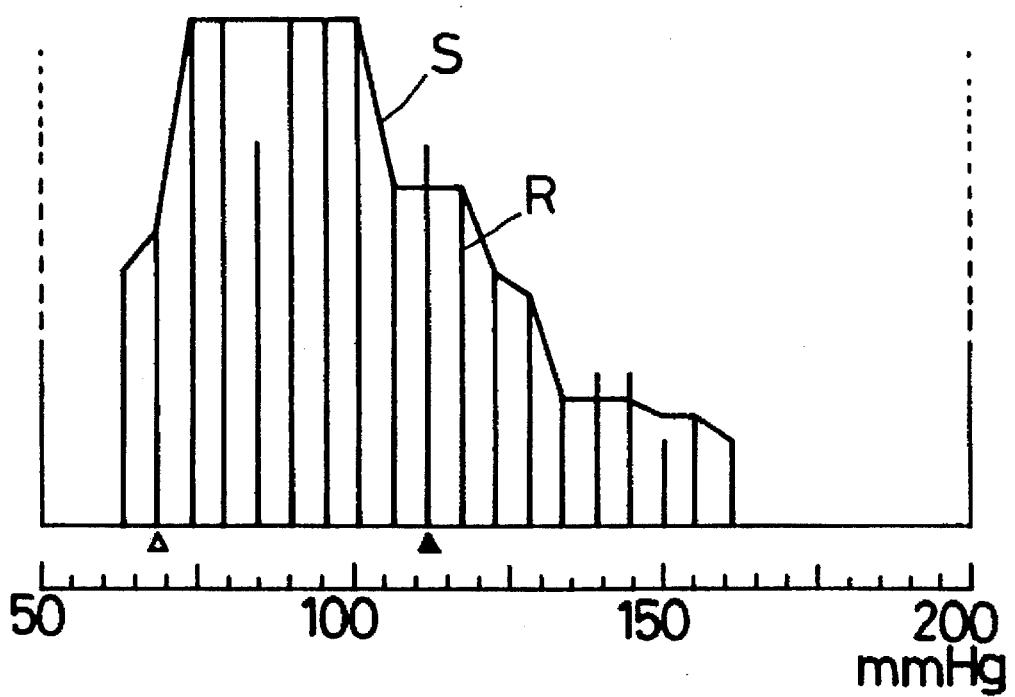
FIG. 57 is a view corresponding to FIG. 53, showing yet another example of a series of detected pulse amplitudes and a series of smoothened pulse amplitudes output by the apparatus of FIG. 50.

In the two-dimensional graph shown in FIG. 57, one of the two sorts of pulse amplitudes R, S are indicated at vertical lines and the other are indicated at a polygonal line, like in the graph shown in FIG. 53. However, the differences $D_i$ of the two sorts of pulse amplitudes R, S are not indicated at shadowed areas A, unlike the graph of FIG. 53. In this case, however, observers can visually recognize (a) a vertical line or lines higher than a corresponding portion or portions of the polygonal line, (b) a portion or portions of the polygonal line higher than a corresponding vertical line or lines, and (c) the differences $D_i$ of the heights of the higher vertical lines and the heights of the corresponding portions of the polygonal line and the differences $D_i$ of the heights of the higher portions of the polygonal line and the heights of the corresponding vertical lines. Thus, the observers can clearly recognize the differences $D_i$ of the two sorts of pulse amplitudes R, S in the common two-dimensional graph, and can easily judge whether the measured BP values of the subject contain excessively large errors due to external factors, i.e., whether the measurement condition is proper, based on (a) the sum of differences $D_i$ and (b) the respective positions of the differences $D_i$ with respect to the first axis of the common two-dimensional graph.

In each of the two-dimensional graphs shown in FIGS. 54–57, the measured systolic and diastolic BP values of the subject are indicated at symbols ▲, △ provided along the first axis, i.e., cuff-pressure axis of each two-dimensional graph. Therefore, observers can easily specify, in the two-dimensional graph, a cuff-pressure range to be utilized in judging whether the measurement condition is proper (e.g., cuff-pressure range between the measured systolic and diastolic BP values).

A horizontal bar representing a determined correction degree C may be indicated together with each of the graphs shown in FIGS. 54–57, like the second graph 746 indicated with the first graph 744 shown in FIG. 53. Alternatively, each of the graphs of FIGS. 54–57 may not be accompanied by a horizontal bar representing a correction degree C. Otherwise, the BP measuring apparatus 700 may be provided with another output device which indicates the correction degree C, i.e., degree of propriety of the measurement condition.

Figure 58:
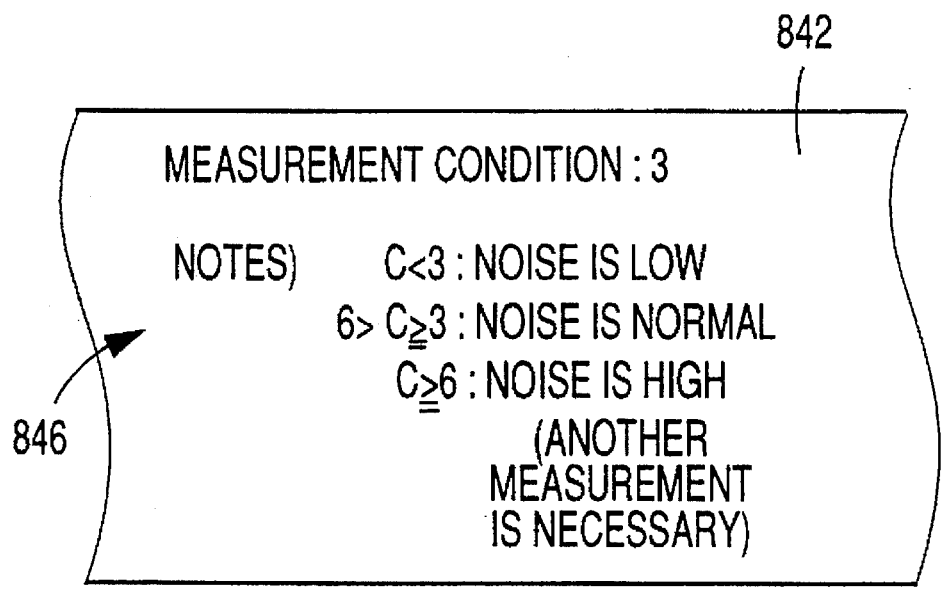
FIG. 58 is a view of another example of a measurement-condition indication output by the apparatus of FIG. 50.

The output device 738 may be modified to output a correction degree C in digits in a measurement-condition indication area 846 provided on a recording sheet 842 shown in FIG. 58. A pulse-amplitude indication area like the first graph 744 shown in FIG. 53 is not provided on the recording sheet 842. Below the correction degree C indicated in a digit or digits, notes are provided which read as follows: "3>C: NOISE IS LOW", "6>C≧3: NOISE IS NORMAL", and "C≧6: NOISE IS HIGH (ANOTHER MEASUREMENT IS NECESSARY)". Those notes may be used as standards in judging whether the correction degree C is excessively high. In this case, too, observers can easily judge whether the measured BP values of the subject contain excessively large errors due to external factors, i.e., whether the measurement conditions is proper, based on the output data 846 recorded on the sheet 842.

Figure 59:
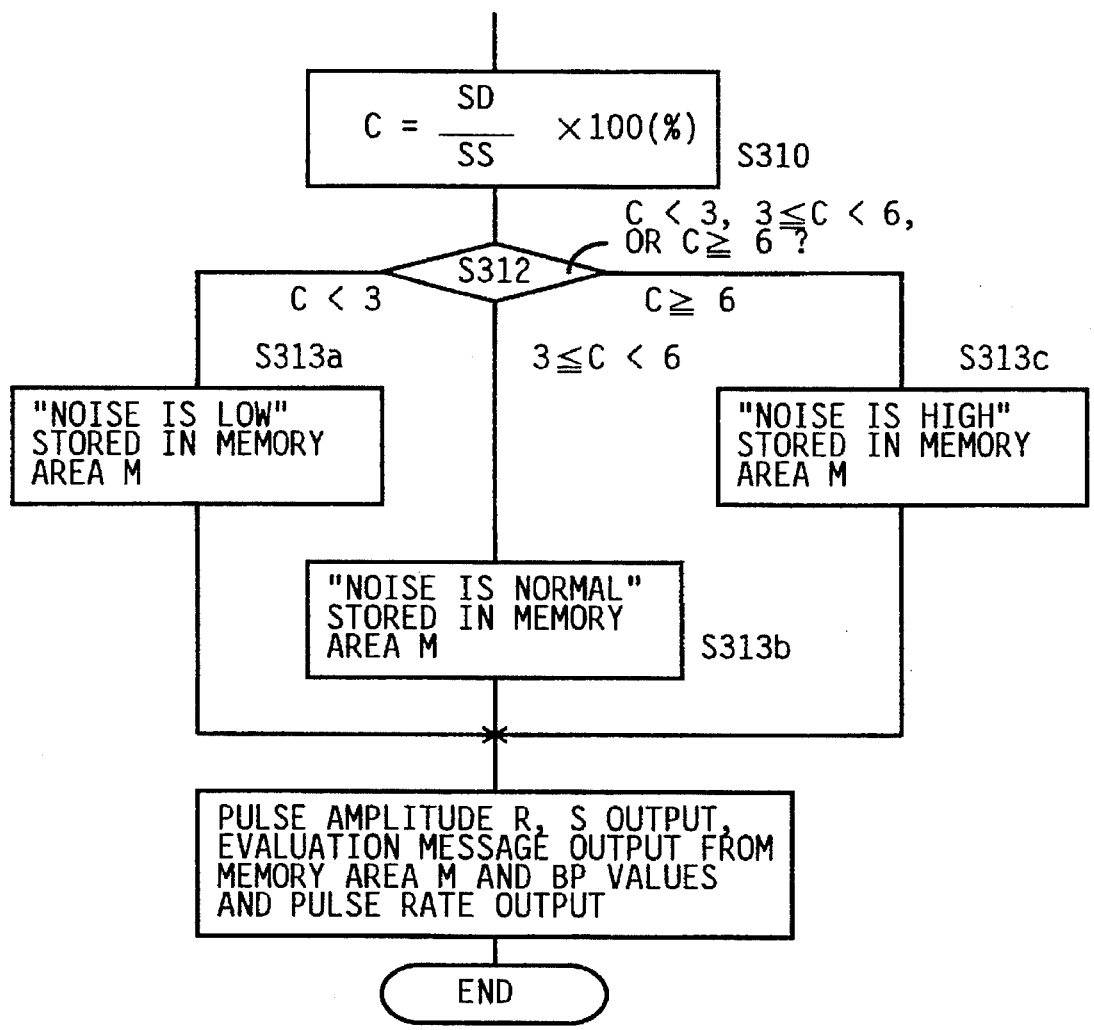
FIG. 59 is a flow chart including steps carried out to select and output an evaluation message corresponding to a determined correction degree C.

The indication of the degree of propriety of the measurement condition may otherwise be made than shown in FIG. 58 where the correction degree C in digits is recorded on the sheet 842. For example, the BP apparatus 700 may be modified to select one of evaluation messages, such as "NOISE IS LOW" or "NOISE IS HIGH", which corresponds to the determined correction degree C, and output the selected message in the measurement-condition indication area 846 of the recording sheet 842. In the latter case, as shown in FIG. 59, Steps S312, S313a, S313b, and S313c are provided after Step S310 of the flow chart of FIG. 51. More specifically, at Step S312, the CPU 730 compares the determined correction degree C with two reference values respectively corresponding to the evaluations of "NOISE IS NORMAL" and "NOISE IS HIGH", and judges whether the determined correction degree C is smaller than 3 as the first reference value, whether the degree C is not smaller than 3 and smaller than 6 as the second reference value, or whether the degree C is not smaller than 6. In the case of C <3, the control of the CPU 730 goes to Step S313a to select an evaluation message "NOISE IS LOW" and store the message in a memory area, M, of the RAM 734; in the case of 6>C≧3, the control goes to Step S313b to select an evaluation message "NOISE IS NORMAL" and store the message in the memory M; and, in the case of C≧6, the control goes to Step S313c to select an evaluation message "NOISE IS HIGH" and store the message in the memory M. Following Step S313a, S313b, or S313c, the control of the CPU 730 goes to Step S314 provided in place of Step S311 of FIG. 51. At Step S314, the CPU 730 controls the output device 738 to output, in place of the correction degree C, the evaluation message selected at Step S313a, S313b, or S313c, in the measurement-condition indication area 846 of the recording sheet 842. Otherwise, the BP apparatus 700 may be provided with a plurality of lamps related with different correction degrees C, so that the BP apparatus 700 may light one of the lamps which corresponds to a determined correction degree C.

It is to be understood that the sixth embodiment may be modified in other manners.

For example, while the BP apparatus 700 measures the BP values of the subject by utilizing, as a heartbeat-synchronous signal wave, a pulse wave produced in the cuff 710, it is possible to provide a microphone in the cuff 710 and detect using the microphone the Korotkoff sounds that are arterial sounds produced from the arteries of a body portion being pressed by the cuff 710. In the latter case, the Korotkoff sounds are utilized as a heartbeat-synchronous signal wave in BP measurements.

In the sixth embodiment, Step ST3 and a portion of the control circuit 728 for carrying out this step cooperate with each other to serve as means for judging whether each detected or determined pulse amplitude $R_i$ falls within a reference range and, if the pulse amplitude $R_i$ does not fall within the reference range, judging that the pulse amplitude $R_i$ is abnormal. Steps ST5 and ST6 and a portion of the control circuit 728 for carrying out these steps cooperate with each other to serve as means for replacing an abnormal pulse amplitude or amplitudes $R_i$ with a value or values obtained by interpolating two normal pulse amplitudes $R_j$ sandwiching the abnormal amplitude or amplitudes $R_i$. Step ST7 and a portion of the control circuit 728 for carrying out this step cooperate with each other to serve as means for sequentially selecting an odd number of successive pulse amplitudes $R_{i-2}$, $R_{i-1}$, $R_i$, $R_{i+1}$, $R_{i+2}$ from the series of determined pulse amplitudes R. Step ST8 and a portion of the control circuit 728 for carrying out this step cooperate with each other to serve as means for replacing the middle or center pulse amplitude $R_i$ with the pulse amplitude $R_j$ which has a median amplitude of the selected odd number of pulse amplitudes. Steps ST3, ST5, ST6, ST7, and ST8 and a portion of the control circuit 728 for carrying out these steps cooperate with each other to serve as means for smoothening the series of determined pulse amplitudes R. However, other kinds of smoothening means may be employed.

For example, Steps ST3, ST5, and ST6 may be omitted from the flow chart of FIG. 52, or Steps ST7 and ST8 may be omitted from the same. Alternatively, Step ST8 may be replaced with a step where the middle pulse amplitude $R_i$ is replaced with an average of the selected odd number of pulse amplitudes $R_{i-2}$, $R_{i-1}$, $R_i$, $R_{i+1}$, $R_{i+2}$. Only if a smoothing technique in any sense is applied to a series of determined pulse amplitudes R in determining a BP value of a living subject, the BP apparatus 700 outputs the first series of determined pulse amplitudes R and the second series of smoothened pulse amplitudes S, such that one series of the first and second series of pulse amplitudes R, S are superimposed on the other series in a common two-dimensional graph. In addition, the BP apparatus 700 outputs, based on a determined correction degree C, a degree of propriety of the measurement conditions under which the BP value of the subject is obtained. Thus, in any case, medical workers can easily judge, from the output of the BP apparatus 700, whether the measurement condition is proper or appropriate.

In each of the graphs shown in FIGS. 53 to 57, it is possible to exchange two symbols with each other for representing the two series of pulse amplitudes R, S, respectively. Moreover, in place of the vertical lines or the vertical bars, it is possible to use other symbols, patterns, or figures such as "star" mark or "snow" mark. In the graph of FIG. 53, the areas A may not be blacked out and only the polygonal line, vertical lines, and envelope of the vertical lines may be presented. In the graph of FIG. 54, the areas A may be blacked out. In each graph, the areas A may otherwise be made distinct by, e.g., being hatched with, e.g., oblique lines or a checked pattern.

Although in each of the graphs shown in FIGS. 53 and 55 the areas A are blacked out in the same manner irrespective of whether the determined pulse amplitudes R are higher or lower than the corresponding smoothened pulse amplitudes S, it is possible to distinguish some of the areas A where the determined pulse amplitudes R are higher than the corresponding smoothened pulse amplitudes S, from the other of the areas A where vice versa, by using different hatchings such as different oblique-line patterns.

From the output 742 of the BP apparatus 700 shown in FIG. 53, it is possible omit either one of (a) the pulse-amplitude indication area 744 where the two series of pulse amplitudes R, S are output, and (b) the measurement-condition indication area 746 where the correction degree C is output. From either one of the two sorts of information 744, 746 provided by the apparatus 700, medical workers can easily judge whether the measured BP values of the living subject contain excessively large errors due to external factors, i.e., whether the measurement condition is proper. In the case where the correction degree C is not determined or output, Steps S308 to S310 of the flow chart of FIG. 51 are omitted.

Although in the sixth embodiment the correction degree C is determined based on a ratio of the sum SD to the sum SS of the smoothened pulse amplitudes S, it is possible to calculate a different correction degree, C', based on a ratio of the sum SD to a sum, SR, of the determined pulse amplitudes R. Otherwise, it is possible to calculate a different correction degree by exchanging, in each of the two ratios, the numerator and the denominator with each other. In the cases where the ratios other than the ratio SD/SS are used, different criteria and/or reference values may be employed for judging whether the measurement condition is proper.

While in the sixth embodiment the correction degree C is calculated from the determined and smoothened pulse amplitudes R, S which correspond to a prescribed range of cuff pressure values $P_c$, it is possible to employ a different cuff-pressure range, as needed. For example, all the first and second series of pulse amplitudes R, S that correspond to all the cuff pressure values $P_c$ may be used to determine the correction degree C. Otherwise, a first narrow cuff-pressure range whose center value corresponds to the systolic BP value of the subject and a second narrow cuff-pressure range whose center value corresponds to the diastolic BP value of the same may be employed for the same purpose in these cases, too, different criteria and/or reference values may be employed for judging whether the measurement condition is proper.

Although in the sixth embodiment the output device 738 provides the recording sheet 742 bearing one or both of the pulse-amplitude indication 744 and the measurement-condition indication 746, it is possible to modify the output device 738 such that the output device 738 displays, on the image display panel thereof, one or both of the two indications 744, 746.

It is to be understood that the present invention may be embodied with other changes, improvements, and modifications that may occur to those skilled in the art without departing from the scope and spirit of the present invention defined by the appended claims.

What is claimed is:

1. An apparatus for measuring a blood pressure of a living subject, comprising:

an inflatable cuff adapted to be wound around a body portion of the subject, said cuff being inflated to provide a cuff pressure to press said body portion;

a pressure changing device which changes said cuff pressure;

a blood pressure measuring device which (a) obtains a heartbeat-synchronous signal wave generated from arteries of said body portion in synchronism with heartbeat of the subject while said cuff pressure is changed by said pressure changing device, (b) determines respective amplitudes of a plurality of successive pulses of said heartbeat-synchronous signal wave each of which corresponds to one cycle of heartbeat of the subject, and provides, as a first series of determined pulse amplitudes, the determined pulse amplitudes arranged in an order of generation of the corresponding pulses, (c) smoothens said first series of determined pulse amplitudes and thereby provides a second series of smoothened pulse amplitudes, and (d) determines a blood pressure value of the subject based on a change in said second series of smoothened pulse amplitudes;

an output device which outputs a two-dimensional representation comprising a number of picture elements; and a control device which controls said output device to output said two-dimensional representation representative of said first series of determined pulse amplitudes and said second series of smoothened pulse amplitudes such that one of said first and second series of pulse amplitudes are superimposed on the other series of pulse amplitudes.

2. An apparatus according to claim 1, wherein said output device comprises means for outputting said two-dimensional representation representative of said first and second series of pulse amplitudes in a two-dimensional coordinate system defined by a first axis indicative of cuff pressure and a second axis indicative of pulse amplitude.

3. An apparatus according to claim 2, wherein said output device further comprises means for outputting, along said first axis, at least one symbol representative of said blood pressure value determined by said blood pressure measuring device.

4. An apparatus according to claim 1, wherein said output device comprises means for outputting said two-dimensional representation comprising a first and a second representation selected from a series of lines, a series of bars, and a polygonal line, said first and second representations being representative of said first and second series of pulse amplitudes, respectively.

5. An apparatus according to claim 1, wherein said output device comprises means for outputting said two-dimensional representation representative of said first series of determined pulse amplitudes and said second series of smoothened pulse amplitudes such that respective different portions of the determined pulse amplitudes and the corresponding smoothened pulse amplitudes are indicated in a color different from a color in which respective common portions of the determined pulse amplitudes and the smoothened pulse amplitudes are indicated.

6. An apparatus according to claim 1, wherein said output device comprises at least one of an image display device and a printer.

7. An apparatus for measuring a blood pressure of a living subject, comprising:

an inflatable cuff adapted to be wound around a body portion of the subject, said cuff being inflated to provide a cuff pressure to press said body portion;

a pressure changing device which changes said cuff pressure;

a blood pressure measuring device which (a) obtains a heartbeat-synchronous signal wave generated from arteries of said body portion in synchronism with heartbeat of the subject while said cuff pressure is changed by said pressure changing device, (b) determines respective amplitudes of a plurality of successive pulses of said heartbeat-synchronous signal wave each of which corresponds to one cycle of heartbeat of the subject, and provides, as a first series of determined pulse amplitudes, the determined pulse amplitudes arranged in an order of generation of the corresponding pulses, (c) smoothens said first series of determined pulse amplitudes and thereby provides a second series of smoothened pulse amplitudes, and (d) determines a blood pressure value of the subject based on a change in said second series of smoothened pulse amplitudes;

an output device which outputs a degree of propriety of a measurement condition under which said blood pressure value of the subject is determined by said blood pressure measuring device;

calculating means for calculating a degree of correction of said second series of smoothened pulse amplitudes from said first series of determined pulse amplitudes, by calculating a ratio of (a) respective differences between (a1) the determined pulse amplitudes corresponding to respective pressure values of said cuff within a prescribed pressure range and (a2) the corresponding smoothened pulse amplitudes, to (b) at least one of said determined pulse amplitudes and said corresponding smoothened pulse amplitudes; and a control device which controls said output device to output said degree of propriety of said measurement condition which corresponds to the degree of correction of said second series of pulse amplitudes calculated by said calculating means.

8. An apparatus according to claim 7, wherein said output device comprises means for outputting a bar whose length is variable with said degree of propriety of said measurement condition.

9. An apparatus according to claim 7, wherein said output device comprises means for outputting one of a plurality of different numbers corresponding to a plurality of degrees of propriety of said measurement condition, respectively.

10. An apparatus according to claim 7, wherein said output device comprises means for outputting one of a plurality of different messages corresponding to a plurality of degrees of propriety of said measurement condition, respectively.

11. An apparatus according to claim 7, wherein said output device comprises outputting means for outputting a two-dimensional representation comprising a number of picture elements representative of said first series of determined pulse amplitudes and said second series of smoothened pulse amplitudes such that one of said first and second series of pulse amplitudes are superimposed on the other series of pulse amplitudes.

12. An apparatus according to claim 11, wherein said outputting means comprises a means for outputting said two-dimensional representation with said degree of propriety of said measurement condition.

* * * * *